US008968806B2

(12) United States Patent
Delaney

(10) Patent No.: US 8,968,806 B2
(45) Date of Patent: Mar. 3, 2015

(54) METHOD AND SYSTEM FOR CREATING AND USING A SUPPLEMENT TO BALANCE ANIMAL DIETS

(76) Inventor: Sean Joseph Delaney, Davis, CA (US)

(*) Notice: Subject to any disclaimer, the term of this patent is extended or adjusted under 35 U.S.C. 154(b) by 1915 days.

(21) Appl. No.: 11/115,584

(22) Filed: Apr. 26, 2005

(65) Prior Publication Data

US 2006/0240150 A1  Oct. 26, 2006

(51) Int. Cl.
| A23K 1/18 | (2006.01) |
| A23L 1/29 | (2006.01) |
| A23L 1/302 | (2006.01) |
| A23L 1/303 | (2006.01) |
| A23L 1/304 | (2006.01) |
| A23L 1/305 | (2006.01) |

(52) U.S. Cl.
CPC .............. *A23L 1/293* (2013.01); *A23L 1/302* (2013.01); *A23L 1/303* (2013.01); *A23L 1/304* (2013.01); *A23L 1/3051* (2013.01); *A23V 2002/00* (2013.01)
USPC ........................................................ 426/72

(58) Field of Classification Search
CPC .................................................. A23K 1/1846
See application file for complete search history.

(56) References Cited

U.S. PATENT DOCUMENTS

| 5,583,083 A | 12/1996 | Ala-Huikku et al. | |
| 5,883,083 A | 3/1999 | Harless | |
| 5,954,640 A | 9/1999 | Szabo | |
| 6,083,006 A | 7/2000 | Coffman | |
| 6,165,539 A * | 12/2000 | Erasmus et al. | 426/629 |
| 6,358,546 B1 | 3/2002 | Bebiak | |
| 6,488,970 B1 * | 12/2002 | Hora | 426/72 |
| 6,493,641 B1 | 12/2002 | Singh et al. | |
| 6,576,280 B2 | 6/2003 | Bebiak et al. | |
| 6,613,368 B2 * | 9/2003 | Kloti | 426/74 |
| 6,669,975 B1 | 12/2003 | Abene et al. | |
| 6,681,717 B2 | 1/2004 | Burghardi et al. | |
| 2002/0120402 A1 | 8/2002 | Burghardi | |
| 2003/0077254 A1 | 4/2003 | Ramaekers | |
| 2003/0147971 A1 | 8/2003 | Myers | |
| 2003/0194423 A1 | 10/2003 | Torney | |
| 2004/0001817 A1 | 1/2004 | Giampapa | |
| 2004/0081743 A1 | 4/2004 | Laflamme et al. | |
| 2004/0156882 A1 | 8/2004 | Davenport | |
| 2004/0236609 A1 | 11/2004 | Keiser et al. | |

FOREIGN PATENT DOCUMENTS

WO  WO 02/096221  * 12/2002  .............. A23L 1/212

OTHER PUBLICATIONS

Dzanis The Association of American Feed control Officials Dog and cat Food Nutrient Profiles: Substantiation of Nutritional Adequacy of Complete and Balanced Pet Foods in the United States Journal of Nutrition vol. 124, pp. 2535S-2539S (1994).*
DaSilva et al. The Domestic Cat as a Laboratory Animal for Experimental Nutrition Studies Journal of Nutrition vol. 68, pp. 213-229 (1959).*
Street et al. Some Observations of Vitamin B6 Deficiency in the Dog Journal of Nutrition vol. 21, pp. 275-290 (1941).*
Google.com definitions of vitamin B6 [retrieved on Jul. 21, 2010] retrieved from the internet www.google.com/search?sourceid=navclient&ie=UTF-8&oe=UTF-8&q=define%3A+vitamin+b6.*
Google.com definition of retinol [retrieved on Jul. 21, 2010] retrieved from the internet www.google.com/search?hl=en&q=define%3A+retinol&btnG=Search.*
Wikipedia definition of calorie [retrieved on Jul. 21, 2010] retrieved from the internet en.wikipedia.org/wiki/Calorie.*
Leistra et al. Evaluation of selected-protein-source diets for management of dogs with adverse reactions to foods Journal of the American Veterinary Association vol. 219, pp. 1411-1414 (2001).*
Guilford et al. Prevalence and Causes of Food Sensitivity in Cats with Chronic Pruritus, Vomiting, or Diarrhea The Journal of Nutrition vol. 128, pp. 2790S-2791S (1998).*
Ardahanlioglu et al. Spatial variability in exchangeable sodium, electrical conductivity, soil pH and boron content in salt- and sodium-affected areas of the Igdir plain (Turkey) Journal of Arid Environments vol. 54, pp. 495-503 (2003).*
Yamada et al. Chemical forms and stability of selenium in soil Soil Science and Plant Nutrition vol. 44, pp. 385-391 (1998).*
Food For Thought TM Technical Bulletin No. 90R, published online by the Iams Company, [retrieved on May 12, 2007] retrieved from the Internet http://www.iams.com/en_AU/jhtmls/nutritions/sw_NutritionQuestions_qanswer.jhtml?li=en.

* cited by examiner

*Primary Examiner* — John S Brusca
(74) *Attorney, Agent, or Firm* — Temmerman Law Office; Mathew J. Temmerman

(57) ABSTRACT

The present invention provides a computer program for determining the optimum diet of an animal, determining what nutritional deficiencies exist in that diet, and formulating a supplement to correct those deficiencies. It allows the creation of a nutritionally complete and balanced diet with a sufficient but not excessive quantity of water, energy, protein, fat, carbohydrate, amino acids, fatty acids, vitamins, minerals, and vitamin-like nutrients. The specific compositions of supplements generated using the computer program are also claimed.

24 Claims, 6 Drawing Sheets

METHOD AND SYSTEM FOR CREATING AND USING A SUPPLEMENT TO BALANCE ANIMAL DIETS

BACKGROUND OF THE INVENTION

1. Field of Invention

The present invention relates to computer-assisted nutritional systems.

2. General Background

Pets have varying nutritional needs, depending on their species, breed, size, age, health status, and other conditions. Because of this variability in dietary needs, it has been difficult for pet owners and veterinary professionals to design and implement appropriate pet-specific diets. This difficulty is compounded by the use of human foods for pet nutrition, since the wide variety of available foods creates a great number of dietary permutations.

To design an appropriate pet-specific diet, it is first necessary to assess the nutritional and caloric attributes of the pet's current diet. Then a nutritional profile should be generated, detailing the pet's specific nutritional requirements. Next, various diets could be measured against the pet's nutritional profile, to determine which diet or diets are appropriate for the pet. Finally, it would typically be desirable to supplement the diet, and ideally the supplement that is selected would be compatible with a wide range of diets.

Unfortunately, pet owners and veterinary professionals do not currently have the tools to satisfactorily complete any of the tasks listed above. There is no comprehensive database containing the nutritional attributes of foods that are commonly fed to pets, including commercially available pets foods and selected human foods. Without such a database, it may be difficult to assess the nutritional properties of a pet's current diet.

Also, there is no tool or system currently available that can generate a nutritional profile for a wide variety of pets, based on a pet's particular attributes, such as breed, age, health-condition, etc. Instead, the current methods for creating a nutritional profile are cumbersome, and often rely on guesswork.

Nor is there any comprehensive and computerized tool that can assess the extent to which a particular diet fulfills the requirements for a particular nutritional profile. Instead, pet owners and even veterinarians must consult with veterinary nutritionists to complete the difficult task of designing a diet for the special needs of a particular pet. This process is difficult and time-consuming, and becomes even more challenging when the pet requires intravenous nutrition or tube feeding.

Similarly, there is currently no way to create a custom supplement formulated to provide the greatest benefit to the most diets. Current supplements typically contain a percentage of the recommended daily requirement without regard to the foods with which the supplement will actually be used. This generates the possibility that the supplement will be deficient for some nutrients and excessive for others.

SUMMARY OF THE INVENTION

The present invention is a computer program that solves all of the above problems. Although this patent primarily describes the invention as applied to pets, it can also be used with other animals and humans. The word "subject" is used to generically include all animals as well as humans.

The present system automatically completes and balances all nutritional requirements for a given diet, if it is possible to complete and balance the diet. The program also analyzes every possible combination of diets created from a list of foods the subject is likely to consume. From this analysis, the program determines common dietary deficiencies and formulates a custom supplement to correct them.

The present invention also analyzes the effectiveness of all commercially-available foods to a pet's special nutritional needs, and determines whether any will suffice. Commercial pet foods are less expensive and more convenient than human foods, but with the myriad choices of pet food, it may be difficult to identify commercial foods that meet a given pet's nutritional needs. Thus, the present invention includes a Commercial Food Selector that allows a user to identify whether any commercial food meets those needs.

Finally, by rapidly testing a nearly unlimited number of possible diets based on common foods, the present invention allows the creation of a universal supplement. For each diet, the system calculates the amount of each nutrient that is needed from the supplement, as well as the maximum amount of each nutrient that each diet can handle without exceeding a safe upper limit. From these data, an optimum supplement formulation is generated that, when applied to every diet, provides the recommended amount of all nutrients to the greatest number of potential diets consumed by the subject.

Calculations of the order required to create such a supplement are only possible using the advanced capabilities of today's computers. Computing the same formula using a typical computer from even a decade ago would have taken significantly more time, and performing the calculations without the aid of a computer would take a prohibitive amount of time.

Although in a preferred embodiment, the entire program runs using client-sever technology over a network such as the Internet, other embodiments may employ a single computer.

DETAILED DESCRIPTION

Introduction

Figure 1:
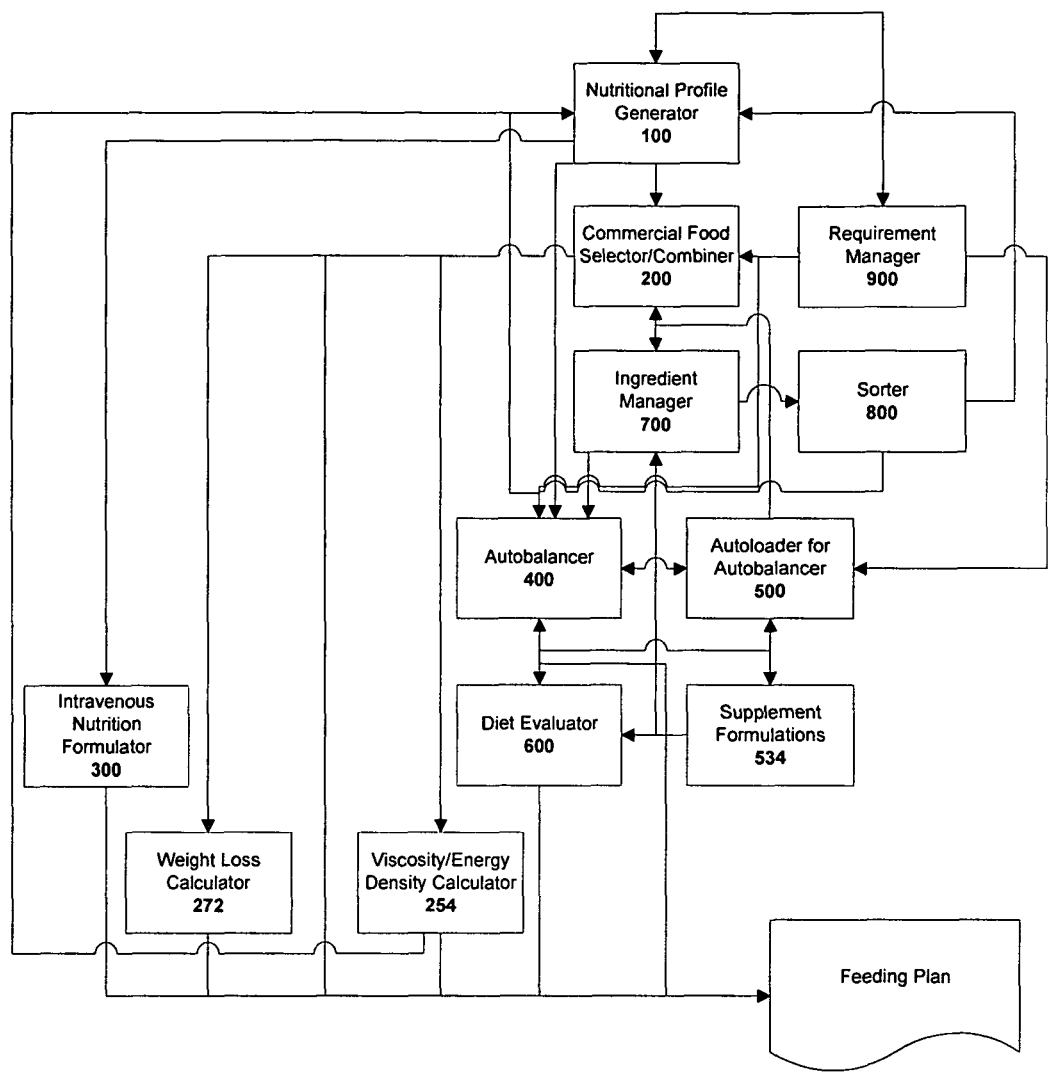
FIG. 1 is a flowchart of a computer-assisted nutritional system according to an embodiment of the present invention.

The present invention is a nutritional software application, comprising a number of modules as shown in FIG. 1: (i) a Nutritional Profile Generator (100), (ii) a Commercial Food Selector (200), (iii) an Intravenous Nutrition Formulator (300), (iv) an Autobalancer (400), (v) an Autoloader for Autobalancer (500), (vi) a Diet Evaluator (600), (vii) a Viscosity/Energy Density Calculator (254), (viii) a Weight Loss Calculator (272), (ix) an Ingredient Manager (700), (x) a Sorter (800), and (xi) a Requirement Manager (900). Each of these modules is described below. The present invention also includes "universal" supplements that have been formulated using the present software.

As used herein, feline and cat are used synonymously and canine and dog are used synonymously.

As used herein, a "completed diet" is a diet in which all required nutrients are present. Diets may be complete but still have deficiencies due to inadequate amounts of the nutrients.

As used herein, a balanced diet is a diet where all present nutrients are at levels that meet the minimum requirement but do not exceed the maximum requirement. Thus, a balanced diet is not necessarily completed and a completed diet is not necessarily balanced. That is, a diet may have all of the required nutrients in inadequate amounts, or it may have an inadequate number of nutrients, but those it has are in the proper amounts.

Nutritional Profile Generator

Figure 2:
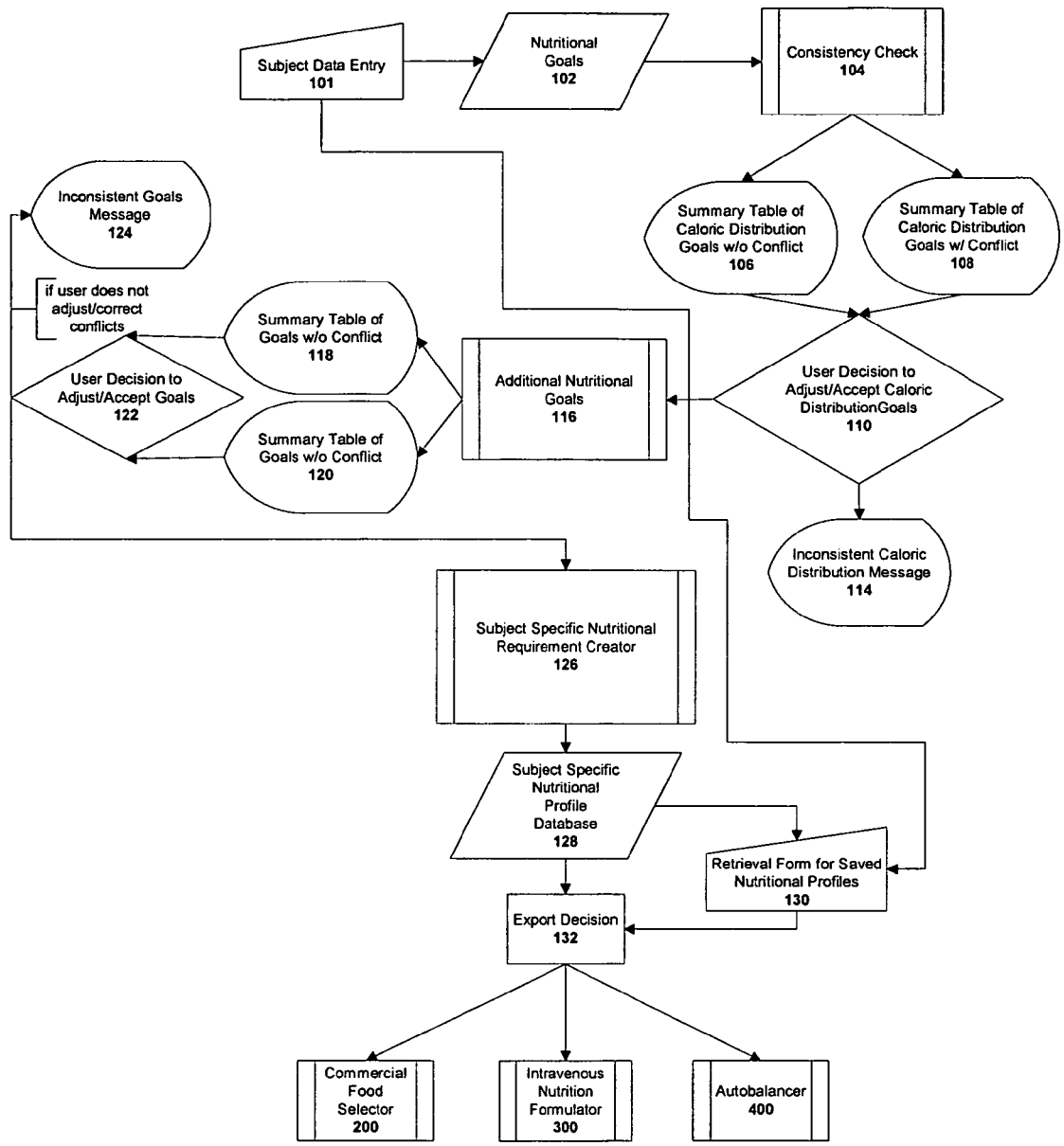
FIG. 2 is a flowchart of a Nutritional Profile Generator module according to an embodiment of the present invention.

A first module, shown in FIG. 1 block 100 and in detail in FIG. 2 is the Nutritional Profile Generator. This module has an algorithm that creates a custom set of nutrient requirements and other nutritional parameters based on subject-specific attributes. The custom set of nutrient requirements and other nutritional parameters is referred to as the Subject Specific Nutritional Profile (hereinafter nutritional profile). See FIG. 3, block 202. The program uses the nutritional profile in the search, identification, or creation of an appropriate diet for a subject. In one embodiment, the module may provide for various user access levels that restrict the number of diets the program allows any given user to create. For example, unlimited access granted to a medical professional may allow for the creation of diet plans using data regarding the diseased state of a subject, while restricted access for the general public may only provide for the creation of a diet plan for a healthy subject.

The first step of the Nutritional Profile Generator is to gather attributes about a subject. See FIG. 2, block 101. Such attributes include but are not limited to the subject's age, sex, reproductive status, breed, species, activity level, weight, body fat percentage, state(s) of health, and state(s) of disease. Health states include but are not limited to different life stages such as growing, adulthood, pregnancy, and lactation. Disease states include but are not limited to adverse reactions to food, anorexia associated with illness, cardiovascular disease, colitis, constipation, copper storage disease, diabetes mellitus, diarrhea, exocrine pancreatic insufficiency, hepatic encephalopathy, hepatic failure, hyperlipidemia, hypertriglyceridemia, inflammatory bowel disease, neoplasia, nonspecific gastroenteritis, osteoarthritis, obesity, pancreatitis, refeeding syndrome, renal insufficiency, renal failure, urolithiasis, and vomiting.

At the second step, as shown in block 102, the program generates a list of nutritional goals for the subject. This information is retrieved from a database of nutritional goals based on the subject attributes inputted at block 101. As used herein, database is defined as any collection of data in any medium. One common nutritional goal is an optimum caloric distribution. The caloric distribution dictates what percent of calories are to be derived from the macronutrients protein, fat and carbohydrate.

The database of nutritional goals contains different caloric distributions for a wide range of ailments that may afflict an animal. For instance, it may contain a specific caloric distribution for: calcium oxalate urolithiasis, hepatic encephalopathy after low protein meals, pancreatitis, and renal insufficiency. Many other caloric distributions and nutritional goals are possible.

For nearly any given ailment inputted in block 101, the program may assign a specific nutritional goal from the database of nutritional goals. See block 102. Each nutritional goal may include specific goals not only for caloric distribution, but also for nutrients including amino acids, essential fatty acids, essential fatty acid ratios, minerals, vitamins, and other goals such as the suggestion to use novel ingredients. However, the first nutritional goal generated is for caloric distribution.

Some nutritional goals may conflict with one another. For instance, a growing dog has a high protein requirement, while dogs with renal insufficiency have a low protein requirement. Thus, growing dogs with renal insufficiency may have nutritional goals in conflict, and the program would identify this possibility at block 104. However, because many goals comprise a wide range of acceptable caloric distributions, two goals may not necessarily be incompatible with one another. The program determines whether the two goals may coexist without conflict.

Blocks 106 and 108 display the two possible results of the consistency check shown in block 104. In block 106, the program displays results when there is no conflict between or among goals; and in block 108, the program displays results when there is a conflict between or among goals.

After reviewing the data in block 106 or block 108, the user decides at block 110 whether to accept the overall caloric distribution in the case of no conflict, or whether to adjust the overall caloric distribution in the case where there is a conflict. If a conflict exists and the user chooses not to adjust or correct the conflict, block 114 displays an inconsistent caloric distribution message, indicating that the caloric distribution is in conflict and that it must be resolved to create a nutritional profile for the subject.

If the user accepts the displayed caloric distribution goal, or chooses a caloric distribution goal that resolves previously conflicting goals, the program next generates additional nutritional goals. See FIG. 2, Block 116. This includes any goal other than the caloric distribution goal, such as minimum and maximum requirements for the following nutrients: arginine, cystine, histidine, isoleucine, leucine, lysine, methionine, phenylalanine, taurine, threonine, tryptophan, tyrosine, valine, arachidonic acid, docosahexaenoic acid (DHA), eicosapentaenoic acid (EPA), linoleic acid, linolenic acid, calcium, copper, chloride, chromium, iodine, iron, magnesium, manganese, phosphorus, potassium, selenium, sodium, zinc, vitamin A, vitamin D, vitamin E, vitamin K, biotin, choline, folic acid, niacin, pantothenic acid, pyridoxine, riboflavin, thiamine, vitamin B12 and vitamin C. The additional goals further include but are not limited to acceptable moisture content of food, acceptable fiber content of food, acceptable energy density of food, desired foods to comprise the subject's diet, foods/ingredients that the subject must avoid, acceptable viscosity, osmolarity, cost of the subject's diet, feeding volume limit(s) of the subject's diet, and acceptable subject feeding frequency.

Additionally at block 116, the program searches the generated goals for conflicts between or among them and summarizes them at block 118 and block 120. At block 118, a goal summary table is displayed where there is no conflict between or among goals; and in block 120, a goal summary table is displayed where there is a conflict between or among goals. After reviewing the data in block 118 or block 120, the user decides at block 122 whether to accept the overall goal summary in the case of no conflict, or whether to adjust the overall goal summary in the case where there is a conflict. If a conflict exists and the user chooses not to adjust or correct the conflict, block 124 displays an inconsistent goals message, indicating that the goals are in conflict and that they must be resolved in order to create a nutritional profile for the subject.

Block 126 shows the aspect of the program that generates the nutritional profile for the subject. See FIG. 2, block 126 and FIG. 3, block 202. Although the user has already selected which goals pertain to the subject, block 126 formally creates the complete nutritional profile that the program will use. The nutritional profile is saved.

The nutritional profile contains all of the nutritional requirements for a subject. For example, the aforementioned dog with renal insufficiency might be provided a low protein and low phosphorus requirement profile and additionally, the EPA, DHA, sodium and B-vitamin levels may be automatically adjusted to levels consistent with the goals of renal insufficiency because such levels are not in conflict with the levels required by a growing dog. The other essential nutrients that do not change during renal insufficiency are placed at a level consistent with a growing dog's requirement.

Block 128 shows a database containing nutritional profiles. The nutritional profile generated from block 126 may be saved in this database for future use. As shown in the connection from block 101 to block 130, the user may skip past blocks 102 through block 126 and immediately load a previously stored nutritional profile from the retrieval form shown at block 130. Regardless of whether the subject-specific nutritional profile is loaded using the retrieval form at block 130 or is generated from block 126 and placed in the database at 128, a user decision regarding diet type is required. See block 132. At block 132, the user may decide whether to export the nutritional profile to either the commercial diet selector, shown at block 200, the intravenous nutrition formulator, shown at block 300, or the Autobalancer, shown at block 400. Each of these modules will be described in detail.

Commercial Food Selector

Figure 3:
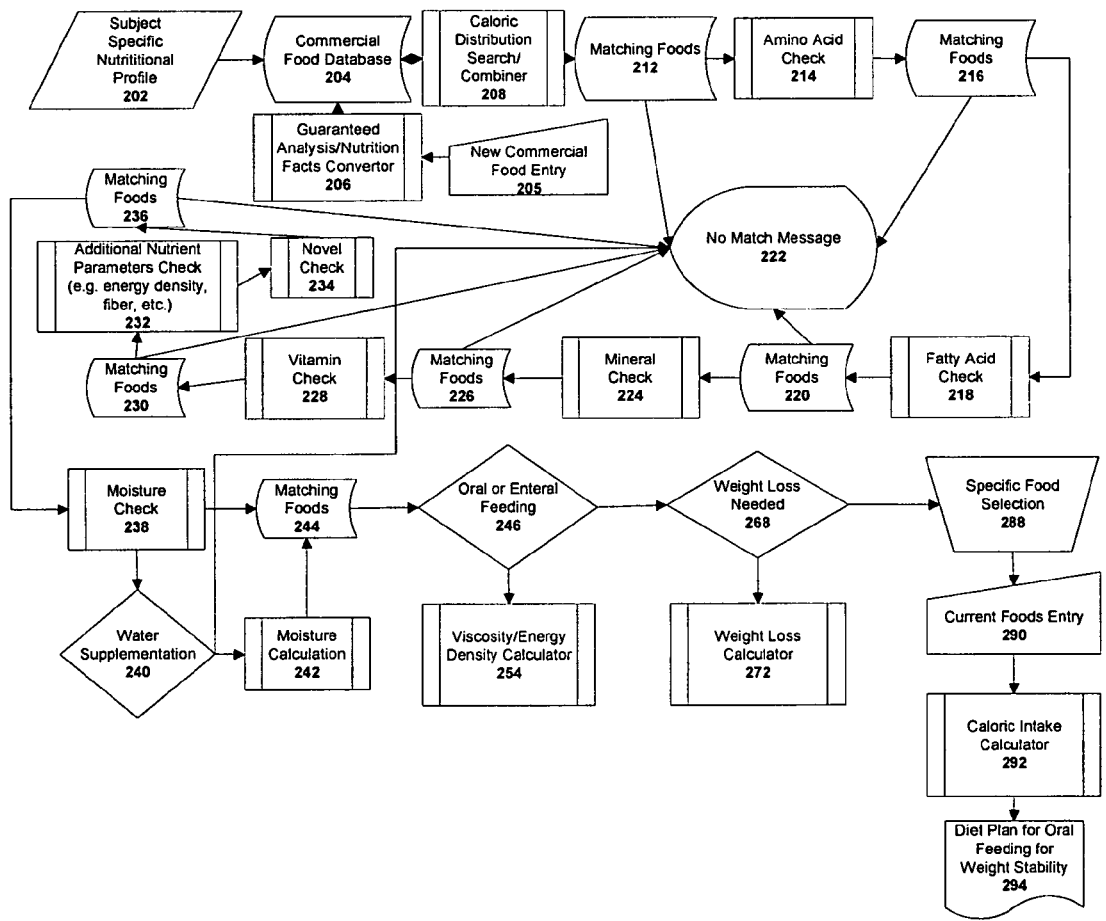
FIG. 3 is a flowchart of a Commercial Food Selector module according to an embodiment of the present invention.

This module, shown in detail in FIG. 3, allows a user to match commercial foods to a selected or created nutritional profile. The nutritional profile shown at block 202 and generated from the Nutritional Profile Generator (see FIG. 2) may be imported to the Commercial Food Selector.

Using foods from a commercial food database shown in block 204, the program finds all foods that meet the required caloric distribution from the nutritional profile. See block 208. By comparing all foods in the commercial food database and eliminating those that do not meet the required caloric distribution, the program in effect filters out all foods except those that meet the required caloric distribution.

A novel aspect of the Commercial Food Selector is its capability to find a combination of two foods that together meet the caloric distribution requirement. The Combiner module (Combiner) performs this advanced search at block 208.

For example, by using Combiner, a user could search the commercial food database to find a combination of two foods that provides both a low protein and low fat diet. The result may be a combination of a low protein but normal fat commercial food and a normal protein and low fat commercial food, that when consumed together, the combination caloric distribution of the two provides a diet having a caloric distribution both low in protein and low in fat.

To isolate food combinations that provide the required caloric distribution, the program examines every possible combination of two foods. For each combination, it stores the name of the two foods as DIET1 and DIET 2, respectively. The percentage of calories derived from protein in DIET1 is stored as DIET1PRO and the percentage of calories derived from protein in DIET2 is stored as DIET2PRO. Similarly, the percentage of calories derived from fat in DIET1 is stored as DIET1FAT and the percentage of calories derived from fat in DIET2 is stored as DIET2FAT. The three components of the required caloric distribution, protein, fat, and carbohydrate are stored as DESIREDPRO, DESIREDFAT, and DESIREDCHO, respectively.

If DIETLPRO<DESIREDPRO and DIET2PRO<or=DESIREDPRO, then this combination of foods is eliminated.

If DIETLPRO>DESIREDPRO and DIET2PRO>or=DESIRED PRO, then this combination of foods is eliminated.

If DIETLPRO=DESIREDPRO and DIET2PRO does not=DESIREDPRO, then this combination of foods is eliminated.

If DIET1FAT<DESIREDFAT and DIET2FAT<or=DESIREDFAT, then this combination of foods is eliminated.

If DIET1FAT>DESIREDFAT and DIET2FAT>or=DESIREDFAT, then this combination of foods is eliminated.

If DIET1FAT=DESIREDFAT and DIET2FAT does not=DESIREDFAT, then this combination of foods is eliminated.

If DIET1PRO=DESIREDPRO and DIET1FAT=DESIREDFAT, then this combination passes, and the name of the foods is immediately sent to the matching foods data file shown in block 212 along with information that the proportion of the two foods in this combination is 1:1.

If DIET1PRO=DESIREDPRO and DIET1FAT does not=DESIREDFAT, then the proportion needed of each is determined using the Pearson's Square method. See US Pat. Pub. 20020048606A1 (citing Ice Cream, K A Hyde and J Rothwell, Churchill Livingstone, 1973). If a proportion of DIET1 and DIET2 exists wherein DIET1PRO=DESIREDPRO and DIET1FAT=DESIREDFAT, then this proportion, along with the names of the foods, is sent to the matching foods data file shown in block 212.

If DIET1FAT=DESIREDFAT and DIET1PRO does not=DESIREDPRO, then a Pearson's Square is performed on the fat values. If a proportion of DIET1 and DIET2 exists wherein DIET1FAT=DESIREDFAT and DIET1PRO=DESIREDPRO, then this proportion, along with the names of the foods, is sent to the matching foods data file shown in block 212.

If DIET1PRO is not=DESIREDPRO and DIET1FAT is not=DESIREDFAT then the program determines an acceptable proportion using a Pearson's Square, and the percent of calories derived from fat is calculated using that proportion. If the percent of calories derived from fat is within a range bounded by DESIREDFAT−1% and DESIREDFAT+1%, then this combination of DIET1 and DIET2 and the proportion of each is sent to the matching foods data file shown in block 212.

The program applies the above filters for every possible combination of two foods from the food database.

Foods matching the required caloric distribution are stored in a temporary data file called matching foods. At FIG. 3 block 212 is the first iteration of the matching foods data file, and subsequent modified versions of the file are at blocks 216, 220, 226, 230, 236, and 244. With each subsequent filter the program applies to the matching foods file, the matching foods file gets smaller and smaller as the foods that do not match the nutritional profile are eliminated. After the final filter, only those foods matching the entire nutritional profile remain in the matching foods data file. See block 244. If during the process, the matching foods data file contains no foods matching the nutritional profile, block 222 is displayed, indicating that no foods match. For instance, if no foods from the commercial food database provide the required caloric distribution of the subject's nutritional profile, then the no match message of block 222 is displayed, notifying the user, and suggesting how to proceed. For example, block 222 may display a suggestion to feed the subject a home-prepared diet created using the applicant's Autobalancer module.

The commercial food database shown in block 204 is a database of many foods commercially available today. Data available for pet food includes guaranteed analysis, an ingredients list, and energy density, as well as company information about the maker of the foods. Guaranteed analysis is a required component for all commercial pet food labels in the United States, and must include the following: minimum percent crude protein as fed (% CP), minimum percent crude fat as fed (CF %), maximum percent moisture as fed (% H2O), and maximum percent fiber as fed (% Fib). Similar data in a different format exists for human foods in the Nutrition Facts panel on human food labels. At block 205 the user may enter guaranteed analysis or nutritional facts data for foods not available in the commercial food database at block 204. At block 206, the program converts the food information entered in block 205 to caloric distribution data so it may be utilized in the caloric distribution search shown in block 208.

To convert the commercial pet food information to caloric distribution data, the percent of nitrogen-free extracts (NFE) or carbohydrate on an as fed basis (% CHO) is determined by subtracting the provided guaranteed analysis information from 100% (when not provided), as shown by the formula (100%−(% CP+% CF+% H2O+% Fib))=% CHO. If the food label indicates the presence of ash in the food, the program may modify the equation accordingly. The % CP, % CF, and % CHO is then multiplied by the appropriate modified Atwater factor for protein, fat, and carbohydrate, such as 3.5 kilocalories (kcal)/g, 8.5 kcal/g, and 3.5 kcal/g, respectively. Atwater factors represent the energy values of different food materials. These three values are totaled and the proportion of the total each value contributes to the total is computed. Thus, if there are 140.0 kcal from protein, 124.1 kcal from fat, and 94.64 kcal from carbohydrate, then the total kcal amount is 358.7 kcal and the percentage from protein, fat and carbohydrate are 39.03%, 34.59%, and 26.38%, respectively.

Next, if the nutritional profile includes an amino acid goal, the program performs an amino acid check as shown in block 214. If the nutritional profile contains no amino acid goal, then the program may skip to the fatty acid check in block 218. To determine if they match the required amino acid profile of the nutritional goal, the program checks all foods remaining in the temporary matching foods file. The foods that match remain in the matching foods file shown in block 216. If no food remains in the matching foods file, then the program notifies the user by displaying the no match message of block 222.

Next, if the nutritional profile includes a fatty acid goal, the program performs a fatty acid check as shown in block 218. Here, the program identifies those foods remaining in the matching foods file that match the subject's fatty acid profile. Those foods that match the nutritional profile's required caloric distribution, amino acid and fatty acid profile are stored temporarily in the matching foods file shown at block 220. If the nutritional profile contains no fatty acid goal, then the program may skip to the mineral check shown in block 224. If no food remains in the matching foods file shown at block 220, then the program notifies the user by displaying the no match message of block 222.

Next, if the nutritional profile includes a mineral level goal, the program performs a mineral level check as shown in block 224. Here, the foods remaining in the matching foods file are searched to find those foods matching the mineral levels from the nutritional profile. Those foods that match the nutritional profile's required caloric distribution, amino acid, fatty acid and mineral level profile are stored temporarily in the matching foods file shown at block 226. If the nutritional profile contains no mineral level goal, then the program may skip to the vitamin check shown in block 228. If no food remains in the matching foods file shown at block 226, then the program notifies the user by displaying the no match message of block 222.

Next, if the nutritional profile includes a vitamin level goal, the program performs a vitamin level check as shown in block 228. Here, the foods remaining in the matching foods file are searched to find those foods matching the vitamin levels from the nutritional profile. Those foods that match the nutritional profile's required caloric distribution, amino acid, fatty acid, mineral, and vitamin level profile are stored temporarily in the matching foods file shown at block 230. If the nutritional profile contains no vitamin level goal, then the program may skip to the additional nutrient parameters check shown in block 232. If no food remains in the matching foods file shown at block 230, then the program notifies the user by displaying the no match message of block 222.

Next and as shown in block 232, the foods in the matching foods file are searched and those foods not matching any additional nutritional parameters from the nutritional profile are removed. If necessary, the program next performs a novelty check at block 234. This check would likely be used if the subject was diseased, allergic to certain foods, or for any other reason was to consume novel foods. If this additional check is needed, then the user is asked to complete a diet history form (if not previously performed), to determine ingredients that are still truly novel or new to the subject. Subsequent to this check, those foods that match the nutritional profile's required caloric distribution, amino acid, fatty acid, mineral, vitamin, and any other specified nutritional parameters from the nutritional profile, and that pass the novelty check if necessary, are stored in the matching foods file shown at block 236. The program removes from the matching foods file those foods that do not meet the additional nutritional parameters or that fail the novelty check. If no foods remain in the matching foods file shown at block 236, then the no match message from block 222 is displayed. The additional nutritional parameter check includes but is not limited to energy density and fiber content.

Next, the program performs a moisture check as shown in block 238. Here, the foods remaining in the matching foods file are searched for those foods matching the required moisture level determined from the nutritional profile. For instance, if during the input portion of the program, a canine subject was stated to have calcium oxalate urolithiasis, then at this block the program would send the urolithiasis information to a database that would reveal that the moisture content of the dog's diet must be 85%. (See block 102).

After the moisture check, the matching foods file shown at block 244 will now contain those foods that match the nutritional profile's required caloric distribution, amino acid profile, fatty acid profile, mineral content, vitamin content, additional nutritional parameters and moisture level. The program presents the user with a question at block 240 asking if water should be added to those foods failing only the moisture check. If the user selects that water should be added, the program performs a moisture calculation at block 242. This calculation determines the amount of water required by the moisture-deficient foods in order for them to meet the required moisture level from the nutritional profile. The algorithm underlying this moisture calculation is as follows: NW=((A*DM)−(A*PM))/1−DM, where NW is defined as the mass of the water in grams needed to achieve a desired moisture, PM is defined as the percent moisture of the food, DM is defined as the percent moisture desired, and A is defined as the mass of the food in grams. The program obtains the value for DM from any database known in the art providing a nutritional strategy for an animal. It may also have been previously saved by the user. These foods and the amount of moisture they require are added back to the list of matching foods shown at block 244. If the user decides that moisture will not be added, and no foods remain in the matching foods file with enough water without the addition of moisture, then no foods remain and the program displays the no match message at block 222.

The matching foods file at block 244 contains only those foods that passed all the previous checks. In one embodiment, the moisture check is the final check, but the program may also perform other checks, such as a purine content check, an oxalate content check, or a check to ensure carbohydrate sources fall within a certain glycemic index range. At block 246, the user must select whether the subject will consume the diet orally or through a feeding tube. If the user selects a feeding tube, then the program continues to the viscosity/energy density calculator module sown in FIGS. 1, 3 and 4 at block 254. If the user selects that the diet is to be fed orally, then the program continues to block 268.

Next, and as shown at block 268, the user selects whether the subject is in need of weight loss. If the user selects that weight loss is needed, then the program continues to block 272. If the user selects that no weight loss is needed, then the program continues to block 288.

Figure 4:
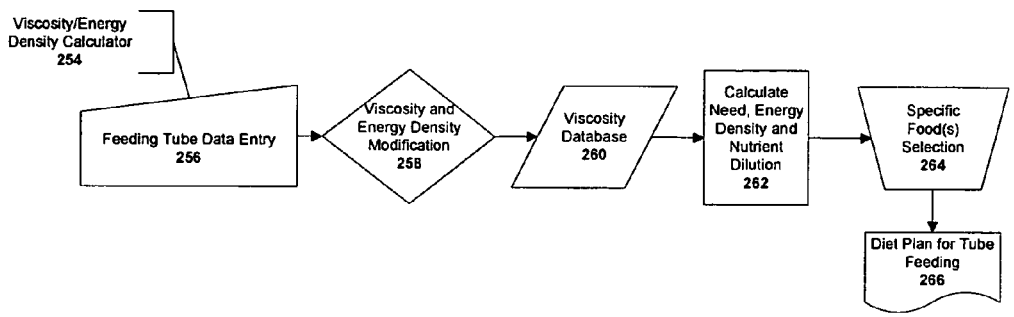
FIG. 4 is a flowchart of a Viscosity/Energy Density Calculator module according to an embodiment of the present invention.

Referring now to FIG. 4, the calculation of energy and viscosity is shown in detail starting at block 254. At block 256, the program requests an input from the user regarding information about subject's feeding tube. Such information includes but is not limited to the location of placement of the feeding tube (i.e., nasogastric, nasoesophageal, esophagostomy, gastrostomy, and jejunostomy), size (inside diameter and length), desired meal frequency, and desired single feeding volume limit(s). This information is temporarily stored.

Next, and as shown at block 258, the user decides whether the program should decrease viscosity and whether the program should increase energy density. If only a decreased viscosity is desired then the program will determine the amount of water to be added to the food. If decreased viscosity and increased energy density are desired then syrup and/or oil will be added to the diet. In order to calculate the amount of water, syrup, and/or oil that must be added to meet the user's specifications from block 258 and block 256, the program refers to a database at block 260. This database contains the minimal amount of added water, syrup, or oil that one would need to allow blended high moisture commercial food to pass through a variety of different sized tubes and tube types.

Using information from database 260, the program calculates the amount of water, syrup and/or oil that is needed to allow the selected high moisture commercial food to pass through the selected size and type of feeding tube. See block 262. Because moisture and/or energy is added, the energy density of the food is altered and the nutrients in the food are diluted. This process also calculates the degree to which energy density has been altered and the degree to which the nutrients in the food are diluted. For instance, the addition of water decreases the energy density of foods while the addition of syrup or oil generally increases the energy density. In addition, since syrup adds water and carbohydrate but no other nutrients, and oil adds only fat and no other nutrients, the nutrient levels of the original food is lessened as the nutrients are diluted by the addition of syrup and/or oil. In one example, if 2 grams of calcium was provided by 1 megacalorie (Mcal) of food prior to the addition of oil, and 1 Mcal of oil was added to 1 Mcal of food, then the calcium content of the oil-supplemented food would drop from the original 2 grams per Mcal to 1 gram per Mcal. The program makes these modifications to the foods remaining in the matching foods file from block 244. See FIG. 3.

The calculations at block 262 first require the user to select the tube size and type, meal frequency, and single feeding volume limits. Based on the selected tube size and type, the program retrieves an acceptable upper limit for viscosity. The upper limit may be based on a known viscosity of a water+Hill's a/d (Hill's Pet Nutrition, Inc., Topeka, Kans.) slurry, that is, the minimum amount of water needed to propel slurry through a selected tube when a force of 3 pounds is applied to a 60 milliliter syringe at 72-76 degrees Fahrenheit. The viscosity of the slurry created by the program is equal to (ds*ts*vw)/(dw*tw) where ds is the density of the slurry in g/ml, ts is the time in seconds for the slurry to run through a standard tube with a constant force at a constant temperature, vw is the viscosity of water, dw is the density of water in g/ml, and tw is the time for water to run through the same tube under the same conditions as the slurry was tested. Additionally, the software calculates the required energy density of the slurry as equal to (# of kcal per day)/[(# of feedings per day)* (volume limit in ml)].

The program then retrieves the proportion of water needed to create slurry with a viscosity equal to or less than the upper limit for viscosity based on a database of these proportions contained in the program. The program calculates the energy density of the slurry and compares it to the required energy density detailed above. The program calculates the energy density of the slurry according to the following formula: (kcal from water+kcal from canned food)/(ml from water+ml from canned food).

If the calculated energy density of the slurry is equal to the needed energy density calculated previously, then the program provides the slurry's proportions and amount to feed per day or per feeding to the user. If the energy density of the slurry is less than the needed energy density, then the program asks the user if sugar syrup or vegetable oil should be added to the canned food to increase the energy density of the product. The amount of oil or syrup to achieve the desired energy density will be calculated as x=(c−b)/(a−b), where x*100 is the percent of calories from syrup or oil needed, a is the syrup or oil energy density, b is the canned diet energy density, and c is the needed slurry energy density.

The effect on the overall caloric distribution is then determined and compared to the required caloric distribution. If the calculated caloric distribution is not within the required caloric distribution or distribution range, then the user will be asked if an increased feeding frequency, larger volume per feeding, or decreased daily caloric intake can be tolerated or is acceptable to allow the desired energy density to be reduced.

For example, the diet slurry of canned diet dog food and water created by the program may have a caloric distribution of 10% protein calories, 30% fat calories, and 60% carbohydrate calories, and an energy density of 0.8 kcal/ml. If, however, the desired energy density was 1.2 kcal/ml and sugar syrup (4 kcal/ml) was selected to increase the energy density, then 12.5% of the slurry's calories would need to come from the sugar syrup because ((1.2 kcal/ml−0.8 kcal/ml)/(4 kcal/ml−0.8 kcal/ml))*100=12.5%. Because water contributes no energy, 87.5% of the remaining calories would need to come from the canned food. Thus, the new percentage of calories coming from protein may be calculated using the amount from the food and the amount from the syrup. Since syrup has no protein, the new protein percentage is simply 87.5% of the original 10% protein calories needed, or 8.75%. If the nutritional profile required at least 9% protein calories, then the desired energy density would necessarily have to be reduced so that the amount of syrup added would subsequently be reduced. Alternatively, if the user decides to change the desired energy density, then the value of protein calories might become acceptable.

If the user changes the desired energy density, the program performs the procedure again starting with the addition of water and using the changed parameters. If the user chooses not to make changes, then the program uses the Combiner module where all canned foods with known or calculated viscosity are combined with syrup and/or oil to determine if a matching caloric distribution can be identified. If the program can identify a suitable combination then it will determine if the energy density of the potential slurries is equal to or greater than the desired value. Slurries with acceptable energy densities and appropriate caloric distributions will then be run through the commercial diet selector module to ensure that the slurry meets the other desired nutritional goals. If at that point no slurries match, then the program displays to the user that no commercial canned food in the database where viscosity is known can be made into a slurry to meet the subject's needs.

At block 264, the foods remaining in the temporary matching foods file from block 244 (see FIG. 3) as altered by the viscosity/energy density calculator are displayed to the user, and the user selects specifically which supplemented foods from the file will be fed to the subject. Finally, block 266 displays a report with the amount of food and amount of water, syrup, or oil to blenderize, as well as the energy density of the supplemented foods. The program also provides feeding volume and frequency as well as instructions on administration and monitoring.

Figure 5:
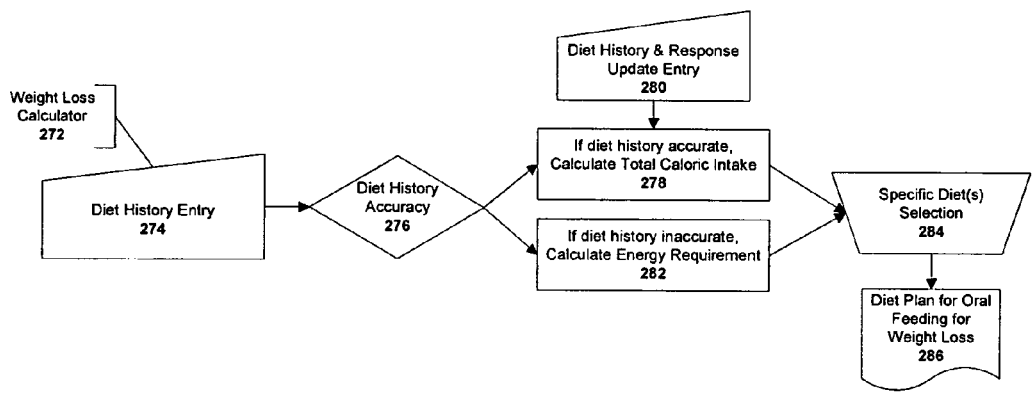
FIG. 5 is a flowchart of a Weight Loss Calculator module according to an embodiment of the present invention.

If at block 268 the user chose the weight loss option, the program continues as shown in FIG. 5, block 272. At the first step of the weight loss calculator, the user inputs the body weight history and diet history of the subject, as shown at block 274. Here, the user enters historical data about the subject's food intake at a time that the subject's body weight remained stable at the subject's current weight. The amount of kilocalories consumed is equal to the amount of kilocalories needed to maintain body weight, and is used as a basis for the initial caloric restriction. This caloric restriction may also be referred to as a weight loss goal. At block 276, the program asks the user whether the information at block 274 is accurate and complete. For animals, generally a veterinarian or veterinary technician will answer this question based on a clinical impression of the subject and the subject's background. Entries that result in caloric intake that are less than 50% of resting energy requirement (RER) at the patient's current weight will generate a warning message.

Figure 7:
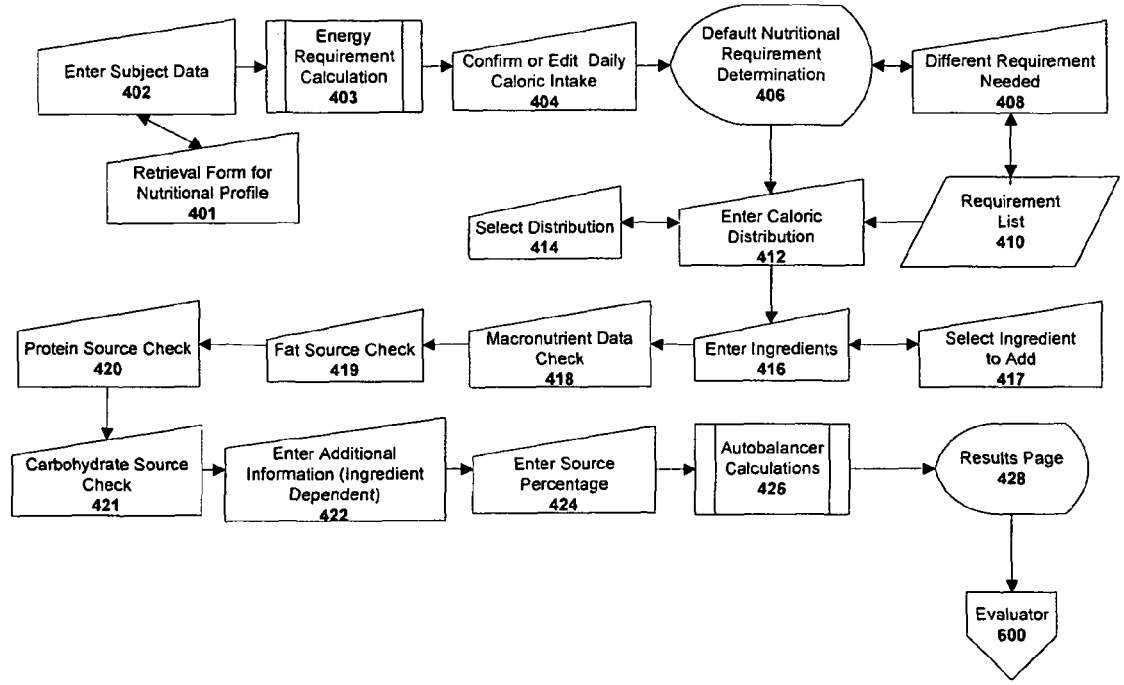
FIG. 7 is a flowchart of an Autobalancer module according to an embodiment of the present invention.

Blocks 278 and 282 show the process that calculates the optimum total caloric intake or energy requirement of the subject. If the diet history was determined to be accurate at block 276, then at block 278 the program calculates the subject's historic caloric intake using information from available food databases and recommends a caloric intake level generally consistent with the subject's weight loss goal, and that should initiate weight loss. If the diet history was identified as inaccurate, then at block 282 the program calculates the subject's energy requirement and uses this number as a basis for the initial recommendations for initiating weight loss. Although the program may use various methods in this calculation, typically, the RER for dogs is used, and 80% of the RER for cats is used. See block 403, FIG. 7. Over time and with subsequent treatments and analysis, the new results based on the recommendations from block 278 and 282 may be entered directly into block 280. That is, block 280 allows the user to enter new historical data about the subject's food intake in response to a previously instituted weight loss plan, thereby allowing block 278 to perform new calculations.

At block 284, the foods remaining in the temporary matching foods file from block 244 (see FIG. 3) are displayed. Here, the user selects specifically the foods from the matching foods file that will be fed to the subject. In one embodiment of the invention, the user may be given the option to also include treats in the subject's diet, where such treats are not a part of the matching foods file from block 244. As used herein, a treat or snack is defined as incomplete and unbalanced foods that are limited to less than 10% of a subject's daily caloric intake. Finally, block 286 displays a report with foods and the amount of each the subject should consume, as well as an expected rate of weight loss. The program may display goal weights during weight loss as well as initial recommendations on possible weight loss plan adjustments based on the subject's response. For example, if after following a customized diet plan, a subject is still gaining weight, the program may suggest an additional 25% reduction in caloric intake, or that compliance with the previous recommendation be reviewed. Other suggestions and recommendations known in the art may also be displayed.

If at block 268, the user selected that weight loss is not needed, then the program continues and at block 288, the foods remaining in the temporary matching foods file from block 244 are displayed to the user. See FIG. 3. Here, the user selects specifically which foods from the file will be fed to the subject. In one embodiment of the invention, the user may be given the option to also provide treats for the subject's diet, where such treats are not a part of the matching foods file from block 244. Next, at block 290, the program gives the user the option of inputting current foods consumed by the subject. The program uses this information in the process shown at block 292. Block 292 analyzes the foods entered in block 290 with the foods selected from block 288 and ensures that the new food(s) provide a comparable amount of calories. Alternatively, the current foods entry at block 290 may be left blank and the program will determine the amount of calories from the foods chosen in block 288 based on the subject's Maintenance Energy Requirement (MER) as shown in blocks 403 and 282.

Finally, at block 294, the program displays a report with feeding recommendations for the subject.

Intravenous Nutrition Calculator

Figure 6:
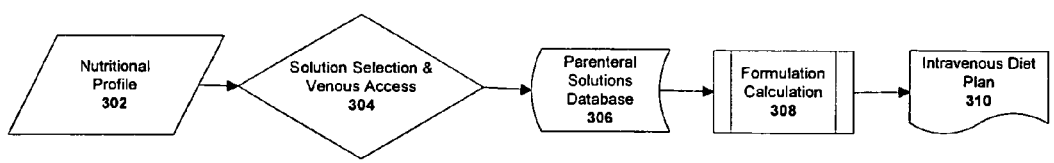
FIG. 6 is a flowchart of an Intravenous Nutrition Formulator module according to an embodiment of the present invention.

The intravenous nutrition calculator module uses the subject's nutritional profile (block 302, FIG. 6) to formulate an intravenous solution. See FIG. 2 block 300. Details for one embodiment of the intravenous nutrition calculator are shown in the flow chart in FIG. 6.

At block 304, the user first selects the brand and concentration of amino acid, lipid, and dextrose solutions to constitute a base for the solution formula, as well as the venous access point through which the user will administer the compounded solution.

Next, the program accesses the parenteral solutions database at block 306. This database contains data on the energy density (kcal/ml) and osmolarity (osmoles/L) of different parenteral solutions as well as other nutrient data, such as amino acid content, electrolyte profile, vitamin and trace mineral content of the parenteral solution. At block 308, the program then uses this information to calculate the formulation of the compounded solution.

Specifically, the calculations at block determine the volume of amino acid, lipid, and dextrose solution needed to meet the required caloric distribution of the subject's nutritional profile. The amount of calories from protein, fat, and carbohydrate are used to determine the volume of amino acid, lipid, and dextrose solution to use. For example, if 200 fat calories are needed and the lipid solution provides 2 kcal of fat per ml, then 100 ml of lipid solution will be needed. The program further calculates the electrolyte, vitamin, and trace mineral supplementation based on the nutritional profile, as well as the rate(s) of administration. The resulting compounded solution's energy density, osmolarity, electrolyte, vitamin, and trace mineral levels will be calculated and checked against any required limits. For example, if the solution is to be administered through a peripheral vessel than a safe upper limit of 650-700 mOsmol/L for osmolarity must not be exceeded. The program would check the solution's osmolarity to ensure it does not exceed the upper limit. As used herein, safe upper limit is defined as an amount of nutrient beyond which adverse health effects may occur.

As shown in block 310, the program displays an intravenous nutrition formulation based on the calculations from block 308.

Autobalancer

Autobalancer allows a user to select ingredients from the ingredient database for the program to use to create with nutrient amounts equal to or as close as possible to the nutritional requirements of a subject. See FIG. 7. In the embodiment of the invention shown in FIG. 7, applicant's program obtains the subject nutritional requirements from the subject's nutritional profile (block 302, see block 128) generated from the Nutritional Profile Generator. It may also use nutritional requirements data on the subject received within the Autobalancer module itself. These nutritional requirements may also be referred to as the nutritional goals of the subject.

The first step is shown at block 402. Here, the user inputs a subject nutritional profile into the program. The program will use this information to generate a recommendation of nutritional requirements for the subject. In one embodiment, the nutritional requirements consist of caloric distribution requirements. Alternatively, if the Nutritional Profile Generator module of applicant's software was used to create a subject nutritional profile, the nutritional profile may be imported into Autobalancer as shown in blocks 401 and 402. If the Nutritional Profile Generator module has not been used to create a subject nutritional profile, then the subject information is collected here, and includes but is not limited to subject name, body weight, height, age, species, sex, reproductive status, activity level, percent body fat and body condition score. This subject information makes up the nutritional profile that will be analyzed by the Autobalancer module.

The program first calculates the energy requirement of the subject as shown in block 403. Depending on the data entered or imported to block 402, different energy requirements may be calculated. For instance, for dogs and cats, the requirement is calculated as the MER and for humans the Harris-Benedict formula (see below) for Basal Metabolic Rate (BMR) is calculated and then multiplied by the subject's activity level. Other equations may also be used by the software to calculate the total daily caloric intake for the subject. Alternatively, the caloric intake may be determined from diet history as was shown in block 278. See FIG. 5.

The MER is calculated by multiplying the subject's RER× f, where RER=70×(ideal body weight in kg)$^{0.75}$, ideal body weight is calculated using the standardized body condition scoring (BCS) system, wherein each point above or below 5 is considered 10% over or underweight, and where f is a factor that varies according to the age, species and reproductive or sexual status of the dog or cat. Common values for f are shown in the following table:

| Subject Information | f |
| --- | --- |
| Intact male dog, >12 months old | 1.8 |
| Intact female dog, >12 months old, not expecting | 1.8 |
| Dogs <4 months old | 3.0 |
| Dogs 4-12 months old | 2.0 |
| Neutered male and female dogs, >12 months old | 1.6 |
| Pregnant female dog, first 42 days of gestation | 1.8 |
| Pregnant female dog, last 21 days of gestation | 3.0 |
| Nursing female dog, >12 months old | 8.0 |
| Intact male cat, >12 months old | 1.4 |
| Intact female cat, >12 months old, not expecting | 1.4 |
| Pregnant female cat, near conception | 1.6 |
| Pregnant female cat, near birth | 2.0 |
| Nursing female cat, >12 months old | 6.0 |
| Neutered male and female cats, >12 months old | 1.2 |
| Cats <12 months old | 2.5 |

The Harris-Benedict formula for BMR is calculated for men as follows:

$$BMR=66+(13.7\times(\text{body weight in kg}))+(5\times(\text{height in cm}))-(6.8\times(\text{age in years})).$$

The Harris-Benedict formula for BMR is calculated for women as follows:

$$BMR=655+(9.6\times(\text{body weight in kg}))+(1.8\times(\text{height in cm}))-(4.7\times(\text{age in years})).$$

The program multiples the calculated BMR by the following factors corresponding to the subject's activity level: sedentary (1.2), lightly active (1.375), moderately active (1.55), very active (1.725), extremely active (1.9), competitive training (2.0). Other embodiments of the invention may use equations different from those presented here, particularly when calculating the energy requirement for animals other than dogs, cats, or humans.

Based on the nutritional profile from block 402 and the calculations from block 403, a recommended total daily caloric intake is displayed for the user as shown in block 404. The user may either accept or modify this value. For instance, the program may derive large batch formulations by multiplying the daily total caloric intake by the number of days the user would like the batch to last. Although in a preferred embodiment the program displays the results in kcal, the program may also display the results in kiloJoules.

After user approval of the total caloric intake as shown in block 404, the program determines the default nutritional requirements for the subject as shown in block 406. Here, the program obtains nutritional requirements for the subject from a database of guidelines. For instance, the Association of American Feed Control Officials (AAFCO) publishes requirements that may be used for dogs and cats and the United States Department of Agriculture (USDA) publishes requirements that may be used for humans. Other guidelines published by these or other institutions currently and in the future may also be used with the current invention. Alternatively, a user created requirement, a different existing requirement, or the nutritional profile generated from the Nutritional Profile Generator module could be used. At block 408, the user may choose to use a different set of requirements. If the user chose different requirements, then at block 410, the program provides for the user a list of alternative requirements that may be selected. When the user is ready to move to the next step, the nutritional requirements in block 406 are confirmed and the program advances to block 412.

At block 412, the user may either enter the selected caloric distribution (percent of calories from protein, fat and carbohydrate) for the subject, or as shown in block 414, import the caloric distribution values from the subject's current diet. These values may be imported from other modules of applicant's software, such as the Diet Evaluator, the Nutritional Profile Generator, or the Sorter.

After the caloric distribution is accepted, the user enters the food choices, or ingredients, that the user would like to include in the subject's diet. The user may enter these foods directly at block 416, or may choose the foods from an ingredient list as shown in block 417. Block 417 also allows the user to import a list of food choices from the Diet Evaluator module of applicants program, from the nutritional profile generated in the Nutritional Profile Generator module, or from the Sorter module.

For each possible food choice, the nutritional content of the food choice is provided for either automatically by the database of foods, or manually by the user. The program performs a check at 418 to ensure that such data is provided for every selected food choice. In one embodiment, the program uses Atwater factors to calculate the caloric distribution of the different food choices. The program will display ingredients that do not have Atwater factors in the database. The user will be asked to select values or alternatively the program may use known values based on species and chosen foods.

Optional checks that the program may make are shown at blocks 419, 420 and 421. At block 419, the program performs a check to verify that the user has selected a fat source, and if the user has not done so, the program asks the user to select a fat source. If a fat source is not provided, or the user wants the software to select the fat source(s), the program will add fats/oils to the diet based on the selected requirement(s) for essential fatty acids(s) and desired fatty acid ratio(s). The program will use the fat source(s) with the greatest concentration of the needed fatty acid(s).

At block 420, the program performs a check to verify that the user has selected a protein source, and if the user has not done so, the program will request that the user select a protein source. At block 421, the program performs a check to verify that the user has selected a carbohydrate source, and if the user has not done so, the program will request that the user select a carbohydrate source.

In order to complete the checks detailed above and shown in blocks 418, 419 and 420, the software automatically identifies and labels ingredients as a major source of one of either macronutrients (e.g. protein, fat, or carbohydrate source), snack/treat, complete and balanced diet, incomplete and unbalanced diet, or supplement. In one embodiment of the invention, a carbohydrate source is defined as any source having greater than or equal to 60% of its calories from carbohydrate, a protein source is defined as any source having greater than or equal to 30% of its calories from protein and less than 60% of its calories from carbohydrate calories, and a fat source is defined as any source having greater than or equal to 80% of its calories from fat. If none of these conditions is met, the program does not identify the ingredient as a major source of a macronutrient and it classifies the ingredient as a snack or treat. It remains classified as a snack or treat unless the food database identifies the ingredient as a complete and balanced diet, an incomplete and unbalanced diet, or a supplement. If identified as a complete and balanced diet, an incomplete and unbalanced diet, or a supplement, then that identification becomes the ingredient's classification. If the ingredient is classified as a complete and balanced diet or an incomplete and unbalanced diet then the program requests the amount of calories to come from the diet(s) or amount of the diet(s) to be added to the subject's overall diet, as is shown in block 422.

Block 424 provides the user with some final options before it begins the Autobalancer calculations. First, if the user selects more than one source for protein, fat, and/or carbohydrate, then the program asks the user to select the amount of calories to come from each source. In one embodiment of the invention, block 424 also allows the user to change the classification of an ingredient. For example, the database may classify bacon as a fat source and the user may wish to instead classify it as a protein source. In another embodiment of the invention, block 424 will also allow a user to request that a certain volume or common amount (i.e. cup, tablespoon) of an ingredient be met first if possible and then the remainder be met with other sources. For example, the user could select that the program first use 1 cup of rice as a carbohydrate source (the program calculates the amount of calories this represents), and then if additional carbohydrate is needed, that the program use potato. Block 424 also allows the user to set what percent of the daily caloric intake that is to come from treats or snacks. Finally, at block 424, the user may select the amount of calories that are to come from complete and balanced diet(s), incomplete and unbalanced diet(s), and snack(s)/treat(s).

Block 426 contains the calculations performed by the Autobalancer in order to output a complete and balanced diet. The Autobalancer first calculates the calories from protein, fat, and carbohydrate for each ingredient and the percent of calories from protein, fat and carbohydrate for the protein source(s), fat source(s), and carbohydrate source(s). To accomplish this, for each ingredient, the program multiplies the selected Atwater factor by the number of grams of macronutrient per 100 grams of ingredient, resulting in the number of calories obtained from protein, fat, and carbohydrate. Next, the program totals the amount of calories from each macronutrient and determines the percent of calories from each macronutrient to give the percent of calories from protein, fat, and carbohydrate for each source. Next, the caloric distribution for the net protein source (all ingredients classified as a protein source in their desired proportions) is calculated. The contribution of all protein sources contribution to the net caloric distribution is calculated based on the amount of calories coming from each protein source. For example, if chicken and beef are both selected as protein sources, and chicken has 45% protein calories and beef has 75% protein calories and the user selects that calories coming from both chicken and beef are equal, then the percent of protein calories is (45%×50%)+(75%×50%)=60% protein calories from the net protein source. The program repeats this process for fat calories and carbohydrate calories to generate the caloric distribution for the net protein source. This procedure is then performed for the net fat source and net carbohydrate source.

The above procedure generates the following nine values:

| Variable | Description |
| --- | --- |
| $pp | % protein calories from net protein source |
| $pf | % fat calories from net protein source |
| $pc | % carbohydrates from net protein source |
| $fp | % protein calories from net fat source |
| $ff | % fat calories from net fat source |

-continued

| Variable | Description |
| --- | --- |
| $fc | % carbohydrate calories from net fat source |
| $cp | % protein calories from net carbohydrate source |
| $cf | % fat calories from net carbohydrate source |
| $cc | % carbohydrate calories from net carbohydrate source |

Next, the total amount of kilocalories from the complete and balanced diet ingredient(s), incomplete and unbalanced diet ingredient(s), and treat(s)/snack(s) are calculated. The program subtracts the total amount of kilocalories from these sources from the total daily caloric intake, giving a value representing the total kilocalories needed. The program multiplies the total daily caloric intake by the required caloric distribution for the diet to generate the amount of calories to come from protein, fat, and carbohydrate.

Next, the amount of calories from protein, fat, and carbohydrate from the complete and balanced diet ingredient(s), incomplete and unbalanced diet ingredient(s), and treat(s)/snack(s) are calculated such that when subtracted from the amount of calories from protein, fat and carbohydrate that are required in total, the Autobalanced diet will contain the required percentage of protein, fat or carbohydrate calories. Thus, if the diet and treats have a higher than desired percentage of calories from fat then an Autobalanced diet will be created that has a lower than desired percentage of fat calories so that when combined, the overall diet will have the desired percentage of fat calorie content, if possible.

The following equations, using the values listed from the table above, and where $ik=desired total kcal, $ip=desired percentage of protein calories, $if=desired percentage of fat calories and $ic=desired percentage of carbohydrate calories, detail how the Autobalancer arrives at its three figures, $p (kcal provided by net protein source), $f (kcal provided by net fat source), and $c (kcal provided by net carbohydrate source):

$$\$xn=\$ik*((\$pp*\$if)-(\$ip*\$pf));$$

$$\$xd=(\$pp*\$ff)-(\$pf*\$fp); \text{ where } \$xd \text{ does not equal zero.}$$

$$\$x=\$xn/\$xd;$$

$$\$yn=(\$pp*\$cf)-)(pf*\$cp);$$

$$\$yd=(\$pp*\$ff)-(\$pf*\$fp); \text{ where } \$yd \text{ does not equal zero}$$

$$\$cn=(\$ik*\$pp*\$ic)-((\$ik*\$ip*\$pc)-((\$x*\$pp*\$fc)+(\$x*\$pc*\$fp)));$$

$$\$cd=(\$pp*\$cc)-((\$pc*\$cp)-((\$y*\$pp*\$fc)+(\$y*\$pc*\$fp))); \text{ where } \$cd \text{ does not equal zero}$$

$$\$c=\$cn/\$cd;$$

$$\$f=\$x-(\$c*\$y);$$

$$\$p=\$ik-(\$f+\$c).$$

If one of the values ($c, $f, $p) determined by Autobalancer is negative, then the desired total calories and caloric distribution cannot be met with the selected ingredients.

The program then determines if the nutritional requirement includes a desired fatty acid ratio. If a specific fatty acid ratio is required and is already provided by the selected foods, then the program moves on. If the specific fatty acid requirement is not met by the diet, then the software determines the minimum amount of the fat source and the corresponding amount of fat calories that are needed to meet the requirement. The excess amount of fat calories, if present, is calculated and stored for later use.

The program next determines if the food combination's fatty acid ratio is greater or less than the desired fatty acid ratio.

If the food combination's fatty acid ratio is greater than the desired ratio then the program creates a list of all fat sources in the database with a fatty acid ratio lower than the desired ratio. The fat source with the lowest ratio is used, and if more than one is lowest then the program asks the user to select a preferred source from a list of those with the lowest ratio. The program then adds the new fat source in the same amount as the excess fat calories previously stored, thus adding the new fat source in the maximum amount without changing the caloric distribution or creating an essential fatty acid deficiency. If no excess exists, the program asks the user if the user would like to select a different fat source(s), percentage of fat calories or desired fatty acid ratio. If the user does not change any of these then the desired fatty acid ratio cannot be met. The program recalculates the ratio following the addition of a new fat source and determines if the ratio can be lowered to be either equal to or lower than the desired ratio. If the ratio is equal to the desired ratio, then the program continues as before with the previous fat source and new fat source combination. If the ratio is lower, then the program determines the amount of the previous fat source and new fat source that is necessary to create the desired ratio. If the desired ratio cannot be met, and thus there are no fats that can be added within the confines of the amount of excess fat calories, then the user can select to use the fat source(s) with the greatest concentration(s) of the required fatty acid(s) in the ingredient database, and the computer will once again attempt to match the fatty acid ratio with the desired ratio. If the user decides not to select a fat source with a higher concentration(s) of the fatty acid(s), or if after doing so the computer is still unsuccessful in meeting the desired ratio, then the user will be informed that the desired ratio is not possible with either the selected foods or with the chosen percentage of fat calories.

If the food combination's fatty acid ratio is less than the desired ratio, then the program creates a list of all fat sources in the database with a fatty acid ratio higher than the desired ratio. The fat source with the highest ratio is used, and if more than one is highest then the program asks the user to select a preferred source from a list of those with the highest ratio. It then adds in an amount equal to the excess fat calories previously stored, thus adding the new fat source in the maximum amount without changing the caloric distribution or creating an essential fatty acid deficiency. If no excess exists, the program asks the user if the user would like to select a different fat source(s), different percentage of fat calories, or different desired fatty acid ratio. If the user does not change any of these then the desired fatty acid ratio cannot be met. The program recalculates the ratio following the addition of a new fat source and determines if the ratio can be raised to be either equal or higher than the desired ratio. If the ratio is equal to the desired ratio, then the program continues as before with the previous fat source and new fat source combination. If the ratio is higher, then the program determines the amount of the previous fat source and new fat source that is necessary to create the desired ratio. If the desired ratio cannot be met, and thus there are no fats that can be added within the confines of the amount of excess fat calories, then the user can select to use the fat source(s) with the greatest concentration(s) of the required fatty acid(s) in the ingredient database, and the computer will once again attempt to match the fatty acid ratio with the desired ratio. If the user decides not to select a fat source with a higher concentration(s) of the fatty acid(s), or if after doing so the computer is still unsuccessful in meeting the desired ratio, then the user will be informed that the desired ratio is not possible with either the selected foods or with the chosen percentage of fat calories.

Next, the Autobalancer calculates the amount of calories and the gram amount for each selected ingredient. For example, the program calculates the number of kilocalories from each protein source that makes up the net protein source by multiplying the total kilocalories from the net protein source ($p) by the user-selected percent of calories from that specific protein source. Dividing the calories from each individual protein source by the calories per gram of that source (constant for the same Atwater factor) provides the gram amount for each protein source. The program follows the same procedure for the fat and carbohydrate sources to generate the calories and the gram amount to come from each fat and carbohydrate source.

Next, the program totals the amount of calories from each protein, fat, and carbohydrate source and divides that total by the gram amount of dry matter. This in turn is multiplied by 1000 to give the total kcal/kg dry matter.

For dogs, if an AAFCO requirement (or a similar guideline that also uses energy density to determine which specific requirement to use) was chosen and the kcals/kg are less than 3500, then the requirement on a dry matter basis is used. If an AAFCO requirement was chosen and the kcal/kg dry matter is greater than or equal to 3500, then the requirement on an energy basis is used. At 3500 kcal/kg, the requirement on an energy basis equals the requirement on a dry matter basis.

For cats, if an AAFCO requirement (or a similar guideline that also uses energy density to determine which specific requirement to use) was chosen and the kcals/kg are less than 4000, then the requirement on a dry matter basis is used. If an AAFCO requirement was chosen and the kcal/kg dry matter is greater than or equal to 4000, then the requirement on an energy basis is used. At 4000 kcal/kg, the requirement on an energy basis equals the requirement on a dry matter basis.

The amount of nutrient provided by the gram amount of each protein, fat, and carbohydrate source is determined by multiplying the amount of nutrient per 100 g of the protein, fat, or carbohydrate source by the gram amount of the protein, fat or carbohydrate source. The program then divides the product by 100, which provides the amount of nutrient per source. The amount of nutrient from each of the protein, fat, and carbohydrate sources is totaled to give the total amount of nutrient from all sources.

For dogs and cats, the total amount of each nutrient is divided by the total grams of dry matter and multiplied by 1000 if the requirement is based on dry matter. If the requirement is based on calorie content, then the total amount of each nutrient is divided by the total kilocalories and multiplied by 1000. Thus, the program evaluates nutrient amounts on an amount per kg dry matter basis or an amount per Mcal basis. For humans, the total amount of each nutrient is used for evaluations.

If a calcium-to-phosphorus ratio is required, then the program calculates this ratio by dividing the total amount of calcium by the total amount of phosphorus. For dogs and cats, the vitamin E minimum requirement is adjusted by the total polyunsaturated fatty acid content to ensure adequate levels. The choline minimum requirement is also adjusted in reference to the methionine content of the diet to ensure adequate methyl donors in the diet.

The program compares protein level in the diet against the minimum and maximum requirements for crude protein. If the amount of crude protein in the diet is less than the minimum or more than the maximum requirement(s), then the diet fails.

The program then compares the amino acid level(s) in the diet against the minimum and maximum requirement(s) for amino acid(s). If the level(s) in the diet is/are less than the minimum or more than the maximum requirement(s), then the diet fails.

The program then compares the amount of linoleic acid against the minimum and maximum requirements for linoleic acid. If the amount of linoleic acid in the diet is less than the minimum or more than the maximum requirements, then the diet fails.

The program then compares the amount of arachidonic acid against the minimum and maximum requirements for arachidonic acid. If the amount of arachidonic acid in the diet is less than the minimum or more than the maximum requirements, then the diet fails.

Any remaining essential fatty acid level(s) in the diet is/are checked against the minimum and maximum requirement(s). If the level(s) in the diet is/are less than the minimum or more than the maximum requirement(s), then the diet fails.

The total nutrient amount from the protein, fat, and carbohydrate sources are compared to the maximum requirement for each nutrient. If the amount is greater than the maximum requirement for any nutrient, then unless there is no maximum requirement, the diet fails.

In one embodiment of the invention, when the AAFCO requirements are used, the amount of Vitamin E needed by the subject varies with the amount of polyunsaturated fatty acids consumed by the subject. For every gram of the following fatty acids, a subsequent amount of Vitamin E, shown in the parentheses following the fatty acid, is required: Oleic acid (0.09 mg), gamma-linolenic acid (0.09 mg), dihomo-gamma-linolenic (0.09 mg), arachidonic acid (1.20 mg), eicosapentaenoic acid (1.50 mg), and docosahexaenoic acid (1.80 mg). The total amount of Vitamin E needed is thus determined. If this value is greater than the selected Vitamin E requirement, then it is used instead. This step is important because it is possible that a diet will be created with such a high amount of polyunsaturated fatty acids, that the amount of Vitamin E provided for in any of the current guidelines will be too little. Thus, the customizable nature of this program recognizes and compensates for this situation.

In one embodiment of the invention, choline is a nutrient required by the subject. The amount of choline needed is adjusted by the amount of excess methionine in the diet. The amount of methionine in excess of the minimum requirement is determined and this value is used to adjust the choline requirement (3.75 g methionine=1 g choline).

The amount of a nutrient that is needed is simply the amount required minus the amount present in the diet.

If the user selected a specific complete vitamin-mineral supplement with or without amino acid(s), then this supplement is added in sufficient quantity as to meet the required level of the nutrient with the greatest need. For example, if a diet contains 0.1 gram of calcium and 1 gram of phosphorus per Mcal and the subject requires 2.1 grams of calcium and 1.05 grams of phosphorus per Mcal and the user selects a supplement that provides 1 gram of calcium and 0.1 gram of phosphorus per 10 grams of supplement, then 20 grams of supplement will be added to the diet. In other embodiments, the program may add multiple supplements to the diet to meet nutrient requirements. Following the addition of the supplement(s), the program compares the amount of nutrient in the overall diet to the selected/adjusted requirements and/or checked against the minimum and maximum requirements. Diets meeting the minimum requirements and not exceeding the maximum requirements are complete and balanced and are reported back to the user as such at block 428.

If the supplement selected by the user does not contain copper and the subject requires copper in its diet, then the program may separately calculate the amount of copper needed to complete the diet. In one embodiment, the amount of copper is calculated in 0.0625 mg increments, allowing portions of a copper supplement to be provided to the subject.

Returning to FIG. 7, block 428 is a results page displayed to the user. A program displays a summary of the selected input as well as the amount of each ingredient as well as specific information regarding whether and why the diet failed. In one embodiment of the invention, the program allows for the reporting of the amount of each ingredient in common household measures such as cups, tablespoons, ounces, etc. In another embodiment of the invention, the program generates a user friendly report that may be used in daily preparation or batch preparation of the Autobalanced diet and may include preparation instructions. The report may also report separately the amount of copper. If supplement was added to the diet, the amount of supplement will also be displayed.

At block 428, the created diet may be sent to the Diet Evaluator module shown at block 600. See FIGS. 1 and 7).

Autoloader for Autobalancer

Figure 8:
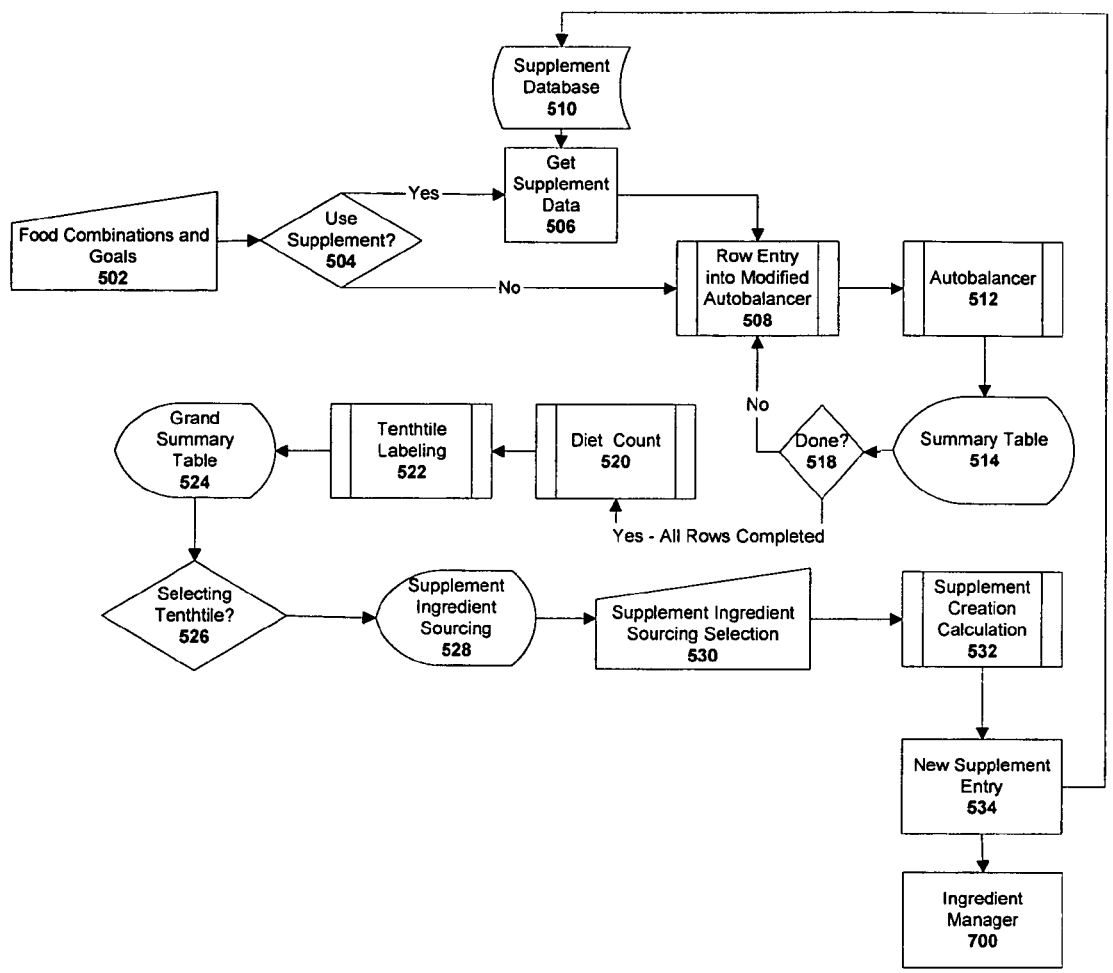
FIG. 8 is a flowchart of an Autoloader for Autobalancer module according to an embodiment of the present invention.

This module of the applicant's program loads a selection of ingredients with differing caloric distributions, requirements, and total calories into the Autobalancer. For each possible combination of those ingredients, the Autoloader module determines a diet's nutritional deficiencies by determining which nutrients are deficient and the extent of the deficiency. That is, the program uses the nutritional parameters from various foods, determines every possible diet comprising those foods, and designs a supplement that allows the highest number of those diets to have sufficient but not excessive amounts of every nutrient. By testing every possible combination of food that meets a required caloric distribution range and required amount of total calories, the program may calculate the extent to which each diet is deficient or excessive for each particular nutrient and the amount of each nutrient that may be added to each diet without causing the diet to be excessive for that nutrient. The flow chart in FIG. 8 shows details for one embodiment of the Autoloader for Autobalancer.

Block 502 shows the first step taken by the Autoloader for Autobalancer module. In one embodiment of the invention, this step uses a tab-delimited data file containing ingredients that are to compose the subject's diet, but other means of inputting the information may be possible. The data consist of at least one combination of at least three foods. The program identifies at least one food as a protein source, at least one as a fat source, and at least one as a carbohydrate source. These sources are classified according to the procedure described supra regarding the Autobalancer module of this invention. The Atwater factors to use for each food are either entered by the user or obtained from a database.

In a preferred embodiment, the data file contains the following fields for every ingredient:

| Name of Field | Description |
| --- | --- |
| Ingredient ID number | A number assigned to each ingredient that will allow the database to access information about that ingredient |
| Abbreviated Name | Common name of the ingredient |
| Source Type | Either "protein", "fat", or "carbohydrate" if the ingredient is primarily a protein, fat, or carbohydrate, respectively |
| Source % | Percent of the calories from the net protein, fat or carbohydrate source from the specified ingredient |
| Protein Factor | The Atwater factor for the protein |
| Fat Factor | The Atwater factor for the fat |
| CHO Factor | The Atwater factor for the carbohydrate |

In addition, the data file may contain other information including a total number of kilocalories for the diet, a requirement based on an energy basis, and a requirement based on a dry matter basis. Both requirements may be obtained from a requirement database, such as the AAFCO or USDA requirements. Finally, a range for percent of calories to come from two macronutrients is entered. The program may calculate the amount of the third macronutrient by subtracting the percentage of the other two macronutrients from 100%. In one embodiment of the invention, the user enters the percentage of calories coming from protein, the range for the percent of calories to come from fat, and the size of the steps to use for caloric distributions within those ranges. For example, if 20-25% is the range, and the size of the step is 1, then the program would load the values 20, 21, 22, 23, 24, and 25. The following values are present and apply to the entire data file.

| Name of Field | Description |
| --- | --- |
| Kcal | Desired kcal per day |
| Requirement on a Mcal Basis | Database ID of the requirement based on calorie content to use |
| Requirement on a kg DM basis | Database ID of the requirement based on dry matter to use |
| % ME P | Range of desired percentage of ME (metabolizable energy) to be derived from Protein (ex, "25-35") |
| % ME F | Range of desired percentage of ME to be derived from Fat (ex, "20-42") |
| Step | The size in percent of the ME increment to use (ex, if range is 25%–35% and step is 5, then levels of 25%, 30% and 35% will be used) |

The data file contains as many unique combinations of ingredients as the user wishes to enter, and for each unique combination, the program will examine the combination once for every possible caloric distribution in the range selected by the user. For instance, the program may examine salmon and rice where 25% of the subject's calories are derived from protein and 25% are from carbohydrate. Next, the program may examine the same salmon and rice, but where 26% of the subject's calories are derived from carbohydrate. The program may continue in this fashion ultimately leading to hundreds or thousands of combinations of salmon and rice.

At block 504, the program presents the user with the option of adding a supplement to the diets. If this option is chosen, a supplement addition screen represented by block 506 is used wherein the supplement ingredients may be imported from a supplement database represented by block 510. Additionally, the user's decision as to whether or not to add a supplement is stored for later use by the program.

After the addition of the supplement, or if no supplement is added, at block 508 the program prepares the data for entry into a modified version of the Autobalancer module of the invention. For each combination of foods, the program analyzes the Atwater factors, total kilocalories, and requirements for every possible caloric distribution within the range selected by the user. Thus, the same combination of foods may be analyzed hundreds or thousands of times but in varying proportions. After completing analysis of every potential caloric distribution for a combination of foods, the Autobalancer next examines every potential caloric distribution for the next combination of foods.

The analysis performed by the modified Autobalancer is identical to the analysis performed by the Autobalancer module discussed supra with the exception that the Autobalancer calculations at block 426 do not consider amino acid levels if a supplement was not added to the diet. See FIG. 7.

Block 512 represents the modified Autobalancer used by the Autoloader for Autobalancer module. The program runs through all of the checks discussed supra in the Autobalancer portion of this specification if a supplement had been added at block 504, and all of the checks except the amino acid check if a supplement was not added at block 504. For each combination of foods from the data file, the program runs the modified Autobalancer as many times as necessary to test every possible caloric distribution of the combination of foods. For each specific diet that passes all the required checks, the program calculates the extent that the specific diet is deficient or excessive for each particular nutrient. In other words, Autobalancer determines the numerical difference between the amount of a required nutrient in each version of the food combination and the minimum amount of that nutrient the subject requires. This numerical difference is stored.

A summary table at block 514 displays the results obtained by the Autobalancer during the analysis of every version of a food combination. This table lists the smallest and greatest amount of each nutrient any one diet within the group needed in order to provide the minimum nutritional level for the subject. The program also displays the minimum requirement for each nutrient. For instance, if salmon and rice were used, and the program analyzed four hundred different caloric distributions of salmon and rice for calcium content, then the range of calcium displayed in the table would span from the least amount required by any one of the four hundred diets to the most amount required by any one of the four hundred diets. The summary table may list other statistics from the previous calculation, including the total number of diets checked, the number of those that passed all checks, and the number of diets that failed the vitamin-mineral check.

Block 518 allows the program to either repeat blocks 508-514 for a different combination of foods, or if there are no more combinations of foods in the data file to analyze, to move to block 520 for the diet count. For instance, if there are 10 combinations of foods in the data file, then blocks 508-514 will occur once for each of those 10 combinations of foods.

After completing its analysis of every caloric distribution for every combination of food, blocks 520 and 522 represent a further analysis of the data displayed in block 514. Using data from every diet analyzed, the program generates a total range of deficiencies, spanning from the single diet that required the most nutrient to meet the subject's minimum requirement, to the single diet that required the least nutrient to meet the subject's minimum requirement. See block 520. The lower value for this range is the smallest difference between the amount of nutrient the diet provided and the amount of nutrient the subject requires (the smallest nutritional deficiency), while the larger value is the largest difference between the amount of the nutrient the diet provided and the amount of nutrient the subject requires (the highest nutritional deficiency).

At block 522 this range is broken down into 10 equal segments hereinafter referred to as "tenthtiles." The program totals the number of diets having a difference that falls within a specific tenthtile. Thus, the higher tenthtiles (requiring the addition of the largest amount of nutrient) will generally contain no diets with a sufficient amount of the nutrient, and the lowest tenthtile (requiring the addition of the least amount of nutrient) will generally contain many diets providing a sufficient amount of a nutrient, even without the addition of a supplement.

If supplement was not added, block 522 determines the difference between the amount of each nutrient in the diet and the maximum requirement or safe upper limit. This difference is referred to herein as the safety margin. The program counts how many diets have a safety margin that falls within the range represented by the tenthtile for each nutrient. Thus, the number of diets that would exceed the maximum requirement with the addition of a supplement containing the amount of nutrient within the tenthtile can be determined. The total number of diets that meet the requirement with the addition of the amount of nutrient within the tenthtile minus the total number of diets that would exceed the safe upper limit with the addition of the amount of nutrient within the tenthtile provides the total number of diets that would meet the minimum requirement but yet not exceed the safe upper limit. The tenthtile that provides the greatest number of diets with nutrient levels that meet the minimum and do not exceed the safe upper limit is the optimum tenthtile. The total range across all tenthtiles is the range between the lowest and highest tenthtile where at least one diet meets the minimum requirement and does not exceed the safe upper limit.

The following example illustrates the process occurring at block 522 where supplement was not added.

| Iodine (mg) |
| --- |
| [0.0479 < x <= 0.1284] |
| 260 − 0 = 260 |
| [0.1284 < x <= 0.2090] |
| 2728 − 0 = 2728 |
| [0.2090 < x <= 0.2895] |
| 9048 − 0 = 9048 |
| [0.2895 < x <= 0.3701] |
| 14319 − 0 = 14319 |
| [0.3701 < x <= 0.4506] |
| 44849 − 0 = 44849 |
| [0.4506 < x <= 0.5312] |
| 47434 − 0 = 47434 |
| [0.5312 < x <= 0.6117] |
| 48753 − 0 = 48753 |
| [0.6117 < x <= 0.6922] |
| 48783 − 5 = 48778 Optimum |
| [0.6922 < x <= 0.7728] |
| 48848 − 1539 = 47309 |
| [0.7728 < x <= 0.8533] |
| 48934 − 8515 = 40419 |

The above example table shows the results from one nutrient (iodine) that passed the checks in the modified Autobalancer in 48,934 different possible diets. At the lowest tenthtile, adding between 0.0479 and 0.1284 mg of iodine would cause 260 diets to meet the minimum requirement for iodine. The number of diets that would exceed the safe upper limit (zero) at this level is subtracted from this value yielding a total of 260 diets that would meet the minimum and not exceed the safe upper limit if between 0.0479 and 0.1284 mg of iodine were added. The optimum range (hereinafter referred to as the optimum tenthtile), between 0.6117 and 0.6922 mg, is labeled as such because adding the amount in the optimum range allows 48,783 of the diets to meet the minimum requirement, while only 5 exceed the safe upper limit, yielding a total of 48,778 diets within the range.

If a maximum requirement does not exist, then the highest tenthtile will also be the optimum tenthtile since the most number of diets will meet the minimum requirement, and none will be in excess of the safe upper limit.

If more than one tenthtile are the optimum tenthtile, then the optimum range is a range that encompasses all the values for all of the optimum tenthtiles. The process occurring in block 522 and outlined above for iodine occurs once for every nutrient one would like to analyze. Thus, the values for a supplement consist of only the optimum amount of each nutrient.

In block 522, if a supplement had been added, the program determines the total number of food combinations that would not meet the minimum requirement and that exceed the safe upper limit for each nutrient. A grand summary table at block 524 when a supplement is not added, displays the total number of diets that did not meet the minimum requirement for the nutrient and the total number of diets that exceeded the safe upper limit. If a supplement was not added, block 522 is the final block for the Autoloader for Autobalancer module.

A user may wish to use the Autoloader for Autobalancer in combination with a newly created supplement in order to learn how many of the diets passed and failed with the addition of the supplement. In a sample scenario, the Autobalancer examined 92,664 diets, and of those, 51,706 passed the checks prior to the amino acid, vitamin and mineral checks. Of those diets passing the preliminary checks, 40,035 were completed and balanced with the addition of the newly created supplement, or roughly 77% of the possible diets.

One would expect not all of the 92,664 diets to pass the checks and get to the point in the process where the effects of the addition of the supplement could be analyzed. This is because many food choices either cannot be combined to provide a predetermined caloric distribution, have an amount of crude protein and essential fatty acid(s) below the minimum requirement even when the required caloric distribution has been met, or provide an excessive amount of a nutrient or nutrients that exceed the safe upper limit for the subject. Therefore, viable food combinations are only those that meet the required caloric distribution, crude protein and essential fatty acid(s) minimum requirements, and that do not exceed the maximum requirement for any nutrient.

Of the 51,706 viable food combinations that passed the preliminary checks in the sample scenario, the supplement was not able to complete and balance all of them. This failure may be due to a diet nutritional deficiency uncorrectable by the supplement. For example, a few food combinations may need an amino acid not present in the supplement. The failure may also be due to excess in a nutrient provided by the supplement as a side effect of the addition of the supplement in an amount needed to meet the minimum requirement of another nutrient. For example, if the subject needs 5 grams of supplement to meet the requirement for calcium, this amount of supplement might concurrently provide an excess of a second nutrient, bringing the total amount of that second nutrient to a level in excess of the safe upper limit.

If in block 504, the user did not add a supplement, block 524 provides for the user a display showing the results of the tenthtile labeling occurring at block 522.

At block 526, the user may select a tenthtile for each nutrient to be used as a basis for the creation of a supplement. Selecting the optimum tenthtile results in the selection of the range for the nutrient that when added to a diet, results in the meeting of the requirement for the most number of diets while exceeding the safe upper limit as few times as possible. Upon user selection, the range is averaged and sent to block 528.

At block 528, the program displays a list of possible sources for the nutrients that will comprise the supplement. Often times in practice, there exists more than one source for each nutrient one wishes to add (i.e., calcium carbonate, calcium gluconate, and calcium citrate can each provide calcium). At block 530, the user may select which ingredient in the database to use to supply each desired nutrient.

At block 532, based on the tenthtile and the ingredients selected, the supplement formulation is calculated. Although the tenthtiles in block 522 include a range of nutrient needed, in practice the average of the range is used to make the supplement. The sourcing calculations are critical because in practice some ingredients provide one nutrient but also contain other nutrients, while others provide two nutrients, and still others provide and contain only one nutrient. This, as well as the purity of the ingredients must be taken into account by the program.

To complete the sourcing calculations, first the amount of methionine and cystine needed, if a combined methionine-cystine requirement exists, is calculated. The amount of methionine needed is equal to the amount of methionine needed (if an additional separate requirement is listed) plus one half of the amount of methionine-cystine needed. The amount of cystine needed is equal to one half of the amount of methionine-cystine needed. Next, if a combined phenylalanine-tyrosine requirement exists, the amount of phenylalanine and tyrosine is calculated. The amount of phenylalanine needed is equal to the amount of phenylalanine needed (if an additional separate requirement is listed) plus one half of the amount of phenylalanine-tyrosine needed. The amount of tyrosine needed is equal to one half of the amount of phenylalanine-tyrosine needed.

Next, the program divides supplement ingredients (e.g. calcium carbonate, sodium selenite, L-lysine, etc.) into three groups. Ingredients that were selected to meet only the value of one nutrient but that contain at least one additional nutrient are labeled "Singles (2+ nutrients)." Ingredients that supply only one nutrient are grouped under "Singles (1 nutrient)." Ingredients that are selected to meet more than one nutrient are grouped under "Multiples." For the ingredients grouped in "Singles (2+ nutrients)," the amount of ingredient needed to meet the nutrient value it was selected to provide is added. The amount of the additional nutrient(s) provided by the addition of that ingredient is then subtracted from the amount of nutrient that is needed. Next, the amount of "Singles (1 nutrient)" is added in sufficient quantities to meet the needed nutrient value it was selected to provide. For the supplement ingredients that provide more than one needed nutrient ("Multiples"), the nutrient with the greater need for the supplement ingredient is determined and added.

Next, the total mass of all the ingredient sources (in the amounts needed) is determined (taking source ingredient purity into account), then the total amount of each nutrient from all ingredient sources is determined. This is necessary since more of a nutrient may have been added than is needed. For example, if potassium chloride and sodium chloride are selected to provide the needed potassium and sodium, respectively, more chloride than is needed could be added to the supplement.

Block 534 shows that the supplement ingredients and amounts may be imported to the Ingredient Manager module of the program. The program or user may also import this information to the supplement database, as seen in block 510. By exporting the supplement ingredients to either of these components of the program, the user may test the supplement on the same diets used to create it, thus ensuring that the supplement actually allows the majority of the diets to be completed and balanced. The supplement may then be tested on other diets as well.

Diet Evaluator

The Diet Evaluator is a program that compiles different ingredients and compares the combined nutritional profile of those ingredients with a selected requirement. This module relates to the claimed invention in that the diet from block 428 (see FIG. 7) in the Autobalancer may be sent here for further evaluation of specific nutrients, such as reviewing the contribution of different ingredients to the overall nutritional profile.

In order to use the Diet Evaluator module, the user must first select a requirement, such as the AAFCO or USDA requirements or a user created requirement. After the user selects a requirement, the program displays a field from which the user may select ingredients to compare to the requirement. If the amount of energy from the ingredients must be determined, the program may assign Atwater factors or the user may input them. For humans, the requirements may be on a "per day basis" or similar. For each diet sent to the Diet Evaluator from the Autobalancer module, the Diet Evaluator displays a list of nutrients, as well as whether the requirement for each has been met or exceeded.

The Diet Evaluator (see FIG. 1 block 600) may also be used manually, wherein the user first selects which requirement guideline they wish to use, and then selects an ingredient, or an entire diet, as well as the quantity of either. The program evaluates that ingredient or diet to determine whether it meets the requirements set forth by the chosen guideline. Optionally, a user may select the Atwater factor to use when calculating the energy content of ingredients.

In one embodiment, the results display consists of colored bars. Green bars indicate that the minimum requirement has been met without exceeding the safe upper limit; red bars indicate that the minimum has not been met, and yellow bars indicate that the minimum has been met, but that the safe upper limit has also been exceeded. The length of the red bar may correspond to the percent of the requirement present in the selected foods. The program may also display the total amount of nutrient contained in the food, as well as further data on specific nutrient levels beyond the percent of the requirement present and total amount of nutrient. In addition, other information displayed may include fatty acid and calcium to phosphorus ratios, grams of dry matter, percentage of moisture, calculated anion-cation balance, and other possibilities.

Ingredient Manager

The Ingredient Manager (see FIG. 1 block 700), is used in the process of balancing a diet, creating a supplement and by the commercial diet selector module. The Ingredient Manager module is software that enables the user to view, retrieve, enter, and edit data in the ingredient database that contains foods, recipes/diets, and supplements. The ingredients in the Ingredient Manager may be compiled from any number of sources, and in one embodiment were compiled from the USDA National Nutrient Database. Other sources include McCance and Widdowson's The Composition of Foods Sixth Edition, and laboratory food testing results from such laboratories as Woodson-Tenant Laboratories, Division of Eurofins Scientific Inc.

All ingredients in the Ingredient Manager module have a unique ID and name. Many ingredients have Atwater factors and a nitrogen factor used for the calculation of protein content. Each entry also has general information, such as the source(s) of the data, user access level, original entry date, name of user who made the entry, type of ingredient, etc. Standard conversions such as 1 cup=237 grams, 1 pouch=85 grams and 1 tablespoon=14.2 grams may be used, depending on the individual ingredient's bulk density. All ingredients have a list of nutrients they contain when comprised of more than 1 ingredient, and the amount of nutrient per 100 grams of the ingredient.

The Ingredient Manager also enables a user to search for an ingredient entry. To retrieve the entry, the user may enter the full name or part of the name for the ingredient, or the specific ID number corresponding to the ingredient. Partial name entries will retrieve all matching entries. For example, if the user enters "oats" as a desired food, then the program will retrieve and display all entries containing the word "oats." The user may then select the specific form of oats to be used in the subject's diet.

If a food is not listed in the Ingredient Manager, a user may enter the food and its attributes, and the program will assign the food a new ID number. If the attributes for a given food change, the user may update the database.

Sorter

A Sorter module may be used in cooperation with the Ingredient Manger module. This Sorter (see FIG. 1 block 800) allows a user to sort a list of foods by selected nutritional information, and compare selected nutritional information between or among ingredients. A novel aspect of the Sorter module is the ability it gives the user to find foods that substantially comply with two separate dietary requirements of a subject. For example, if a subject requires a high amount of protein and a low amount of phosphorus, the Sorter module can sort all available foods for those that meet both of these requirements.

In one embodiment, the user inputs a number of diets or ingredients similar to the method disclosed supra. The user then selects a group size, which is the number of diets or ingredients the program will place into each group. The user next selects a nutrient and whether the foods or ingredients should be sorted in ascending or descending order of amounts for that food or ingredient. If as in the above example, the user selected to have the diets and ingredients sorted first in descending order of protein level, and further selected a group size of 10, the program would place the ten diets with the highest level of protein into group 1. Group 2 would similarly consist of the next ten diets with the $11^{th}$ through the $20^{th}$ highest protein levels, and so on until all foods and ingredients were placed in a group.

If as in the above example, the user further required a low amount of phosphorus, the program can then perform a second sort within each group in ascending amounts of phosphorus. Thus, the user can identify the diet with one of the highest protein levels that also has the lowest phosphorus level. In existing sorters used for sorting nutrients, the phosphorus levels of those diets with the same amount of protein would only be sorted when the amount of protein in those diets was exactly the same. Since repeated identical values for nutrients in foods are extremely rare, these sorters are of little practical use.

After both sorts are complete, a summary table may be generated that lists ideal foods having an amount of nutrient close to the amount required by the user. From here, the user can again modify the degree of closeness. For instance, if the list is too large to be useful, the user may narrow the goal to a more specific amount. The summary table can also generate the minimum, maximum, and average amounts of each said nutrient amount wherein the minimum amount is the lowest amount of nutrient among the foods, the maximum is the highest amount of nutrient among the foods, and the average is the average value of each nutrient among all foods.

The sorting and comparing functions of the Ingredient Manager module may assist a medical professional in deciding which foods to enter into the Autobalancer or Autoloader for Autobalancer modules of this program. The nutritional information from the Sorter may also assist the user of the Autoloader for Autobalancer in the creation of a new supplement. For instance, a user could choose to make a supplement using a nutritional requirement based off the minimum or maximum values for all diets that were sorted.

Requirement Manager

The Requirement Manager module (see FIG. 1 block 900), is used by the various modules of applicant's program. This software allows the user to view, retrieve, enter and edit data in a database of nutritional requirements for any species of animal, especially cats and dogs.

The requirements in the Requirement Manager may be compiled from any number of sources, and in one embodiment were compiled from the AAFCO Official Publication.

In another embodiment, a user may enter the requirements on an amount per kilogram of dry matter basis, an amount per megacalorie basis, or an amount per day. The user may also create additional or new requirements.

All requirements have a unique ID, name, type (that is, whether based on kilogram dry matter, calorie content, etc.), target (the species the requirement pertains to), and a per unit value. Requirements also have caloric distribution values, type of factors used, and other miscellaneous information (such as the original source of the requirement, original entry date, the range of energy density that the requirement may be used for, etc.). Lastly, all requirements have a list of nutrients with a minimum and maximum amount including but not limited to amount per kilogram dry matter, amount per megacalorie or amount per day. The maximum amount is the safe upper limit. To indicate that no maximum amount exists, a zero value may be entered by default.

The module may also provide a search function for the user. Here, the user enters the full name or part of the name for the requirement or the specific ID number, and the entry is retrieved. Partial name entries will retrieve all matching entries. The user may also view all existing requirements, edit any of the existing requirements, or create new requirements.

Supplement Description

The following supplement ranges were created utilizing the Autoloader for Autobalancer procedure described supra. It is noted that the actual supplement ingredients providing the disclosed range of nutritional values may vary depending on their source. For example, calcium carbonate may be used as a source to provide the required amount of calcium, or if calcium carbonate is unavailable, the calcium may be provided by calcium gluconate as well. In either case, the amount of calcium in the supplement will fall within the disclosed range.

Because the various sources used to create the supplement will have different purities of each nutrient, an amount of the nutrient cannot be given by itself, and thus the amounts are given in relation to each other. Thus, fractions or multiples of the amounts listed are claimed as long as the divider or multiplier is constant for all nutrients listed. Furthermore, formulations are provided in the average amount needed for 1 Mcal of food consumed by the subject.

Although the customizable nature of the program allows the creation of any number of different supplements for a variety of different animals, the following describes an embodiment of the program used to create supplements for cats and dogs. As used herein, supplement can include any nutritional supplement, capsule, powder, food, liquid, or any other product comprising a definite amount of nutrient or nutrient per unit supplement that is administered to a subject.

Canine Universal

To formulate the canine universal supplement, any current guidelines detailing the dietary needs of dogs may be used. In one embodiment, the nutritional requirements were based on several leading publications of dietary requirement guidelines, including the current official publication of AAFCO and the Nutrient Requirements of Dogs and Cats by the National Research Council (NRC) of the National Academies. In a separate embodiment, the safe upper limit for a nutrient from the NRC guidelines was ignored because of controversy in the veterinary nutrition industry over whether the NRC set the safe upper limit too low. Specifically, the iodine maximum in one embodiment was increased from the NRC value, the linoleic acid safe upper limit was not used, and the requirement for chromium was removed. Using more than one set of guidelines was not necessary, but doing so allowed for the formulation of a supplement containing a broader range of nutrients and applications. In practice, any guideline may be used with the program to formulate a supplement and in one embodiment, the amount of vitamin E required was set to a value higher than recommended by either the AAFCO or NRC guideline.

The foods entered into the Autoloader for Autobalancer were the human foods most commonly fed to canines, and included the protein sources 2% fat cottage cheese, beef, chicken, chicken egg, lamb, pork, and salmon, and the carbohydrate sources barley, brown rice, couscous, oats, potato, spaghetti, sweet potato, tapioca, and white rice. Although eight protein sources and nine carbohydrate sources were used, any number of other foods may be inputted into the program in place of or in addition to those listed here. The choice to use the most common foods in this embodiment ensures the supplement will have the broadest possible range of applications.

The metabolizable energy for the above sources was set at 3.5 kcal/g protein, 8.5 kcal/g fat, and 3.5 kcal/g carbohydrate. This specification does not preclude using different values for metabolizable energy.

represents data derived from the optimum tenthtile produced by the program. The "best min," "best max," and "best avg" represent respectively, the low end, the high end, and the mean of the optimum tenthtile. The "low" is the smallest amount of nutrient that any particular diet required, and the "high" is the largest amount of nutrient that any particular diet required. As used herein, mcg indicates micrograms, IU indicates international units, and mcg_RAE indicates micrograms of retinol activity equivalents and mcg_DFE means micrograms dietary folate equivalents. For this and subsequent tables indicating the formula of a canine supplement by weight of the nutrients contained therein, amounts are given per 1000 kilocalories (1 Mcal) food consumed. That is, for every 1 Mcal of food consumed by the canine subject, an amount of nutrient listed in the table should be administered.

| nutrient | unit/Mcal | low | best min | best avg | best max | high |
| --- | --- | --- | --- | --- | --- | --- |
| Chloride | g | 0 | 0.2002 | 0.21135 | 0.2225 | 0.2225 |
| Tryptophan | g | 0 | 0.1735 | 0.1831 | 0.1927 | 0.1927 |
| Vitamin D | IU | 0 | 128.7 | 135.85 | 143 | 143 |
| Selenium, Se | mcg | 0 | 13.9286 | 44.70245 | 75.4763 | 75.4763 |
| Vitamin B-12 | mcg | 0 | 5.3406 | 7.1373 | 8.934 | 8.934 |
| Vitamin K | mcg | 194.0551 | 244.3876 | 247.1838 | 249.98 | 249.98 |
| Folate | mcg_DFE | 0 | 40.697 | 51.70795 | 62.7189 | 62.7189 |
| Vitamin A | mcg_RAE | 0 | 385.83 | 407.265 | 428.7 | 428.7 |
| Calcium, Ca | mg | 920.1865 | 1590.8399 | 1628.0984 | 1665.3569 | 1665.3569 |
| Copper, Cu | mg | 0.1458 | 1.8393 | 1.93335 | 2.0274 | 2.0274 |
| Iodine | mg | 0.1128 | 0.3968 | 0.4126 | 0.4284 | 0.4284 |
| Iron, Fe | mg | 8.5241 | 20.3576 | 21.015 | 21.6724 | 21.6724 |
| Magnesium, Mg | mg | 0 | 78.0628 | 102.3996 | 126.7364 | 126.7364 |
| Manganese, Mn | mg | 0 | 1.26 | 1.33 | 1.4 | 1.4 |
| Niacin | mg | 0 | 2.7357 | 3.1127 | 3.4897 | 3.4897 |
| Pantothenic acid | mg | 0 | 1.7224 | 2.2431 | 2.7638 | 2.7638 |
| Phosphorus, P | mg | 0 | 965.1485 | 1018.76785 | 1072.3872 | 1072.3872 |
| Potassium, K | mg | 0 | 1221.0949 | 1288.9335 | 1356.7721 | 1356.7721 |
| Riboflavin | mg | 0 | 0.3984 | 0.7555 | 1.1126 | 1.1126 |
| Sodium, Na | mg | 0 | 124.3584 | 131.2672 | 138.176 | 138.176 |
| Thiamine | mg | 0 | 0.1841 | 0.32935 | 0.4746 | 0.4746 |
| Total Choline | mg | 0 | 256.245 | 313.0371 | 369.8292 | 369.8292 |
| Vitamin B-6 | mg | 0 | 0.076 | 0.0802 | 0.0844 | 0.0844 |
| Vitamin E | mg | 3.0927 | 35.0998 | 57.37435 | 79.6489 | 79.6489 |
| Zinc, Zn | mg | 6.5451 | 29.7494 | 31.0385 | 32.3276 | 32.3276 |

The food combinations detailed above were then combined with a high linoleic acid containing vegetable oil. The proportion of each of the three foods making up the combination varied depending on the particular caloric distribution being analyzed by the Autobalancer module at the time. Caloric distributions of 18-50% protein, 12-50% fat (and by subtraction from 100%, 0-70% carbohydrate), were used at 1% increments.

The formulations in the following table were obtained from running the Autoloader for Autobalancer. The amount shown The supplement formula may also be described in terms of the percentage contribution of mass each nutrient provides to the total mass of all the nutrients. In these calculations, for each nutrient, 50% of the difference between the "low" and the "high" is added to or subtracted from the "best avg" value, thus creating the "% low" and "% high" values shown in the table below. In the table below, the "best % low", "best % avg", and "best % high" represent the same amount of nutrient they represented in the previous table, but in percentage form. Thus, the following table shows that calcium contributes between 27.9% and 44.5% of the total mass of all the nutrients.

| | % low | best % low | best % avg | best % high | % high |
| --- | --- | --- | --- | --- | --- |
| Chloride | 3.547907006 | 4.205479157 | 4.229250221 | 4.255986399 | 4.497234263 |
| Tryptophan | 3.074734593 | 3.642228465 | 3.663949446 | 3.688379821 | 3.895697814 |
| Vitamin D | 5.70199E-05 | 6.75712E-05 | 6.79612E-05 | 6.83998E-05 | 7.22645E-05 |
| Selenium, Se | 0.00024684 | 0.000296104 | 0.000894525 | 0.00142658 | 0.00142658 |
| Vitamin B-12 | 9.46451E-05 | 0.000113534 | 0.000142822 | 0.000168862 | 0.000168862 |
| Vitamin K | 0.003835701 | 0.004724879 | 0.004946308 | 0.005195356 | 0.00777 |
| Folate | 0.000721225 | 0.000865164 | 0.00103471 | 0.001185452 | 0.001185452 |
| Vitamin A | 0.006837607 | 0.008102872 | 0.008149636 | 0.008202234 | 0.00866568 |
| Calcium, Ca | 27.89070934 | 31.47696059 | 32.57930219 | 33.81914574 | 44.49994084 |

|  | % low | best % low | best % avg | best % high | % high |
| --- | --- | --- | --- | --- | --- |
| Copper, Cu | 0.035179571 | 0.038319948 | 0.038687584 | 0.039101078 | 0.040067346 |
| Iodine | 0.007951712 | 0.008097201 | 0.008256393 | 0.008435442 | 0.009031036 |
| Iron, Fe | 0.384609022 | 0.409630681 | 0.420523744 | 0.432775568 | 0.511836093 |
| Magnesium, Mg | 1.383414361 | 1.659511564 | 2.049082238 | 2.395448488 | 2.395448488 |
| Manganese, Mn | 0.022329485 | 0.026461442 | 0.02661416 | 0.026785928 | 0.028299397 |
| Niacin | 0.048481564 | 0.058157353 | 0.062287141 | 0.065958924 | 0.067717112 |
| Pantothenic acid | 0.030524051 | 0.036615939 | 0.044885882 | 0.052238666 | 0.052238666 |
| Phosphorus, P | 17.10418144 | 20.26922255 | 20.38620371 | 20.51777667 | 21.6770797 |
| Potassium, K | 21.64001574 | 25.64439005 | 25.79239314 | 25.95885757 | 27.42559481 |
| Riboflavin | 0.00706037 | 0.008469455 | 0.015118044 | 0.021029286 | 0.021029286 |
| Sodium, Na | 2.203856337 | 2.61166871 | 2.626741588 | 2.6436946 | 2.793069653 |
| Thiamine | 0.003262586 | 0.003913722 | 0.006590507 | 0.008970429 | 0.008970429 |
| Total Choline | 4.541126028 | 5.447428745 | 6.264074873 | 6.990152773 | 6.990152773 |
| Vitamin B-6 | 0.001346858 | 0.001595247 | 0.001604854 | 0.001615659 | 0.001706328 |
| Vitamin E | 0.676840351 | 0.746175182 | 1.148097859 | 1.505446242 | 1.505446242 |
| Zinc, Zn | 0.611024935 | 0.611024935 | 0.621100464 | 0.632432776 | 0.64320435 |

To reduce the high cost associated with including amino acids, in an alternative embodiment of the invention, the supplement contains no amino acids. In this embodiment, the percentage of total mass contributed by each nutrient is as follows:

|  | % low | best % low | best % avg | best % high | % high |
| --- | --- | --- | --- | --- | --- |
| Chloride | 3.660456323 | 4.364442109 | 4.390101314 | 4.41897498 | 4.679534797 |
| Vitamin D | 5.88288E-05 | 7.01253E-05 | 7.05459E-05 | 7.10192E-05 | 7.51939E-05 |
| Selenium, Se | 0.00025467 | 0.000307443 | 0.000928546 | 0.001480503 | 0.001480503 |
| Vitamin B-12 | 9.76475E-05 | 0.000117882 | 0.000148254 | 0.000175245 | 0.000175245 |
| Vitamin K | 0.003991186 | 0.004903475 | 0.005134431 | 0.005394319 | 0.008016485 |
| Folate | 0.000744104 | 0.000898297 | 0.001074063 | 0.001230261 | 0.001230261 |
| Vitamin A | 0.007054515 | 0.008409152 | 0.008459591 | 0.008516349 | 0.009016953 |
| Calcium, Ca | 29.02129115 | 32.66675857 | 33.81839094 | 35.11429428 | 45.91160071 |
| Copper, Cu | 0.036295564 | 0.039768404 | 0.040158989 | 0.040598505 | 0.041691522 |
| Iodine | 0.008274044 | 0.008403267 | 0.008570408 | 0.008758488 | 0.009317525 |
| Iron, Fe | 0.400199589 | 0.425114315 | 0.436517526 | 0.449349276 | 0.528072934 |
| Magnesium, Mg | 1.427300049 | 1.723064736 | 2.127014992 | 2.485994072 | 2.485994072 |
| Manganese, Mn | 0.023037837 | 0.027461658 | 0.027626377 | 0.027811731 | 0.029446546 |
| Niacin | 0.050019532 | 0.060384565 | 0.064656108 | 0.068452106 | 0.070462102 |
| Pantothenic acid | 0.031492357 | 0.038018194 | 0.046593027 | 0.054213236 | 0.054213236 |
| Phosphorus, P | 17.64677287 | 21.03537912 | 21.16155229 | 21.30353184 | 22.55578492 |
| Potassium, K | 22.32649624 | 26.61372263 | 26.77335534 | 26.95298607 | 28.53732267 |
| Riboflavin | 0.007284345 | 0.008793804 | 0.015693028 | 0.021824172 | 0.021824172 |
| Sodium, Na | 2.273768689 | 2.710387204 | 2.726644463 | 2.744938353 | 2.906289926 |
| Thiamine | 0.003366084 | 0.004063603 | 0.006841163 | 0.009309502 | 0.009309502 |
| Total Choline | 4.685182969 | 5.656045174 | 6.502316461 | 7.254373635 | 7.254373635 |
| Vitamin B-6 | 0.001389584 | 0.001655546 | 0.001665891 | 0.001677533 | 0.001775496 |
| Vitamin E | 0.698311579 | 0.774750939 | 1.19176347 | 1.562350621 | 1.562350621 |
| Zinc, Zn | 0.634121073 | 0.634121073 | 0.64472278 | 0.656652619 | 0.663608551 |

Publication for AAFCO, or if no upper limit for the nutrient is published, (b) 50 times the high value for the nutrient in the optimum tenthtile as determined using Autoloader for Autobalancer. In yet another embodiment, the amino acid tryptophan is excluded in order to reduce production costs.

Although a supplement having amounts of nutrients within the optimum tenthtile will complete and balance the diet of many canines, it is expected that the program may be used to create a supplement for a vast range of diets. Thus, the following table represents a wider range of possible supplement formulations that may result. The "low" for all nutrients on this table is zero because it is expected that certain diet combinations will provide the daily requirement for each nutrient listed. The "high" is either (a) 50% of the current nutrient upper limit (on an energy basis) as published in the Official

| Nutrient | units/Mcal | lower limit | upper limit |
| --- | --- | --- | --- |
| Chloride | g | 0 | 11.125 |
| Tryptophan | g | 0 | 9.635 |
| Vitamin D | IU | 0 | 714.5 |
| Selenium, Se | mg | 0 | 0.285 |
| Vitamin B-12 | mcg | 0 | 446.7 |
| Vitamin K | mcg | 0 | 12499 |
| Folate | mcg_DFE | 0 | 3135.945 |
| Vitamin A | IU | 0 | 35714.5 |

-continued

| Nutrient | units/Mcal | lower limit | upper limit |
|---|---|---|---|
| Calcium, Ca | g | 0 | 3.55 |
| Copper, Cu | mg | 0 | 35.5 |
| Iodine | mg | 0 | 7 |
| Iron, Fe | mg | 0 | 428.5 |
| Magnesium, Mg | g | 0 | 0.43 |
| Manganese, Mn | mg | 0 | 70 |
| Niacin | mg | 0 | 174.485 |
| Pantothenic acid | mg | 0 | 138.19 |
| Phosphorus, P | g | 0 | 2.3 |
| Potassium, K | mg | 0 | 67838.605 |
| Riboflavin | mg | 0 | 55.63 |
| Sodium, Na | mg | 0 | 6908.8 |
| Thiamine | mg | 0 | 23.73 |
| Total Choline | mg | 0 | 18491.46 |
| Vitamin B-6 | mg | 0 | 4.22 |
| Vitamin E | IU | 0 | 143 |
| Zinc, Zn | mg | 0 | 143 |

Canine Vegetarian

To formulate a universal supplement for a canine consuming a vegetarian diet, any current guidelines detailing the dietary needs of dogs may be used. In one embodiment, the nutritional requirements were based off several leading publications of dietary requirement guidelines, including the current official publication of AAFCO and the Nutrient Requirements of Dogs and Cats by the National Research Council (NRC) of the National Academies. In a separate embodiment, the safe upper limit for a nutrient from the NRC guidelines was ignored because of controversy in the veterinary nutrition industry over whether the NRC set the safe upper limit too low. Specifically, the iodine maximum in one embodiment was increased from the NRC value, the linoleic acid safe upper limit was not used, and the requirement for chromium was removed. Using more than one set of guidelines was not necessary, but doing so allowed for the formulation of a supplement containing a broader range of nutrients and applications. In practice, any guideline may be used with the program to formulate a supplement and in one embodiment, the amount of vitamin E required was set to a value higher than recommended by either the AAFCO or NRC guideline.

The foods entered into the Autoloader for Autobalancer were the human foods most commonly fed to canines on a vegetarian diet, and included the protein sources chickpeas, green beans, green peas, kidney beans, pinto beans, lentils, and soy and the carbohydrate sources barley, brown rice, couscous, oats, potato, spaghetti, sweet potato, tapioca, and white rice. Although seven protein sources and nine carbohydrate sources were used, any number of other foods may be inputted into the program in place of or in addition to those listed here.

The metabolizable energy for the above sources was set at 3.5 kcal/g protein, 8.5 kcal/g fat, and 3.5 kcal/g carbohydrate. This specification does not preclude using different values.

The food combinations detailed above were then combined with a high linoleic acid containing vegetable oil. The proportion of each of the three foods making up the combination varied depending on the particular caloric distribution being analyzed by the Autobalancer module at the time. Caloric distributions of 20-50% protein, 12-50% fat (and by subtraction from 100%, 0-68% carbohydrate), were used at 1% increments.

The formulations in the following table were obtained from running the Autoloader for Autobalancer. The amount shown represents data derived from the optimum tenthtile produced by the program. The "best min", "best max", and "best avg" represent respectively, the low end, the high end, and the mean of the optimum tenthtile. The "low" is the smallest amount of nutrient that any particular diet required, and the "high" is the largest amount of nutrient that any particular diet required. With regard to Vitamin D and Vitamin B12, none of the diets were able to provide these nutrients, and thus every diet needs the full daily requirement, 143 IU and 9 mcg, respectively. Because of this, any amount between the minimum daily amount and one half the upper safe limit is claimed.

| nutrient | unit/Mcal | low | best min | best avg | Best max | high |
|---|---|---|---|---|---|---|
| Arginine | g | 0 | 1.313 | 1.38595 | 1.4589 | 1.4589 |
| Chloride | g | 0 | 0.234 | 0.247 | 0.26 | 0.26 |
| Cystine | g | 0 | 0.55335 | 0.6841 | 0.81485 | 0.81485 |
| Histidine | g | 0 | 0.4588 | 0.4843 | 0.5098 | 0.5098 |
| Isoleucine | g | 0 | 0.9538 | 1.0068 | 1.0598 | 1.0598 |
| Leucine | g | 0 | 1.5207 | 1.6102 | 1.6997 | 1.6997 |
| Lysine | g | 0 | 1.6197 | 1.7097 | 1.7997 | 1.7997 |
| Methionine | g | 0 | 0.55335 | 0.6841 | 0.81485 | 0.81485 |
| Phenylalanine | g | 0 | 0.94035 | 1.5575 | 2.17465 | 2.17465 |
| Threonine | g | 0 | 1.2328 | 1.3013 | 1.3698 | 1.3698 |
| Tryptophan | g | 0 | 0.4138 | 0.4368 | 0.4598 | 0.4598 |
| Tyrosine | g | 0 | 0.94035 | 0.9926 | 1.04485 | 1.04485 |
| Valine | g | 0 | 0.9987 | 1.1142 | 1.2297 | 1.2297 |
| Vitamin D | IU | 143 | 143 | 143 | 143 | 143 |
| Selenium, Se | mcg | 0 | 20.0832 | 51.19895 | 82.3147 | 82.3147 |
| Vitamin B12 | mcg | 9 | 9 | 9 | 9 | 9 |
| Vitamin K | mcg | 0 | 224.9993 | 237.49925 | 249.9992 | 249.9992 |
| Vitamin A | mcg_RAE | 0 | 385.83 | 407.265 | 428.7 | 428.7 |
| Calcium, Ca | mg | 0 | 1432.0098 | 1511.5659 | 1591.122 | 1591.122 |

-continued

| nutrient | unit/Mcal | low | best min | best avg | Best max | high |
|---|---|---|---|---|---|---|
| Copper, Cu | mg | 0 | 0.9671 | 1.02085 | 1.0746 | 1.0746 |
| Iodine | mg | 0.3906 | 0.4261 | 0.42805 | 0.43 | 0.43 |
| Iron, Fe | mg | 0 | 13.2193 | 13.9537 | 14.6881 | 14.6881 |
| Niacin | mg | 0 | 2.3393 | 2.69425 | 3.0492 | 3.0492 |
| Pantothenic acid | mg | 0 | 1.8199 | 2.346 | 2.8721 | 2.8721 |
| Phosphorus, P | mg | 0 | 745.0466 | 786.43805 | 827.8295 | 827.8295 |
| Potassium, K | mg | 0 | 911.4091 | 962.04295 | 1012.6768 | 1012.6768 |
| Riboflavin | mg | 0 | 0.2323 | 0.58025 | 0.9282 | 0.9282 |
| Sodium, Na | mg | 0 | 147.2695 | 155.45115 | 163.6328 | 163.6328 |
| Thiamine | mg | 0 | 0.1253 | 0.13225 | 0.1392 | 0.1392 |
| Total Choline | mg | 0 | 306.9657 | 366.5756 | 426.1855 | 426.1855 |
| Vitamin E | mg | 4.8625 | 32.2213 | 55.3424 | 78.4635 | 78.4635 |
| Zinc, Zn | mg | 22.3081 | 28.5125 | 28.85715 | 29.2018 | 29.2018 |

The supplement formula may also be described in terms of the percentage contribution of mass each nutrient provides to the total mass of all the nutrients. In these calculations, for each nutrient, 50% of the difference between the "low" and the "high" is added to or subtracted from the "best avg" value, thus creating the "% low" and "% high" values shown in the table below. In the table below, the "best % low", "best % avg", and "best % high" represent the same amount of nutrient they represented in the previous table, but in percentage form.

| | % low | best % low | best % avg | best % high | % high |
|---|---|---|---|---|---|
| Arginine | 7.73974144 | 7.73974144 | 8.103697348 | 8.550455375 | 8.550455375 |
| Chloride | 1.379349355 | 1.379349355 | 1.444217501 | 1.523843532 | 1.523843532 |
| Cystine | 3.597040213 | 3.603499224 | 3.999956244 | 4.322933931 | 4.322933931 |
| Histidine | 2.704585774 | 2.704585774 | 2.831718767 | 2.987775267 | 2.987775267 |
| Isoleucine | 5.62244018 | 5.62244018 | 5.886794249 | 6.211290431 | 6.211290431 |
| Leucine | 9.01723115 | 9.01723115 | 9.414894816 | 9.903029313 | 9.903029313 |
| Lysine | 9.547750133 | 9.547750133 | 9.99667474 | 10.54773235 | 10.54773235 |
| Methionine | 3.597040213 | 3.603499224 | 3.999956244 | 4.322933931 | 4.322933931 |
| Phenylalanine | 6.112725697 | 6.123701989 | 9.106756102 | 11.53693106 | 11.53693106 |
| Threonine | 7.267049026 | 7.267049026 | 7.608745885 | 8.028180797 | 8.028180797 |
| Tryptophan | 2.439326283 | 2.439326283 | 2.553984633 | 2.694728434 | 2.694728434 |
| Tyrosine | 5.543127592 | 5.543127592 | 5.803766361 | 6.123701989 | 6.123701989 |
| Valine | 6.492028663 | 6.503686049 | 6.514765746 | 6.523791931 | 6.523791931 |
| Vitamin D | 1.34836E−05 | 1.89661E−05 | 2.09031E−05 | 2.32809E−05 | 4.64784E−05 |
| Selenium, Se | 0.00013055 | 0.000130785 | 0.000299362 | 0.000436695 | 0.000436695 |
| Vitamin B12 | 3.39448E−05 | 4.77467E−05 | 5.26233E−05 | 5.86094E−05 | 0.000117009 |
| Vitamin K | 0.001326293 | 0.001326293 | 0.001388666 | 0.00146523 | 0.00146523 |
| Vitamin A | 0.002274335 | 0.002274335 | 0.002381292 | 0.002512584 | 0.002512584 |
| Calcium, Ca | 8.441204249 | 8.441204249 | 8.838177838 | 9.325465264 | 9.325465264 |
| Copper, Cu | 0.005700957 | 0.005700957 | 0.005968945 | 0.006297902 | 0.006297902 |
| Iodine | 0.001688754 | 0.002281232 | 0.002502823 | 0.002774828 | 0.005308941 |
| Iron, Fe | 0.077923159 | 0.077923159 | 0.081587764 | 0.086086089 | 0.086086089 |
| Niacin | 0.015206571 | 0.015233877 | 0.015753372 | 0.016176585 | 0.016176585 |
| Pantothenic acid | 0.011830222 | 0.011851465 | 0.013717143 | 0.015237036 | 0.015237036 |
| Phosphorus, P | 4.391792643 | 4.391792643 | 4.598330344 | 4.851856592 | 4.851856592 |
| Potassium, K | 5.372442658 | 5.372442658 | 5.625098238 | 5.935234454 | 5.935234454 |
| Riboflavin | 0.001510061 | 0.001512773 | 0.003392742 | 0.004924277 | 0.004924277 |
| Sodium, Na | 0.868103066 | 0.868103066 | 0.908928224 | 0.959041346 | 0.959041346 |
| Thiamine | 0.000738482 | 0.000738482 | 0.00077327 | 0.000815973 | 0.000815973 |
| Total Choline | 1.995424174 | 1.99900725 | 2.143380149 | 2.260994979 | 2.260994979 |
| Vitamin E | 0.209829998 | 0.209829998 | 0.323588917 | 0.416263762 | 0.416263762 |
| Zinc, Zn | 0.121839203 | 0.154921092 | 0.168728749 | 0.18567773 | 0.330358258 |

To reduce the high cost associated with including amino acids, in an alternative embodiment of the invention, the supplement contains limited amounts of amino acids. In this embodiment, the percentage of total mass contributed by each nutrient is as follows:

|  | % low | best % low | best % avg | best % high | % high |
|---|---|---|---|---|---|
| Arginine | 10.16621976 | 10.16621976 | 10.75448033 | 11.49344061 | 11.49344061 |
| Chloride | 1.811787742 | 1.811787742 | 1.916632375 | 2.048335951 | 2.048335951 |
| Cystine | 4.832126054 | 4.84378931 | 5.308373312 | 5.678212467 | 5.678212467 |
| Lysine | 12.54105538 | 12.54105538 | 13.26666547 | 14.17816128 | 14.17816128 |
| Methionine | 4.832126054 | 4.84378931 | 5.308373312 | 5.678212467 | 5.678212467 |
| Phenylalanine | 8.211601581 | 8.231421845 | 12.08564747 | 15.15386236 | 15.15386236 |
| Threonine | 9.545334034 | 9.545334034 | 10.09762636 | 10.79140411 | 10.79140411 |
| Tryptophan | 3.204076937 | 3.204076937 | 3.389413043 | 3.622228276 | 3.622228276 |
| Tyrosine | 7.280947777 | 7.280947777 | 7.702223869 | 8.231421845 | 8.231421845 |
| Vitamin D | 1.78316E−05 | 2.49121E−05 | 2.77407E−05 | 3.1294E−05 | 6.24373E−05 |
| Selenium, Se | 0.000175376 | 0.0001758 | 0.000397286 | 0.000573603 | 0.000573603 |
| Vitamin B12 | 4.48908E−05 | 6.27157E−05 | 6.98368E−05 | 7.87822E−05 | 0.000157185 |
| Vitamin K | 0.001742098 | 0.001742098 | 0.00184291 | 0.001969548 | 0.001969548 |
| Vitamin A | 0.002987359 | 0.002987359 | 0.003160232 | 0.003377391 | 0.003377391 |
| Calcium, Ca | 11.08759744 | 11.08759744 | 11.72921515 | 12.53520152 | 12.53520152 |
| Copper, Cu | 0.007488258 | 0.007488258 | 0.007921434 | 0.00846558 | 0.00846558 |
| Iodine | 0.002233319 | 0.002996418 | 0.003321516 | 0.003729897 | 0.007131829 |
| Iron, Fe | 0.102352767 | 0.102352767 | 0.108275762 | 0.1157161 | 0.1157161 |
| Niacin | 0.020427925 | 0.020477232 | 0.020906424 | 0.021248089 | 0.021248089 |
| Pantothenic acid | 0.015892267 | 0.015930626 | 0.018204128 | 0.020013983 | 0.020013983 |
| Phosphorus, P | 5.768659002 | 5.768659002 | 6.102480275 | 6.521819385 | 6.521819385 |
| Potassium, K | 7.056751588 | 7.056751588 | 7.465112002 | 7.97808558 | 7.97808558 |
| Riboflavin | 0.002028559 | 0.002033455 | 0.004502534 | 0.006468082 | 0.006468082 |
| Sodium, Na | 1.140261159 | 1.140261159 | 1.206245777 | 1.289134237 | 1.289134237 |
| Thiamine | 0.000970003 | 0.000970003 | 0.001026213 | 0.001096823 | 0.001096823 |
| Total Choline | 2.68057641 | 2.687046492 | 2.844496611 | 2.969837172 | 2.969837172 |
| Vitamin E | 0.282051484 | 0.282051484 | 0.429437391 | 0.546766183 | 0.546766183 |
| Zinc, Zn | 0.161128187 | 0.203490243 | 0.223921247 | 0.249586234 | 0.44379063 |

Publication for AAFCO, or if no upper limit for the nutrient is published, (b) 50 times the high value for the nutrient in the optimum tenthtile as determined using Autoloader for Autobalancer. In yet another embodiment, amino acids may be excluded in order to reduce production costs.

Although a supplement having amounts of nutrients within the optimum tenthtile will complete and balance the diet of many canines, it is expected that the program may be used to create a supplement for a vast range of diets. Thus, the following table represents a wider range of possible supplement formulations that may result. The "low" for all nutrients on this table is zero because it is expected that certain diet combinations will provide the daily requirement for each nutrient listed. The "high" is either (a) 50% of the current nutrient upper limit (on an energy basis) as published in the Official

| BI can vegetarian | units/Mcal | lower limit | upper limit |
|---|---|---|---|
| Arginine | g | 0 | 72.945 |
| Chloride | g | 0 | 13 |
| Cystine | g | 0 | 40.7425 |
| Histidine | g | 0 | 25.49 |
| Isoleucine | g | 0 | 52.99 |
| Leucine | g | 0 | 84.985 |
| Lysine | g | 0 | 89.985 |

| BI can vegetarian | units/Mcal | lower limit | upper limit |
|---|---|---|---|
| Methionine | g | 0 | 40.7425 |
| Phenylalanine | g | 0 | 108.7325 |
| Threonine | g | 0 | 68.49 |
| Tryptophan | g | 0 | 22.99 |
| Tyrosine | g | 0 | 52.2425 |
| Valine | g | 0 | 61.485 |
| Vitamin D | IU | 0 | 714.5 |
| Selenium, Se | mg | 0 | 0.285 |
| Vitamin B12 | mcg | 0 | 450 |
| Vitamin K | mcg | 0 | 12499.96 |
| Vitamin A, RAE | IU | 0 | 35714.5 |
| Calcium, Ca | g | 0 | 3.55 |
| Copper, Cu | mg | 0 | 35.5 |
| Iodine | mg | 0 | 7 |
| Iron, Fe | mg | 0 | 428.5 |
| Niacin | mg | 0 | 152.46 |
| Pantothenic acid | mg | 0 | 143.605 |
| Phosphorus, P | g | 0 | 2.3 |
| Potassium, K | mg | 0 | 50633.84 |
| Riboflavin | mg | 0 | 46.41 |
| Sodium, Na | mg | 0 | 8181.64 |
| Thiamine | mg | 0 | 6.96 |
| Total Choline | mg | 0 | 21309.275 |
| Vitamin E | IU | 0 | 143 |
| Zinc, Zn | mg | 0 | 143 |

Canine Renal

For the universal supplement for canines with renal disorders, any current guidelines detailing the dietary needs of dogs may be used. In one embodiment, the nutritional requirements were based on generally recognized dietary levels for dogs with renal disorders, as well as the current official publication of AAFCO and the Nutrient Requirements of Dogs and Cats by the National Research Council (NRC) of the National Academies. In a separate embodiment, the safe upper limit for a nutrient from the NRC requirement guidelines was ignored because of controversy in the veterinary nutrition industry over whether the NRC set the safe upper limit too low. Specifically, the iodine maximum in one embodiment was increased from the NRC value, the linoleic acid safe upper limit was not used, and the requirement for chromium was removed. Using more than one set of guidelines was not necessary, but allowed for the formulation of a supplement containing a broader range of nutrients. In practice, any guideline may be used with the program to formulate a supplement and in one embodiment, the amount of vitamin E required was set to a value higher than recommended by either the AAFCO or NRC guideline.

The foods entered into the Autoloader for Autobalancer were the human foods most commonly fed to canines with renal disorders, and included the protein sources beef, chicken, chicken egg, lamb, pork, and salmon, and the carbohydrate sources barley, brown rice, couscous, oats, potato, spaghetti, sweet potato, tapioca, and white rice. Although six protein sources and nine carbohydrate sources were used, any number of other foods may be inputted into the program in place of or in addition to those listed here. The choice to use the most common foods in this embodiment ensures the supplement will have the broadest possible range of applications.

The metabolizable energy for the above sources was set at 3.5 kcal/g protein, 8.5 kcal/g fat, and 3.5 kcal/g carbohydrate. This specification does not preclude using different values.

The food combinations detailed above were then combined with a high linoleic acid containing vegetable oil. The proportion of each of the three foods making up the combination varied depending on the particular caloric distribution being analyzed by the Autobalancer module at the time. Caloric distributions of 10-14% protein, 13-53% fat (and by subtraction from 100%, 33-77% carbohydrate), were used at 1% increments.

The resulting formulations were obtained from running the Autoloader. The amount shown represents the optimum tenthtile produced by the program. The "best min," "best max," and "best avg" represent respectively, the low end, the high end, and the mean of the optimum tenthtile. The "low" is the smallest amount of nutrient that any particular diet required, and the "high" is the largest amount of nutrient that any particular diet required.

| Nutrient | unit/Mcal | low | best min | best avg | best max | high |
|---|---|---|---|---|---|---|
| Arginine | g | 0 | 0.3613 | 0.381 | 0.4015 | 0.4015 |
| Chloride | g | 0 | 0.1348 | 0.142 | 0.1497 | 0.1497 |
| Cystine | g | 0 | 0.07045 | 0.174 | 0.27825 | 0.27825 |
| Lysine | g | 0 | 1.1184 | 1.18 | 1.2426 | 1.2426 |
| Methionine | g | 0 | 0.07045 | 0.174 | 0.27825 | 0.27825 |
| Threonine | g | 0 | 0.5529 | 0.584 | 0.6144 | 0.6144 |
| Tryptophan | g | 0 | 0.266 | 0.281 | 0.2956 | 0.2956 |
| Vitamin D | IU | 0 | 128.6519 | 135.799 | 142.9466 | 142.9466 |
| Selenium, Se | mcg | 0 | 15.1872 | 46.031 | 76.8746 | 76.8746 |
| Vitamin B-12 | mcg | 1.2295 | 5.5217 | 22.76 | 39.9986 | 39.9986 |
| Folate | mcg_DFE | 0 | 39.9742 | 267.195 | 494.4158 | 494.4158 |
| Vitamin A | mcg_RAE | 0 | 385.83 | 407.265 | 428.7 | 428.7 |
| Calcium, Ca | mg | 565.86 | 704.4697 | 712.17 | 719.8708 | 719.8708 |
| Choline | mg | 0 | 280.1105 | 336.672 | 393.2339 | 393.2339 |
| Copper, Cu | mg | 1.0582 | 1.9485 | 1.998 | 2.0474 | 2.0474 |
| Iodine | mg | 0.2431 | 0.4113 | 0.421 | 0.43 | 0.43 |
| Iron, Fe | mg | 11.0908 | 20.0372 | 20.534 | 21.0313 | 21.0313 |
| Magnesium, Mg | mg | 0 | 77.6668 | 101.982 | 126.2965 | 126.2965 |

| Nutrient | unit/Mcal | low | best min | best avg | best max | high |
| --- | --- | --- | --- | --- | --- | --- |
| Manganese, Mn | mg | 0 | 1.1548 | 1.219 | 1.2831 | 1.2831 |
| Niacin | mg | 0 | 2.8411 | 12.349 | 21.8567 | 21.8567 |
| Pantothenic acid | mg | 0 | 1.9455 | 9.104 | 16.2617 | 16.2617 |
| Phosphorus, P | mg | 0 | 140.3489 | 152.045 | 163.7404 | 233.9148 |
| Potassium, K | mg | 0 | 563.0081 | 594.286 | 625.5646 | 625.5646 |
| Riboflavin | mg | 0 | 0.4646 | 3.55 | 6.6363 | 6.6363 |
| Sodium, Na | mg | 0 | 146.7844 | 157.439 | 168.0938 | 168.0938 |
| Thiamine | mg | 0 | 0.2123 | 4.579 | 8.9458 | 8.9458 |
| Vitamin B-6 | mg | 0 | 0.0531 | 0.711 | 1.369 | 1.369 |
| Vitamin E | mg | 9.2768 | 38.4314 | 58.854 | 79.2762 | 79.2762 |
| Zinc, Zn | mg | 23.0867 | 31.9577 | 32.45 | 32.9433 | 32.9433 |

The supplement formula may also be described in terms of the percentage contribution of mass each nutrient provides to the total mass of all the nutrients. In these calculations, for each nutrient, 50% of the difference between the "low" and the "high" is added to or subtracted from the "best avg" value, thus creating the "% low" and "% high" values shown in the table below. In the table below, the "best % low," "best % avg," and "best % high" represent the same amount of nutrient they represented in the previous table, but in percentage form.

|  | % low | best % low | best % avg | best % high | % high |
| --- | --- | --- | --- | --- | --- |
| Arginine | 7.034918661 | 7.105912513 | 7.445609462 | 7.877302234 | 7.877302234 |
| Chloride | 2.620775523 | 2.649452312 | 2.775004052 | 2.938999007 | 2.938999007 |
| Cystine | 1.361125039 | 1.535997626 | 3.400357077 | 4.924583205 | 4.924583205 |
| Lysine | 21.8053207 | 21.99204705 | 23.05989282 | 24.38409859 | 24.38409859 |
| Methionine | 1.361125039 | 1.535997626 | 3.400357077 | 4.924583205 | 4.924583205 |
| Threonine | 10.80313723 | 10.87390448 | 11.41269272 | 12.05469251 | 12.05469251 |
| Tryptophan | 5.198619504 | 5.231650657 | 5.491381257 | 5.799508426 | 5.799508426 |
| Vitamin D | 6.27637E−05 | 6.32482E−05 | 6.63456E−05 | 7.01239E−05 | 7.01239E−05 |
| Selenium, Se | 0.000296372 | 0.000331121 | 0.000899551 | 0.001360558 | 0.001360558 |
| Vitamin B-12 | 0.000120388 | 0.000120388 | 0.000444782 | 0.000707912 | 0.000707912 |
| Folate, DFE | 0.00078007 | 0.000871544 | 0.0052216 | 0.008750375 | 0.008750375 |
| Vitamin A | 0.007529217 | 0.007587309 | 0.007958888 | 0.008412122 | 0.008412122 |
| Calcium, Ca | 10.28643557 | 12.74057018 | 13.91742701 | 15.35931564 | 24.78963272 |
| Choline | 5.466163022 | 6.107154906 | 6.579339183 | 6.959615668 | 6.959615668 |
| Copper, Cu | 0.03248957 | 0.036235729 | 0.03904548 | 0.042482489 | 0.05867571 |
| Iodine | 0.006705552 | 0.007610317 | 0.008227301 | 0.008967435 | 0.012783842 |
| Iron, Fe | 0.332432846 | 0.372220617 | 0.40128122 | 0.436864324 | 0.60743254 |
| Magnesium, Mg | 1.515629806 | 1.693343087 | 1.992961008 | 2.235247521 | 2.235247521 |
| Manganese, Mn | 0.022537108 | 0.022708833 | 0.023822042 | 0.025177716 | 0.025177716 |
| Niacin | 0.055446087 | 0.061943547 | 0.241327641 | 0.386828887 | 0.386828887 |
| Pantothenic acid | 0.037980755 | 0.042417081 | 0.177912936 | 0.28780627 | 0.28780627 |
| Phosphorus, P | 1.369422535 | 2.897945099 | 2.971306275 | 3.059979805 | 3.50628752 |
| Potassium, K | 10.98671641 | 11.07150017 | 11.61370463 | 12.27507601 | 12.27507601 |
| Riboflavin | 0.009048798 | 0.010129517 | 0.069375101 | 0.117451973 | 0.117451973 |
| Sodium, Na | 2.864396415 | 2.974993367 | 3.076717344 | 3.200290844 | 3.200290844 |
| Thiamine | 0.004140942 | 0.004628705 | 0.08948411 | 0.158326456 | 0.158326456 |
| Vitamin B-6 | 0.00103426 | 0.001157721 | 0.013894563 | 0.024229126 | 0.024229126 |
| Vitamin E | 0.837906873 | 0.837906873 | 1.150141468 | 1.403062868 | 1.403062868 |
| Zinc, Zn | 0.48720408 | 0.583044104 | 0.634147053 | 0.696762972 | 1.074135483 |

To reduce the high cost associated with including amino acids, in an alternative embodiment of the invention, the supplement contains no amino acids. In this embodiment, the percentage of total mass contributed by each nutrient is as follows:

Publication for AAFCO, or if no upper limit for the nutrient is published, (b) 50 times the high value for the nutrient as determined using Autoloader for Autobalancer. In yet another embodiment, amino acids may be excluded in order to reduce production costs.

|  | % low | best % low | best % avg | best % high | % high |
|---|---|---|---|---|---|
| Chloride | 4.998069698 | 5.894572528 | 6.060322454 | 6.27824854 | 6.48726958 |
| Vitamin D | 0.000119696 | 0.000140716 | 0.000144892 | 0.000149798 | 0.000155019 |
| Selenium, Se | 0.00056521 | 0.000707337 | 0.001964526 | 0.003027007 | 0.003027007 |
| Vitamin B-12 | 0.00025124 | 0.000257171 | 0.000971359 | 0.001574981 | 0.001574981 |
| Folate, DFE | 0.001487668 | 0.00186178 | 0.011403436 | 0.019468068 | 0.019468068 |
| Vitamin A | 0.014358937 | 0.016880449 | 0.017381389 | 0.017969856 | 0.018596191 |
| Calcium, Ca | 23.60891661 | 28.34556207 | 30.39422424 | 32.81035508 | 47.27620164 |
| Choline | 10.42449593 | 13.04601882 | 14.36859776 | 15.48393951 | 15.95383529 |
| Copper, Cu | 0.074568449 | 0.080618222 | 0.085271298 | 0.090750499 | 0.111900193 |
| Iodine | 0.015390251 | 0.016931638 | 0.017967576 | 0.01915611 | 0.024380011 |
| Iron, Fe | 0.762983377 | 0.828126408 | 0.87635677 | 0.933223454 | 1.158431977 |
| Magnesium, Mg | 2.890451067 | 3.617295799 | 4.352421159 | 4.973038606 | 4.973038606 |
| Manganese, Mn | 0.042980422 | 0.05052322 | 0.052024881 | 0.053784283 | 0.055660085 |
| Niacin | 0.105740994 | 0.132322937 | 0.527034662 | 0.860627277 | 0.860627277 |
| Pantothenic acid | 0.072432934 | 0.090610775 | 0.38854349 | 0.640319105 | 0.640319105 |
| Phosphorus, P | 2.611619811 | 6.447425942 | 6.48902625 | 6.536686027 | 8.047457167 |
| Potassium, K | 20.95271948 | 24.63217038 | 25.36313232 | 26.22184556 | 27.13579244 |
| Riboflavin | 0.017256924 | 0.021638533 | 0.151508061 | 0.261310298 | 0.261310298 |
| Sodium, Na | 5.46267805 | 6.618844994 | 6.719233147 | 6.836416506 | 7.224275458 |
| Thiamine | 0.007897173 | 0.009887776 | 0.19542406 | 0.352248944 | 0.352248944 |
| Vitamin B-6 | 0.001972433 | 0.002473108 | 0.030344291 | 0.05390561 | 0.05390561 |
| Vitamin E | 1.775509367 | 1.789924933 | 2.511790266 | 3.121571881 | 3.121571881 |
| Zinc, Zn | 1.118206634 | 1.297172152 | 1.384911716 | 1.488415307 | 2.048479148 |

Although a supplement having amounts of nutrients within the optimum tenthtile will complete and balance the diet of many canines, it is expected that the program may be used to create a supplement for a vast range of diets. Thus, the following table represents a wider range of possible supplement formulations that may result. The "low" for all nutrients on this table is zero because it is expected that certain diet combinations will provide the daily requirement for each nutrient listed. The "high" is either (a) 50% of the current nutrient upper limit (on an energy basis) as published in the Official

| Nutrient | units/Mcal | lower limit | upper limit |
|---|---|---|---|
| Arginine | g | 0 | 20.075 |
| Chloride | g | 0 | 7.485 |
| Cystine | g | 0 | 13.9125 |
| Lysine | g | 0 | 62.13 |
| Methionine | g | 0 | 13.9125 |
| Threonine | g | 0 | 30.72 |
| Tryptophan | g | 0 | 14.78 |

-continued

| Nutrient | units/Mcal | lower limit | upper limit |
|---|---|---|---|
| Vitamin D | IU | 0 | 714.5 |
| Selenium, Se | mg | 0 | 0.285 |
| Vitamin B-12 | mcg | 0 | 1999.93 |
| Folate, DFE | mcg_DFE | 0 | 24720.79 |
| Vitamin A | IU | 0 | 35714.5 |
| Calcium, Ca | g | 0 | 3.55 |
| Choline | mg | 0 | 19661.695 |
| Copper, Cu | mg | 0 | 35.5 |
| Iodine | mg | 0 | 7 |
| Iron, Fe | mg | 0 | 428.5 |
| Magnesium, Mg | g | 0 | 0.43 |
| Manganese, Mn | mg | 0 | 64.155 |
| Niacin | mg | 0 | 1092.835 |
| Pantothenic acid | mg | 0 | 813.085 |
| Phosphorus, P | g | 0 | 2.3 |
| Potassium, K | mg | 0 | 31278.23 |
| Riboflavin | mg | 0 | 331.815 |
| Sodium, Na | mg | 0 | 8404.69 |
| Thiamine | mg | 0 | 447.29 |
| Vitamin B-6 | mg | 0 | 68.45 |
| Vitamin E | IU | 0 | 143 |
| Zinc, Zn | mg | 0 | 143 |

Canine Hepatic

For the universal supplement for canines with hepatic disorders, any current guidelines detailing the dietary needs of dogs may be used. In one embodiment, the nutritional requirements were based on generally recognized dietary levels for dogs with hepatic disorders, as well as the current official publication of AAFCO and the Nutrient Requirements of Dogs and Cats by the National Research Council (NRC) of the National Academies. In a separate embodiment, the safe upper limit for a nutrient from the NRC requirement guidelines was ignored because of controversy in the veterinary nutrition industry over whether the NRC set the safe upper limit too low. Specifically, the iodine maximum in one embodiment was increased from the NRC value, the linoleic acid safe upper limit was not used, and the requirement for chromium was removed. Using more than one set of guidelines was not necessary, but allowed for the formulation of a supplement containing a broader range of nutrients. In practice, any guideline may be used with the program to formulate a supplement and in one embodiment, the amount of vitamin E required was set to a value higher than recommended by either the AAFCO or NRC guideline.

The foods entered into the Autoloader for Autobalancer were the human foods most commonly fed to canines with hepatic disorders, and included 2% fat cottage cheese, beef, chicken, chicken egg, lamb, pork, salmon, and soy, and the carbohydrate sources barley, brown rice, couscous, oats, potato, spaghetti, sweet potato, tapioca, and white rice. Although eight protein sources and nine carbohydrate sources were used, any number of other foods may be inputted into the program in place of or in addition to those listed here. The choice to use the most common foods in this embodiment ensures the supplement will have the broadest possible range of applications.

The metabolizable energy for the above sources was set at 3.5 kcal/g protein, 8.5 kcal/g fat, and 3.5 kcal/g carbohydrate. This specification does not preclude the usage of different values.

The food combinations detailed above were then combined with a high linoleic acid containing vegetable oil. The proportion of each of the three foods making up the combination varied depending on the particular caloric distribution being analyzed by the Autobalancer module at the time. Caloric distributions of 13.5-21.5% protein, 15-47% fat (and by subtraction from 100%, 31.5-71.5% carbohydrate), were used at 1% increments.

In one embodiment of the invention, no copper was added to the resulting supplement formulation. In this embodiment, the supplement is intended to be used with a separate copper supplement. In another embodiment, the supplement does contain copper and a second supplement is not needed.

The resulting formulations were obtained from running the Autoloader. The amount shown represents the optimum tenthtile produced by the program. The "best min," "best max," and "best avg" represent respectively, the low end, the high end, and the mean of the optimum tenthtile. The "low" is the smallest amount of nutrient that any particular diet required, and the "high" is the largest amount of nutrient that any particular diet required.

| nutrient | unit/Mcal | low | best min | best avg | best max | high |
|---|---|---|---|---|---|---|
| Chloride | g | 0 | 0.2209 | 0.233 | 0.2454 | 0.2454 |
| Cystine | g | 0 | 0.5318 | 0.56135 | 0.5909 | 0.5909 |
| Lysine | g | 0 | 1.3348 | 1.414 | 1.4924 | 1.4924 |
| Methionine | g | 0 | 0.5318 | 0.56135 | 0.5909 | 0.5909 |
| Threonine | g | 0 | 0.9048 | 0.9551 | 1.0054 | 1.0054 |
| Tryptophan | g | 0 | 0.308 | 0.325 | 0.3423 | 0.3423 |
| Vitamin D | IU | 0 | 128.7 | 135.85 | 143 | 143 |
| Selenium, Se | mcg | 0 | 14.3247 | 45.121 | 75.9163 | 75.9163 |
| Vitamin B-12 | mcg | 0 | 5.4 | 7.7 | 10 | 10 |
| Vitamin K | mcg | 0 | 28.7319 | 30.328 | 31.9244 | 31.9244 |
| Folate | mcg_DFE | 0 | 39.5023 | 50.447 | 61.3915 | 61.3915 |
| Vitamin A | mcg_RAE | 0 | 385.83 | 407.265 | 428.7 | 428.7 |
| Calcium, Ca | mg | 893.7716 | 1588.0237 | 1626.593 | 1665.1628 | 1665.1628 |
| Choline | mg | 0 | 271.5948 | 322.191 | 372.7874 | 372.7874 |
| Copper, Cu | mg | 0 | 0.2714 | 0.317 | 0.3619 | 0.9047 |
| Iodine | mg | 0.1449 | 0.4015 | 0.416 | 0.43 | 0.43 |

-continued

| nutrient | unit/Mcal | low | best min | best avg | best max | high |
|---|---|---|---|---|---|---|
| Iron, Fe | mg | 11.6296 | 20.9457 | 21.696 | 22.4456 | 22.4456 |
| Magnesium, Mg | mg | 0 | 82.8851 | 100.586 | 118.287 | 118.287 |
| Manganese, Mn | mg | 0 | 1.1595 | 1.227 | 1.2951 | 1.2951 |
| Niacin | mg | 0 | 2.795 | 3.175 | 3.5555 | 3.5555 |
| Pantothenic acid | mg | 0 | 1.9493 | 2.483 | 3.0158 | 3.0158 |
| Phosphorus, P | mg | 0 | 1051.1883 | 1109.588 | 1167.987 | 1167.987 |
| Potassium, K | mg | 0 | 1284.2907 | 1440.64 | 1596.9897 | 1596.9897 |
| Riboflavin | mg | 0 | 0.4314 | 0.79 | 1.1494 | 1.1494 |
| Sodium, Na | mg | 0 | 138.1594 | 160.835 | 183.5105 | 183.5105 |
| Thiamine | mg | 0 | 0.1977 | 0.344 | 0.4897 | 0.4897 |
| Vitamin B-6 | mg | 0 | 0.0617 | 0.083 | 0.1044 | 0.1044 |
| Vitamin E | mg | 8.43 | 33.8029 | 79.175 | 124.5474 | 124.5474 |
| Zinc, Zn | mg | 39.5907 | 52.8274 | 53.603 | 54.3787 | 54.3787 |

The supplement formula may also be described in terms of the percentage contribution of mass each nutrient provides to the total mass of all the nutrients in the supplement. In these calculations, for each nutrient, 50% of the difference between the "low" and the "high" is added to or subtracted from the "best avg" value, thus creating the "% low" and "% high" values shown in the table below. In the table below, the "best % low," "best % avg," and "best % high" represent the same amount of nutrient they represented in the previous table, but in percentage form.

|  | % low | best % low | best % avg | best % high | % high |
|---|---|---|---|---|---|
| Chloride | 2.367769033 | 2.560408154 | 2.596364614 | 2.641218976 | 2.676492973 |
| Cystine | 5.7079763 | 6.165220776 | 6.255232944 | 6.358534412 | 6.447059823 |
| Lysine | 14.33541396 | 15.57112115 | 15.75647882 | 15.95970615 | 16.25459691 |
| Methionine | 5.7079763 | 6.165220776 | 6.255232944 | 6.358534412 | 6.447059823 |
| Threonine | 9.711502362 | 10.48995256 | 10.64286628 | 10.8183564 | 10.96933218 |
| Tryptophan | 3.302640668 | 3.571425066 | 3.621538624 | 3.682641216 | 3.733320181 |
| Vitamin D | 3.45344E-05 | 3.73002E-05 | 3.78451E-05 | 3.84704E-05 | 3.90055E-05 |
| Selenium, Se | 0.000153762 | 0.000171275 | 0.000502792 | 0.000792081 | 0.000792081 |
| Vitamin B-12 | 5.79599E-05 | 6.45658E-05 | 8.58026E-05 | 0.000104336 | 0.000104336 |
| Vitamin K | 0.000308385 | 0.000333087 | 0.000337951 | 0.000343537 | 0.000348314 |
| Folate, DFE | 0.000423993 | 0.000472314 | 0.000562141 | 0.000640535 | 0.000640535 |
| Vitamin A, RAE | 0.004141234 | 0.004472889 | 0.004538234 | 0.004613226 | 0.004677392 |
| Calcium, Ca | 15.1416258 | 17.37366101 | 18.12544423 | 18.98740756 | 26.63788247 |
| Choline | 2.915110079 | 3.247357807 | 3.590237388 | 3.88951874 | 3.88951874 |
| Copper, Cu | 0 | 0.003245029 | 0.003532393 | 0.003775924 | 0.005789035 |
| Iodine | 0.004202854 | 0.004486453 | 0.004635569 | 0.004800586 | 0.005870049 |
| Iron, Fe | 0.203946206 | 0.23418866 | 0.241762775 | 0.250439929 | 0.349648432 |
| Magnesium, Mg | 0.889630718 | 0.991026252 | 1.120849489 | 1.234160552 | 1.234160552 |
| Manganese, Mn | 0.012438837 | 0.01351257 | 0.013672701 | 0.013863709 | 0.014105201 |
| Niacin | 0.029994246 | 0.033418773 | 0.035379647 | 0.037096704 | 0.037267362 |
| Pantothenic acid | 0.020932109 | 0.023307054 | 0.027668555 | 0.031465684 | 0.031465684 |
| Phosphorus, P | 11.28274144 | 12.18632208 | 12.36435631 | 12.56866675 | 12.74348885 |
| Potassium, K | 13.78469085 | 15.35578528 | 16.05333355 | 16.6623694 | 16.84854847 |
| Riboflavin | 0.004621765 | 0.005158089 | 0.008803125 | 0.011992393 | 0.011992393 |
| Sodium, Na | 1.482909273 | 1.651920457 | 1.792215891 | 1.914677183 | 1.914677183 |
| Thiamine | 0.002128416 | 0.002363825 | 0.003833259 | 0.005109339 | 0.005109339 |
| Vitamin B-6 | 0.000661172 | 0.000737724 | 0.000924885 | 0.001089269 | 0.001089269 |
| Vitamin E | 0.404168678 | 0.404168678 | 0.882262525 | 1.29947913 | 1.29947913 |
| Zinc, Zn | 0.458976783 | 0.567366206 | 0.597308723 | 0.631637534 | 0.991951398 |

In an alternative embodiment wherein copper is excluded from the supplement, the percentage of total mass contributed by each nutrient is as follows.

|  | % low | best % low | best % avg | best % high | % high |
| --- | --- | --- | --- | --- | --- |
| Chloride | 2.367700239 | 2.560504837 | 2.596456331 | 2.641304687 | 2.676647925 |
| Cystine | 5.707810459 | 6.165453579 | 6.255453911 | 6.358740754 | 6.447433068 |
| Lysine | 14.33499746 | 15.57170912 | 15.75703542 | 15.96022407 | 16.25553795 |
| Methionine | 5.707810459 | 6.165453579 | 6.255453911 | 6.358740754 | 6.447433068 |
| Threonine | 9.711220202 | 10.49034867 | 10.64324224 | 10.81870747 | 10.96996723 |
| Tryptophan | 3.302544713 | 3.571559925 | 3.621666556 | 3.682760723 | 3.733536317 |
| Vitamin D | 3.45334E−05 | 3.73016E−05 | 3.78464E−05 | 3.84717E−05 | 3.90078E−05 |
| Selenium, Se | 0.000153758 | 0.000171281 | 0.00050281 | 0.000792111 | 0.000792111 |
| Vitamin B-12 | 5.79582E−05 | 6.45679E−05 | 8.58056E−05 | 0.00010434 | 0.00010434 |
| Vitamin K | 0.000308376 | 0.000333099 | 0.000337963 | 0.000343548 | 0.000348334 |
| Folate, DFE | 0.00042398 | 0.00047233 | 0.000562161 | 0.000640559 | 0.000640559 |
| Vitamin A, RAE | 0.004141114 | 0.004473058 | 0.004538394 | 0.004613375 | 0.004677662 |
| Calcium, Ca | 15.14250241 | 17.37431705 | 18.12608452 | 18.98802373 | 26.63710853 |
| Choline | 2.915025383 | 3.247463188 | 3.590364213 | 3.889665611 | 3.889665611 |
| Iodine | 0.004203097 | 0.004486622 | 0.004635733 | 0.004800742 | 0.005869879 |
| Iron, Fe | 0.203958013 | 0.234197504 | 0.241771316 | 0.250448056 | 0.349638273 |
| Magnesium, Mg | 0.88960487 | 0.991058412 | 1.120889084 | 1.234207154 | 1.234207154 |
| Manganese, Mn | 0.012438476 | 0.01351308 | 0.013673184 | 0.013864159 | 0.014106017 |
| Niacin | 0.029993374 | 0.033419858 | 0.035380896 | 0.037098105 | 0.037269519 |
| Pantothenic acid | 0.0209315 | 0.02330781 | 0.027669532 | 0.031466872 | 0.031466872 |
| Phosphorus, P | 11.28241363 | 12.18678225 | 12.36479308 | 12.56907462 | 12.74422662 |
| Potassium, K | 13.78429035 | 15.35628359 | 16.05390064 | 16.66299858 | 16.8495239 |
| Riboflavin | 0.004621631 | 0.005158256 | 0.008803436 | 0.011992845 | 0.011992845 |
| Sodium, Na | 1.482866189 | 1.651974064 | 1.792279202 | 1.914749482 | 1.914749482 |
| Thiamine | 0.002128354 | 0.002363902 | 0.003833395 | 0.005109532 | 0.005109532 |
| Vitamin B-6 | 0.000661153 | 0.000737748 | 0.000924918 | 0.00108931 | 0.00108931 |
| Vitamin E | 0.404181794 | 0.404181794 | 0.882293691 | 1.299528199 | 1.299528199 |
| Zinc, Zn | 0.459003355 | 0.56738763 | 0.597329823 | 0.631658032 | 0.991922578 |

To reduce the high cost associated with including amino acids, in an alternative embodiment of the invention, the supplement contains no amino acids. In this embodiment, the percentage of total mass contributed by each nutrient is as follows:

|  | % low | best % low | best % avg | best % high | % high |
| --- | --- | --- | --- | --- | --- |
| Chloride | 3.866724484 | 4.411677932 | 4.517879915 | 4.648214434 | 4.766800047 |
| Vitamin D | 5.6397E−05 | 6.42696E−05 | 6.58534E−05 | 6.77032E−05 | 6.94684E−05 |
| Selenium, Se | 0.000251104 | 0.000301423 | 0.000874898 | 0.001364785 | 0.001364785 |
| Vitamin B-12 | 9.46524E−05 | 0.000113628 | 0.000149303 | 0.000179775 | 0.000179775 |
| Vitamin K | 0.000503614 | 0.000573921 | 0.000588061 | 0.000604581 | 0.000620343 |
| Folate, DFE | 0.000692408 | 0.000831214 | 0.000978169 | 0.001103666 | 0.001103666 |
| Vitamin A, RAE | 0.006762912 | 0.007706953 | 0.007896886 | 0.008118699 | 0.008330375 |
| Calcium, Ca | 26.96704356 | 29.93546038 | 31.53970749 | 33.41545806 | 43.50143571 |
| Choline | 4.760568855 | 5.714942823 | 6.247297201 | 6.701784621 | 6.815635569 |
| Copper, Cu | 0 | 0.005710844 | 0.006146643 | 0.006506056 | 0.010310199 |
| Iodine | 0.00748523 | 0.007730324 | 0.008066258 | 0.00844843 | 0.009586181 |
| Iron, Fe | 0.363225607 | 0.403515722 | 0.420686363 | 0.440742893 | 0.570999169 |
| Magnesium, Mg | 1.452826196 | 1.74408202 | 1.950366821 | 2.126504269 | 2.140563925 |
| Manganese, Mn | 0.02031345 | 0.023282657 | 0.023791582 | 0.024398391 | 0.025121184 |
| Niacin | 0.0489826 | 0.058812854 | 0.061563385 | 0.063918993 | 0.066372699 |
| Pantothenic acid | 0.034183527 | 0.041017494 | 0.048145476 | 0.054216538 | 0.054216538 |
| Phosphorus, P | 18.42546801 | 20.99748359 | 21.51495854 | 22.11927854 | 22.69599205 |
| Potassium, K | 22.51131798 | 27.0242579 | 27.93407091 | 28.70987864 | 30.00705119 |
| Riboflavin | 0.00754765 | 0.00907759 | 0.015318134 | 0.020663336 | 0.020663336 |
| Sodium, Na | 2.42168958 | 2.907173007 | 3.118597494 | 3.299059589 | 3.385007634 |
| Thiamine | 0.003475845 | 0.004160036 | 0.006670175 | 0.008803581 | 0.008803581 |
| Vitamin B-6 | 0.001079738 | 0.001298302 | 0.001609374 | 0.001876851 | 0.001876851 |
| Vitamin E | 0.711286228 | 0.711286228 | 1.535206619 | 2.239050595 | 2.239050595 |
| Zinc, Zn | 0.817431831 | 0.977592953 | 1.039364451 | 1.111602912 | 1.619922681 |

In an alternative embodiment, copper and all amino acids are excluded from the supplement. The percentage of total mass contributed by each nutrient in this embodiment is as follows.

|  | % low | best % low | best % avg | best % high | % high |
|---|---|---|---|---|---|
| Chloride | 3.866541021 | 4.411964977 | 4.518157631 | 4.648479902 | 4.767291564 |
| Vitamin D | 5.63944E−05 | 6.42737E−05 | 6.58575E−05 | 6.7707E−05 | 6.94755E−05 |
| Selenium, Se | 0.000251092 | 0.00030144 | 0.000874952 | 0.001364874 | 0.001364874 |
| Vitamin B-12 | 9.46479E−05 | 0.000113634 | 0.000149313 | 0.000179787 | 0.000179787 |
| Vitamin K | 0.00050359 | 0.000573958 | 0.000588097 | 0.000604616 | 0.000620407 |
| Folate, DFE | 0.000692376 | 0.000831261 | 0.00097823 | 0.001103737 | 0.001103737 |
| Vitamin A, RAE | 0.006762591 | 0.007707455 | 0.007897371 | 0.008119163 | 0.008331234 |
| Calcium, Ca | 26.9698242 | 29.93740813 | 31.54164624 | 33.41736647 | 43.49937171 |
| Choline | 4.760342982 | 5.715269213 | 6.247681224 | 6.702220671 | 6.816338347 |
| Iodine | 0.007486001 | 0.007730827 | 0.008066754 | 0.008448912 | 0.009585727 |
| Iron, Fe | 0.36326306 | 0.403541977 | 0.420712223 | 0.440768065 | 0.570972077 |
| Magnesium, Mg | 1.452757264 | 1.744181628 | 1.95048671 | 2.126642629 | 2.140784644 |
| Manganese, Mn | 0.020312486 | 0.023284172 | 0.023793045 | 0.024399785 | 0.025123774 |
| Niacin | 0.048980276 | 0.058816212 | 0.061567169 | 0.063923152 | 0.066379543 |
| Pantothenic acid | 0.034181905 | 0.041019836 | 0.048148435 | 0.054220065 | 0.054220065 |
| Phosphorus, P | 18.42459379 | 20.99884979 | 21.51628107 | 22.12054181 | 22.6983323 |
| Potassium, K | 22.5102499 | 27.0258013 | 27.93578802 | 28.71174664 | 30.01014529 |
| Riboflavin | 0.007547292 | 0.009078109 | 0.015319075 | 0.02066468 | 0.02066468 |
| Sodium, Na | 2.421574679 | 2.907339041 | 3.118789195 | 3.299274242 | 3.385356671 |
| Thiamine | 0.00347568 | 0.004160274 | 0.006670585 | 0.008804153 | 0.008804153 |
| Vitamin B-6 | 0.001079687 | 0.001298376 | 0.001609472 | 0.001876973 | 0.001876973 |
| Vitamin E | 0.71132685 | 0.71132685 | 1.535300989 | 2.239196279 | 2.239196279 |
| Zinc, Zn | 0.817516119 | 0.97765656 | 1.039428341 | 1.111666397 | 1.619845821 |

Although a supplement having amounts of nutrients within the optimum tenthtile will complete and balance the diet of many canines, it is expected that the program may be used to create a supplement for a vast range of diets. Thus, the following table represents a wider range of possible supplement formulations that may result. The "low" for all nutrients on this table is zero because it is expected that certain diet combinations will provide the daily requirement for each nutrient listed. The "high" is either (a) 50% of the current nutrient upper limit (on an energy basis) as published in the Official Publication for AAFCO, or if no upper limit for the nutrient is published, (b) 50 times the high value for the nutrient as determined using Autoloader for Autobalancer. In yet another embodiment, amino acids may be excluded in order to reduce production costs.

|  | units/Mcal | intermediate high |
|---|---|---|
| Chloride | g | 12.27 |
| Cystine | g | 29.545 |
| Lysine | g | 74.62 |
| Methionine | g | 29.545 |
| Threonine | g | 50.27 |
| Tryptophan | g | 17.115 |
| Vitamin D | IU | 714.5 |
| Selenium, Se | mg | 0.285 |
| Vitamin B-12 | mcg | 500 |
| Vitamin K | mcg | 1596.22 |
| Folate | mcg_DFE | 3069.575 |
| Vitamin A | IU | 35714.5 |

-continued

|  | units/Mcal | intermediate high |
|---|---|---|
| Calcium, Ca | g | 3.55 |
| Choline | mg | 18639.37 |
| Copper, Cu | mg | 35.5 |
| Iodine | mg | 7 |
| Iron, Fe | mg | 428.5 |
| Magnesium, Mg | g | 0.43 |
| Manganese, Mn | mg | 64.755 |
| Niacin | mg | 177.775 |
| Pantothenic acid | mg | 150.79 |
| Phosphorus, P | g | 2.3 |
| Potassium, K | mg | 79849.485 |
| Riboflavin | mg | 57.47 |
| Sodium, Na | mg | 9175.525 |
| Thiamine | mg | 24.485 |
| Vitamin B-6 | mg | 5.22 |
| Vitamin E | IU | 143 |
| Zinc, Zn | mg | 143 |

Feline Universal

The feline universal supplement may be created according to any given set of nutritional requirements. In one embodiment, the nutritional requirements were based on of the requirements from several leading publications of dietary requirement guidelines, including the current official publication of AAFCO and the Nutrient Requirements of Dogs and Cats by the National Research Council (NRC) of the National Academies. Using more than one set of guidelines was not necessary, but allowed for the formulation of a supplement containing a broader range of nutrients. In practice, any guideline may be used with the program to formulate a supplement, and in one embodiment, the amount of vitamin E required was set to a value higher than recommended by either the AAFCO or NRC guideline. Such customizations may be made depending on the preference of the user.

The foods entered into the Autoloader for Autobalancer were the human foods most commonly fed to felines, and included the protein sources beef, chicken, chicken egg, lamb, pork, and salmon, and the carbohydrate sources barley, brown rice, couscous, oats, potato, spaghetti, sweet potato, tapioca, and white rice. Although six protein sources and nine carbohydrate sources were used, any number of other foods may be inputted into the program in place of or in addition to those listed here. The choice to use the most common foods in this embodiment ensures the supplement will have the broadest possible range of applications.

The guidelines used to make the feline supplements set forth the metabolizable energy for the sources at 3.5 kcal/g protein, 8.5 kcal/g fat, and 3.5 kcal/g carbohydrate.

The food combinations detailed above were then combined with a high linoleic acid containing vegetable oil. The proportion of each of the three foods making up the combination varied depending on the particular caloric distribution being analyzed by the Autobalancer module at the time. Caloric distributions of 22.75-49.75% protein, 19-50% fat (and by subtraction from 100%, 0.25-58.25% carbohydrate), were used at 1% increments.

The resulting formulations were obtained from running the Autoloader. The amount shown represents the optimum tenthtile produced by the program. The "best min," "best max," and "best avg" represent respectively, the low end, the high end, and the mean of the optimum tenthtile. The "low" is the smallest amount of nutrient that any particular diet required, and the "high" is the largest amount of nutrient that any particular diet required.

| nutrient | unit/Mcal | low | best min | best avg | best max | high |
|---|---|---|---|---|---|---|
| Chloride | g | 0 | 0.6197 | 0.654 | 0.6886 | 0.6886 |
| Cystine | g | 0 | 0.1022 | 0.153 | 0.2044 | 0.5109 |
| Methionine | g | 0 | 0.1022 | 0.11495 | 0.1277 | 0.25545 |
| Taurine | g | 0.3173 | 0.4967 | 0.507 | 0.5167 | 0.5167 |
| Vitamin D | IU | 0 | 105.1981 | 111.042 | 116.8868 | 116.8868 |
| Retinol | mcg | 0 | 363.6084 | 383.809 | 404.0094 | 404.0094 |
| Selenium, Se | mcg | 0 | 6.5846 | 44.763 | 82.9422 | 82.9422 |
| Vitamin B-12 | mcg | 0 | 4.3695 | 5.129 | 5.8888 | 5.8888 |
| Vitamin K | mcg | 0 | 26.9986 | 145.922 | 264.8458 | 264.8458 |
| Folate, DFE | mcg_DFE | 0 | 182.3622 | 192.493 | 202.6247 | 202.6247 |
| Calcium, Ca | mg | 1104.072 | 1493.4168 | 1529.785 | 1566.1525 | 1566.1525 |
| Choline | mg | 0 | 458.651 | 503.109 | 547.5666 | 547.5666 |
| Copper, Cu | mg | 0 | 1.015 | 1.09 | 1.1644 | 1.1644 |
| Iodine | mg | 0 | 0.0781 | 0.325 | 0.5718 | 0.5718 |
| Iron, Fe | mg | 5.3811 | 15.9688 | 16.784 | 17.5989 | 17.5989 |
| Magnesium, Mg | mg | 0 | 34.5076 | 39.894 | 45.28 | 45.28 |
| Manganese, Mn | mg | 0 | 1.7062 | 1.802 | 1.8977 | 1.8977 |
| Niacin | mg | 0 | 6.6735 | 10.664 | 14.6548 | 14.6548 |
| Phosphorus, P | mg | 0 | 738.4287 | 779.453 | 820.4764 | 820.4764 |
| Potassium, K | mg | 0 | 917.1498 | 968.103 | 1019.0553 | 1019.0553 |
| Riboflavin | mg | 0 | 0.6918 | 0.761 | 0.8296 | 0.8296 |
| Sodium, Na | mg | 0 | 396.497 | 418.525 | 440.5522 | 440.5522 |
| Thiamine | mg | 0 | 1.0251 | 1.157 | 1.289 | 1.289 |
| Vitamin B-6 | mg | 0 | 0.2354 | 0.314 | 0.3921 | 0.3921 |
| Vitamin E | mg | 1.689 | 34.4708 | 59.407 | 84.3436 | 84.3436 |
| Zinc, Zn | mg | 0 | 15.0493 | 16.389 | 17.7282 | 17.7282 |

The supplement formula may also be described in terms of the percentage contribution of mass each nutrient provides to the total mass of all the nutrients. In these calculations, for each nutrient, 50% of the difference between the "low" and the "high" is added to or subtracted from the "best avg" value, thus creating the "% low" and "% high" values shown in the table below. In the table below, the "best % low," "best % avg," and "best % high" represent the same amount of nutrient they represented in the previous table, but in percentage form.

|  | % low | best % low | best % avg | best % high | % high |
|---|---|---|---|---|---|
| Chloride | 9.631697882 | 11.25546612 | 11.32019254 | 11.39793146 | 11.97124549 |
| Cystine | 0 | 1.879729861 | 2.648301925 | 3.341006788 | 4.897981791 |
| Methionine | 0 | 1.879729861 | 1.989688277 | 2.087311971 | 2.910069118 |
| Taurine | 7.27532269 | 8.445685947 | 8.775745596 | 9.135634266 | 12.66706667 |
| Vitamin D | 4.08955E−05 | 4.77641E−05 | 4.80511E−05 | 4.83718E−05 | 5.08102E−05 |
| Retinol | 0.00565413 | 0.006603709 | 0.006643413 | 0.006687726 | 0.007024862 |
| Selenium, Se | 0.000102378 | 0.000121108 | 0.00077481 | 0.001355726 | 0.001355726 |
| Vitamin B-12 | 6.79413E−05 | 8.03667E−05 | 8.87787E−05 | 9.6255E−05 | 9.68132E−05 |
| Vitamin K | 0.000419823 | 0.000496576 | 0.002525788 | 0.00432902 | 0.00432902 |
| Folate, DFE | 0.002835726 | 0.003311989 | 0.003331893 | 0.003354126 | 0.003523205 |
| Calcium, Ca | 21.11516713 | 25.59944293 | 26.47929778 | 27.46790757 | 40.39107865 |
| Choline | 7.132049916 | 8.435811942 | 8.708395643 | 8.950213932 | 9.316205997 |
| Copper, Cu | 0.015792626 | 0.01866855 | 0.018866988 | 0.019032624 | 0.020052406 |
| Iodine | 0.001216014 | 0.001436467 | 0.005625478 | 0.009346319 | 0.009346319 |
| Iron, Fe | 0.274523215 | 0.287661665 | 0.29051699 | 0.29370871 | 0.331996571 |
| Magnesium, Mg | 0.536600953 | 0.634686557 | 0.690531745 | 0.740121269 | 0.74988467 |
| Manganese, Mn | 0.026533042 | 0.031018731 | 0.031191112 | 0.031381557 | 0.032987179 |
| Niacin | 0.10376856 | 0.122743417 | 0.184584913 | 0.239539072 | 0.239539072 |
| Phosphorus, P | 11.48261352 | 13.41104316 | 13.49167896 | 13.58166808 | 14.26633819 |
| Potassium, K | 14.26173467 | 16.65690154 | 16.75705254 | 16.86882452 | 17.71920191 |
| Riboflavin | 0.010766851 | 0.012724042 | 0.013172273 | 0.013560172 | 0.01409976 |
| Sodium, Na | 6.165558638 | 7.201017079 | 7.244317407 | 7.292634547 | 7.660267245 |
| Thiamine | 0.015938796 | 0.018854316 | 0.020026701 | 0.021069265 | 0.021602924 |
| Vitamin B-6 | 0.003668256 | 0.004329632 | 0.005435077 | 0.006409045 | 0.006409045 |
| Vitamin E | 0.562280298 | 0.634009707 | 1.028285441 | 1.37863278 | 1.37863278 |
| Zinc, Zn | 0.234025067 | 0.276796659 | 0.283679871 | 0.28977513 | 0.302825864 |

To reduce the high cost associated with including amino acids, in an alternative embodiment of the invention, the supplement contains no amino acids except taurine. In this embodiment, the percentage of total mass contributed by each nutrient is as follows:

|  | % low | best % low | best % avg | best % high | % high |
|---|---|---|---|---|---|
| Chloride | 9.298485907 | 11.84317069 | 11.87075709 | 11.90151848 | 12.98513115 |
| Taurine | 7.891494607 | 8.93045977 | 9.202559399 | 9.492501019 | 12.22884504 |
| Vitamin D | 3.94807E−05 | 5.02614E−05 | 5.03881E−05 | 5.05058E−05 | 5.51134E−05 |
| Retinol | 0.005458523 | 0.006948969 | 0.006966519 | 0.006982755 | 0.007619821 |
| Selenium, Se | 9.88366E−05 | 0.000125839 | 0.000812493 | 0.001433544 | 0.001433544 |
| Vitamin B-12 | 6.55908E−05 | 8.35061E−05 | 9.30965E−05 | 0.00010178 | 0.000105013 |
| Vitamin K | 0.000405299 | 0.000515974 | 0.002648631 | 0.004577501 | 0.004577501 |
| Folate, DFE | 0.002737623 | 0.003485149 | 0.003493941 | 0.003502094 | 0.003821598 |
| Calcium, Ca | 22.90348272 | 27.06882503 | 27.76713477 | 28.54089087 | 38.99373508 |
| Choline | 6.885314142 | 8.765341423 | 9.13193384 | 9.463947151 | 10.10522729 |
| Copper, Cu | 0.015246274 | 0.019397803 | 0.019784595 | 0.020125077 | 0.021750713 |
| Iodine | 0.001173945 | 0.00149258 | 0.005899077 | 0.009882789 | 0.009882789 |
| Iron, Fe | 0.297773524 | 0.304173154 | 0.304646463 | 0.305181901 | 0.320511033 |
| Magnesium, Mg | 0.518037055 | 0.65947942 | 0.724116183 | 0.782603481 | 0.813394962 |
| Manganese, Mn | 0.025615122 | 0.032607419 | 0.032708111 | 0.032799175 | 0.035780976 |
| Niacin | 0.100178651 | 0.127538163 | 0.193562314 | 0.253288372 | 0.253288372 |
| Phosphorus, P | 11.08536847 | 14.11221097 | 14.14785509 | 14.18082346 | 15.47460308 |
| Potassium, K | 13.76834494 | 17.52777413 | 17.57204213 | 17.61299083 | 19.21990161 |
| Riboflavin | 0.010394368 | 0.013221084 | 0.013312915 | 0.014338513 | 0.015293917 |
| Sodium, Na | 5.952258969 | 7.577507905 | 7.596649256 | 7.614348169 | 8.30904143 |
| Thiamine | 0.015387388 | 0.019590825 | 0.021000712 | 0.022278619 | 0.023432549 |
| Vitamin B-6 | 0.003541351 | 0.004498761 | 0.005699415 | 0.006776918 | 0.006776918 |
| Vitamin E | 0.542828013 | 0.658776131 | 1.078296738 | 1.457764905 | 1.457764905 |
| Zinc, Zn | 0.225928888 | 0.287609212 | 0.297476817 | 0.306407929 | 0.32847322 |

Although a supplement having amounts of nutrients within the optimum tenthtile will complete and balance the diet of many felines, it is expected that the program may be used to create a supplement for a vast range of diets. Thus, the following table represents a wider range of possible supplement formulations that may result. The "low" for all nutrients on this table is zero because it is expected that certain diet combinations will provide the daily requirement for each nutrient listed. The "high" is either (a) 50% of the current nutrient upper limit (on an energy basis) as published in the Official Publication for AAFCO, or if no upper limit for the nutrient is published, (b) 50 times the high value for the nutrient in the optimum tenthtile as determined using Autoloader for Autobalancer.

| Nutrient | units/Mcal | lower limit | upper limit |
|---|---|---|---|
| Chloride | g | 0 | 34.43 |
| Cystine | g | 0 | 25.545 |
| Methionine | g | 0 | 1.875 |
| Taurine | g | 0 | 25.835 |
| Vitamin D | IU | 0 | 1250 |
| Retinol | IU | 0 | 93750 |
| Selenium, Se | mcg | 0 | 4147.11 |
| Vitamin B-12 | mcg | 0 | 294.44 |
| Vitamin K | mcg | 0 | 13242.29 |

-continued

| Nutrient | units/Mcal | lower limit | upper limit |
|---|---|---|---|
| Folate | mcg_DFE | 0 | 10131.235 |
| Calcium, Ca | mg | 0 | 78307.625 |
| Choline | mg | 0 | 27378.33 |
| Copper, Cu | mg | 0 | 58.22 |
| Iodine | mg | 0 | 28.59 |
| Iron, Fe | mg | 0 | 879.945 |
| Magnesium, Mg | mg | 0 | 2264 |
| Manganese, Mn | mg | 0 | 94.885 |
| Niacin | mg | 0 | 732.74 |
| Phosphorus, P | mg | 0 | 41023.82 |
| Potassium, K | mg | 0 | 50952.765 |
| Riboflavin | mg | 0 | 41.48 |
| Sodium, Na | mg | 0 | 22027.61 |
| Thiamine | mg | 0 | 64.45 |
| Vitamin B-6 | mg | 0 | 19.605 |
| Vitamin E (alpha-tocopherol) | mg | 0 | 4217.18 |
| Zinc, Zn | mg | 0 | 250 |

In another embodiment of the feline supplement, amino acids may be removed from the above table in order to reduce production costs.

Feline Renal

For the universal supplement for felines with renal disorders, any current guidelines detailing the dietary needs of cats may be used. In one embodiment, the nutritional requirements were based on generally recognized dietary levels for dogs with renal disorders, as well as the current official publication of AAFCO and the Nutrient Requirements of Dogs and Cats by the National Research Council (NRC) of the National Academies. Using more than one set of guidelines was not necessary, but allowed for the formulation of a supplement containing a broader range of nutrients. In practice, any guideline may be used with the program to formulate a supplement, and in one embodiment, the amount of vitamin E required was set to a value higher than recommended by either the AAFCO or NRC guideline.

The foods entered into the Autoloader for Autobalancer were the human foods most commonly fed to felines with renal disorders, and included the protein sources beef, chicken, chicken egg, lamb, pork, and salmon, and the carbohydrate sources barley, brown rice, couscous, oats, potato, spaghetti, sweet potato, tapioca, and white rice. Although six protein sources and nine carbohydrate sources were used, any number of other foods may be inputted into the program in place of or in addition to those listed here. The choice to use the most common foods in this embodiment ensures the supplement will have the broadest possible range of applications.

The guidelines used to make the feline supplements set forth the metabolizable energy for the sources at 3.5 kcal/g protein, 8.5 kcal/g fat, and 3.5 kcal/g carbohydrate.

The food combinations detailed above were then combined with a high linoleic acid containing vegetable oil. The proportion of each of the three foods making up the combination varied depending on the particular caloric distribution being analyzed by the Autobalancer module at the time. Caloric distributions of 20-27% protein, 19-64% fat (and by subtraction from 100%, 9-61% carbohydrate), were used at 1% increments.

The resulting formulations were obtained from running the Autoloader. The amount shown represents the optimum tenthtile produced by the program. The "best min," "best max," and "best avg" represent respectively, the low end, the high end, and the mean of the optimum tenthtile. The "low" is the smallest amount of nutrient that any particular diet required, and the "high" is the largest amount of nutrient that any particular diet required.

| nutrient | unit/Mcal | low | best min | best avg | best max | high |
|---|---|---|---|---|---|---|
| Chloride | g | 0 | 0.1694 | 0.179 | 0.1882 | 0.1882 |
| Cystine | g | 0 | 0.3574 | 0.377 | 0.3971 | 0.3971 |
| Methionine | g | 0 | 0.3574 | 0.377 | 0.3971 | 0.3971 |
| Taurine | g | 0.3874 | 0.4947 | 0.501 | 0.5066 | 0.5066 |
| Tryptophan | g | 0 | 0.0938 | 0.099 | 0.1043 | 0.1043 |
| Vitamin D | IU | 0 | 104.1243 | 109.909 | 115.6937 | 115.6937 |
| Retinol | mcg | 0 | 352.2972 | 371.869 | 391.4413 | 391.4413 |
| Selenium, Se | mcg | 0 | 9.0816 | 44.586 | 80.0907 | 80.0907 |
| Vitamin B-12 | mcg | 0 | 4.3224 | 27.744 | 51.1655 | 51.1655 |
| Vitamin K | mcg | 208.7095 | 259.474 | 262.2943 | 265.1145 | 265.1145 |
| Folate | mcg_DFE | 0 | 178.3146 | 1429.629 | 2680.9427 | 2680.9427 |
| Calcium, Ca | mg | 802.712 | 1182.4906 | 1203.589 | 1224.6883 | 1224.6883 |
| Choline | mg | 0 | 478.3302 | 523.89 | 569.4508 | 569.4508 |
| Copper, Cu | mg | 0 | 1.0445 | 1.113 | 1.1819 | 1.1819 |
| Iodine | mg | 0 | 0.0789 | 0.324 | 0.5693 | 0.5693 |
| Iron, Fe | mg | 7.363 | 17.087 | 17.646 | 18.2043 | 18.2043 |
| Magnesium, Mg | mg | 0 | 43.2968 | 48.739 | 54.182 | 54.182 |
| Manganese, Mn | mg | 0 | 1.6781 | 1.773 | 1.8681 | 1.8681 |
| Niacin | mg | 0 | 13.2394 | 43.624 | 74.0078 | 74.0078 |
| Pantothenic acid | mg | 14.2895 | 19.5609 | 19.8538 | 20.1467 | 20.1467 |
| Phosphorus, P | mg | 0 | 40.6954 | 61.043 | 81.3908 | 135.6513 |
| Potassium, K | mg | 0 | 873.2152 | 982.367 | 1091.519 | 1091.519 |
| Riboflavin | mg | 0 | 0.7277 | 21.301 | 41.8737 | 41.8737 |
| Sodium, Na | mg | 0 | 128.495 | 135.634 | 142.7722 | 142.7722 |
| Thiamine | mg | 0 | 1.0417 | 4.267 | 7.4925 | 7.4925 |
| Vitamin B-6 | mg | 0 | 0.4576 | 2.233 | 4.0085 | 4.0085 |
| Vitamin E (alpha-tocopherol) | mg | 6.9774 | 45.2171 | 63.742 | 82.266 | 82.266 |
| Zinc, Zn | mg | 0 | 15.351 | 16.737 | 18.1238 | 18.1238 |

The supplement formula may also be described in terms of the percentage contribution of mass each nutrient provides to the total mass of all the nutrients in the supplement. In these calculations, for each nutrient, 50% of the difference between the "low" and the "high" is added to or subtracted from the "best avg" value, thus creating the "% low" and "% high"

values shown in the table below. In the table below, the "best % low," "best % avg," and "best % high" represent the same amount of nutrient they represented in the previous table, but in percentage form.

|  | % low | best % low | best % avg | best % high | % high |
|---|---|---|---|---|---|
| Chloride | 3.087159287 | 3.741165908 | 3.822324135 | 3.907265241 | 4.127916569 |
| Cystine | 6.48885247 | 7.893820309 | 8.050369827 | 8.243545437 | 8.699459469 |
| Methionine | 6.48885247 | 7.893820309 | 8.050369827 | 8.243545437 | 8.699459469 |
| Taurine | 8.473489668 | 10.0705348 | 10.69823683 | 11.4104139 | 16.05031931 |
| Tryptophan | 1.703573764 | 2.0733454 | 2.114022846 | 2.163527034 | 2.284637823 |
| Vitamin D | 4.73275E−05 | 5.74959E−05 | 5.86743E−05 | 6.00415E−05 | 6.33909E−05 |
| Retinol | 0.006405159 | 0.007781333 | 0.007940804 | 0.008125848 | 0.008579138 |
| Selenium, Se | 0.000165108 | 0.00020947 | 0.000952079 | 0.001592097 | 0.001592097 |
| Vitamin B-12 | 7.8588E−05 | 9.96975E−05 | 0.000592439 | 0.001017102 | 0.001017102 |
| Vitamin K | 0.00439087 | 0.005270124 | 0.005600971 | 0.005984851 | 0.008512116 |
| Folate, DFE | 0.003241977 | 0.004112883 | 0.030527963 | 0.053293578 | 0.053293578 |
| Calcium, Ca | 21.38138577 | 24.34517596 | 25.70115801 | 27.27452432 | 36.09325008 |
| Choline | 8.696574982 | 11.03283922 | 11.18702453 | 11.31992518 | 12.22225158 |
| Copper, Cu | 0.018982939 | 0.023494601 | 0.023766742 | 0.024091727 | 0.025755267 |
| Iodine | 0.001430857 | 0.001819854 | 0.00691862 | 0.011316927 | 0.011316927 |
| Iron, Fe | 0.348653265 | 0.361877293 | 0.376808557 | 0.394117126 | 0.444541847 |
| Magnesium, Mg | 0.787171075 | 0.998654555 | 1.040761207 | 1.07706616 | 1.146173246 |
| Manganese, Mn | 0.030506152 | 0.037135346 | 0.037860227 | 0.038705914 | 0.040917161 |
| Niacin | 0.240722064 | 0.305371 | 0.931536693 | 1.471176718 | 1.471176718 |
| Pantothenic acid | 0.344356816 | 0.400489624 | 0.423953402 | 0.451178422 | 0.615439203 |
| Phosphorus, P | 0 | 0.938652431 | 1.303497945 | 1.617940947 | 1.947854396 |
| Potassium, K | 15.87605298 | 20.14098819 | 20.97723516 | 21.69794724 | 23.09768839 |
| Riboflavin | 0.013241332 | 0.016784634 | 0.454856572 | 0.832393512 | 0.832393512 |
| Sodium, Na | 2.336201427 | 2.838121612 | 2.896296714 | 2.963778318 | 3.129116444 |
| Thiamine | 0.018935668 | 0.024027144 | 0.09111652 | 0.148940944 | 0.148940944 |
| Vitamin B-6 | 0.008317876 | 0.010554691 | 0.04768296 | 0.079683653 | 0.079683653 |
| Vitamin E | 0.948972402 | 1.04294689 | 1.36113176 | 1.63533876 | 1.63533876 |
| Zinc, Zn | 0.27908429 | 0.35407573 | 0.357397984 | 0.36027706 | 0.389951325 |

To reduce the high cost associated with including amino acids, in an alternative embodiment of the invention, the supplement contains no amino acids except taurine. In this embodiment, the percentage of total mass contributed by each nutrient is as follows:

|  | % low | best % low | best % avg | best % high | % high |
|---|---|---|---|---|---|
| Chloride | 3.618384383 | 4.554675941 | 4.673611342 | 4.803066895 | 5.13956595 |
| Taurine | 10.55013062 | 12.26035511 | 13.08088984 | 14.02642971 | 18.81218924 |
| Vitamin D | 5.54714E−05 | 6.99983E−05 | 7.17419E−05 | 7.3807E−05 | 7.89264E−05 |
| Retinol | 0.007507331 | 0.00947337 | 0.009709336 | 0.009988825 | 0.010681671 |
| Selenium, Se | 0.00019352 | 0.000257494 | 0.001164121 | 0.001938295 | 0.001938295 |
| Vitamin B-12 | 9.21111E−05 | 0.000122555 | 0.000724384 | 0.001238269 | 0.001238269 |
| Vitamin K | 0.005466963 | 0.006416103 | 0.006848389 | 0.007356972 | 0.009976845 |
| Folate, DFE | 0.003799843 | 0.005055826 | 0.037326985 | 0.064882174 | 0.064882174 |
| Calcium, Ca | 26.62143007 | 29.63899222 | 31.42517989 | 33.52763551 | 42.30402136 |
| Choline | 10.19304421 | 13.56229013 | 13.67853769 | 13.78142327 | 15.21762056 |
| Copper, Cu | 0.022249441 | 0.028603462 | 0.029059941 | 0.029615132 | 0.032067241 |
| Iodine | 0.001677072 | 0.002237084 | 0.008459498 | 0.013777774 | 0.013777774 |
| Iron, Fe | 0.434099483 | 0.440566882 | 0.460729306 | 0.48447464 | 0.521036696 |
| Magnesium, Mg | 0.922624089 | 1.227611728 | 1.272553872 | 1.311272327 | 1.427071717 |
| Manganese, Mn | 0.035755519 | 0.045210362 | 0.046292251 | 0.04757985 | 0.050944936 |
| Niacin | 0.282144481 | 0.375382077 | 1.13900347 | 1.791081542 | 1.791081542 |
| Pantothenic acid | 0.428750082 | 0.487575397 | 0.518373994 | 0.55461813 | 0.721341335 |
| Phosphorus, P | 0 | 1.153853179 | 1.593805906 | 1.969759398 | 2.425224919 |
| Potassium, K | 18.60793592 | 24.75862467 | 25.64917069 | 26.41612821 | 28.75835564 |
| Riboflavin | 0.015519843 | 0.020632773 | 0.55615975 | 1.013396036 | 1.013396036 |
| Sodium, Na | 2.738204923 | 3.45526623 | 3.541344138 | 3.643270843 | 3.895984829 |
| Thiamine | 0.022194036 | 0.029535743 | 0.111409495 | 0.181327893 | 0.181327893 |
| Vitamin B-6 | 0.009749181 | 0.012974518 | 0.058302649 | 0.097010725 | 0.097010725 |
| Vitamin E | 1.112267492 | 1.282058773 | 1.66427561 | 1.990940335 | 1.990940335 |
| Zinc, Zn | 0.327107915 | 0.435253128 | 0.436995715 | 0.438618681 | 0.485518667 |

Although a supplement having amounts of nutrients within the optimum tenthtile will complete and balance the diet of many felines, it is expected that the program may be used to create a supplement for a vast range of diets. Thus, the following table represents a wider range of possible supplement formulations that may result. The "low" for all nutrients on this table is zero because it is expected that certain diet combinations will provide the daily requirement for each nutrient listed. The "high" is either (a) 50% of the current nutrient upper limit (on an energy basis) as published in the Official Publication for AAFCO, or if no upper limit for the nutrient is published, (b) 50 times the high value for the nutrient as determined using Autoloader for Autobalancer.

| Bl fel renal | units/Mcal | lower limit | upper limit |
|---|---|---|---|
| Chloride | g | 0 | 9.41 |
| Cystine | g | 0 | 19.855 |
| Methionine | g | 0 | 1.875 |
| Taurine | g | 0 | 25.33 |
| Tryptophan | g | 0 | 5.215 |
| Vitamin D | IU | 0 | 1250 |
| Retinol | IU | 0 | 93750 |
| Selenium, Se | mcg | 0 | 4004.535 |
| Vitamin B-12 | mcg | 0 | 2558.275 |
| Vitamin K | mcg | 0 | 13255.725 |
| Folate | mcg_DFE | 0 | 134047.135 |
| Calcium, Ca | mg | 0 | 61234.415 |
| Choline | mg | 0 | 28472.54 |
| Copper, Cu | mg | 0 | 59.095 |
| Iodine | mg | 0 | 28.465 |
| Iron, Fe | mg | 0 | 910.215 |
| Magnesium, Mg | mg | 0 | 2709.1 |
| Manganese, Mn | mg | 0 | 93.405 |
| Niacin | mg | 0 | 3700.39 |
| Pantothenic acid | mg | 0 | 1007.335 |
| Phosphorus, P | mg | 0 | 6782.565 |
| Potassium, K | mg | 0 | 54575.95 |
| Riboflavin | mg | 0 | 2093.685 |
| Sodium, Na | mg | 0 | 7138.61 |
| Thiamine | mg | 0 | 374.625 |
| Vitamin B-6 | mg | 0 | 200.425 |
| Vitamin E (alpha-tocopherol) | mg | 0 | 4113.3 |
| Zinc, Zn | mg | 0 | 250 |

In another embodiment of the feline supplement, amino acids may be removed from the above table in order to reduce production costs.

Although the process of making the supplements is according to the description for the embodiments shown above, other embodiments may be created by altering either the foods, the Atwater factors, the caloric distribution range, or the nutritional requirements of the subject. Therefore, by changing the parameters used by the program, one can create a range of supplements with compositions falling within the scope of applicant's claims.

Additionally, although the embodiments above include amounts of each nutrient per amount of calories consumed, the supplement ingredients may also be described as a percentage by weight of the total weight of all nutrients. This alternative description allows one skilled in the art to take into account variations in nutrient sourcing and purity of source.

In making the conversion from nutrient per amount of calories consumed to nutrient percentage of total nutrients weight, the amount of vitamin D in International Units (IU) was converted to grams using the following conversion: 1 IU Vitamin D=0.000000025 grams cholecalciferol. This conversion may be used to calculate the amount of IU being defined on a mass basis regardless of sourcing.

Many of the features disclosed as software may also be carried out by hardware. One skilled in the art will appreciate that the present invention can be practiced by other than the preferred embodiments, which are presented for purposes of illustration and not of limitation.

We claim:

1. A method of supplementing a diet of a canine, the canine diet comprising foods selected from the group consisting of 2% fat cottage cheese, beef, chicken, chicken egg, lamb, pork, salmon, soy, barley, brown rice, couscous, oats, potato, spaghetti, sweet potato, tapioca, white rice, and combinations thereof, the method comprising the step of combining a supplement with said diet of a canine wherein said canine a dietary supplement comprises arginine, chloride, cystine, histidine, isoleucine, leucine, lysine, methionine, phenylalanine, threonine, tryptophan, tyrosine, valine, Vitamin D, selenium, Vitamin B-12, Vitamin K, Vitamin A, calcium, copper, iodine, iron, niacin, pantothenic acid, phosphorus, potassium, riboflavin, sodium, thiamine, choline, Vitamin E, zinc and:
   a. approximately 3.07 to 3.90 percent by weight tryptophan;
   b. approximately 0.0000570 to 0.0000723 percent by weight vitamin D;
   c. approximately 0.000247 to 0.00143 percent by weight selenium;
   d. approximately 0.00684 to 0.00867 percent by weight vitamin A;
   e. approximately 27.9 to 44.5 percent by weight calcium;
   f. approximately 0.0352 to 0.0401 percent by weight copper;
   g. approximately 0.00795 to 0.00903 percent by weight iodine;
   h. approximately 0.385 to 0.512 percent by weight iron;
   i. approximately 1.38 to 2.40 percent by weight magnesium;
   j. approximately 17.1 to 21.7 percent by weight phosphorus;
   k. approximately 0.677 to 1.51 percent by weight vitamin E; and
   l. approximately 0.611 to 0.643 percent by weight zinc.

2. The method according to claim 1 wherein said supplement further comprises:
   a. approximately 7.74 to 8.55 percent by weight arginine;
   b. approximately 1.38 to 1.52 percent by weight chloride;
   c. approximately 3.60 to 4.32 percent by weight cystine;
   d. approximately 2.70 to 2.99 percent by weight histidine;
   e. approximately 5.62 to 6.21 percent by weight isoleucine;
   f. approximately 9.02 to 9.90 percent by weight leucine;
   g. approximately 9.55 to 10.5 percent by weight lysine;
   h. approximately 3.60 to 4.32 percent by weight methionine;
   i. approximately 6.11 to 11.5 percent by weight phenylalanine;
   j. approximately 7.27 to 8.03 percent by weight threonine;
   k. approximately 2.44 to 2.69 percent by weight tryptophan;
   l. approximately 5.54 to 6.12 percent by weight tyrosine
   m. approximately 6.49 to 6.52 percent by weight valine;
   n. approximately 0.0000135 to 0.0000465 percent by weight vitamin D;
   o. approximately 0.000131 to 0.000437 percent by weight selenium;
   p. approximately 0.0000339 to 0.000117 percent by weight Vitamin B-12;
   q. approximately 0.00132 to 0.00147 percent by weight vitamin K;
   r. approximately 0.00227 to 0.00251 percent by weight vitamin A;
   s. approximately 8.44 to 9.33 percent by weight calcium;
   t. approximately 0.00570 to 0.00630 percent by weight copper;
   u. approximately 0.00169 to 0.00531 percent by weight iodine;
   v. approximately 0.0779 to 0.0861 percent by weight iron;
   w. approximately 0.0152 to 0.0162 percent by weight niacin;

x. approximately 0.0118 to 0.0152 percent by weight pantothenic acid;
y. approximately 4.39 to 4.85 percent by weight phosphorus;
z. approximately 5.37 to 5.94 percent by weight potassium;
aa. approximately 0.00151 to 0.00492 percent by weight riboflavin;
bb. approximately 0.868 to 0.959 percent by weight sodium;
cc. approximately 0.000738 to 0.000816 percent by weight thiamine;
dd. approximately 2.00 to 2.26 percent by weight choline;
ee. approximately 0.210 to 0.416 percent by weight vitamin E; and
ff. approximately 0.122 to 0.330 percent by weight zinc.

3. The method according to claim 1 wherein said supplement further comprises:
a. approximately 10.2 to 11.5 percent by weight arginine;
b. approximately 1.81 to 2.05 percent by weight chloride;
c. approximately 4.83 to 5.68 percent by weight cystine;
d. approximately 12.5 to 14.2 percent by weight lysine;
e. approximately 4.83 to 5.68 percent by weight methionine;
f. approximately 8.21 to 15.2 percent by weight phenylalanine;
g. approximately 9.55 to 10.8 percent by weight threonine;
h. approximately 3.20 to 3.62 percent by weight tryptophan;
i. approximately 7.28 to 8.23 percent by weight tyrosine
j. approximately 0.0000178 to 0.0000624 percent by weight vitamin D;
k. approximately 0.000175 to 0.000574 percent by weight selenium;
l. approximately 0.0000449 to 0.000157 percent by weight vitamin B-12;
m. approximately 0.00174 to 0.00197 percent by weight vitamin K;
n. approximately 0.00299 to 0.00338 percent by weight vitamin A;
o. approximately 11.1 to 12.5 percent by weight calcium;
p. approximately 0.00749 to 0.00847 percent by weight copper;
q. approximately 0.00223 to 0.00713 percent by weight iodine;
r. approximately 0.102 to 0.116 percent by weight iron;
s. approximately 0.0204 to 0.0212 percent by weight niacin;
t. approximately 0.0159 to 0.0200 percent by weight pantothenic acid;
u. approximately 5.77 to 6.52 percent by weight phosphorus;
v. approximately 7.06 to 7.98 percent by weight potassium;
w. approximately 0.00203 to 0.00647 percent by weight riboflavin;
x. approximately 1.14 to 1.29 percent by weight sodium;
y. approximately 0.000970 to 0.00110 percent by weight thiamine;
z. approximately 2.68 to 2.97 percent by weight choline;
aa. approximately 0.282 to 0.547 percent by weight vitamin E; and
bb. approximately 0.161 to 0.444 percent by weight zinc.

4. The method according to claim 1 wherein said supplement further comprises at least 2 nutrients, said nutrients being chosen from the group consisting of isoleucine, leucine, lysine, methionine, and phenylalanine, wherein said nutrients are present in an amount:
a. up to about 1.06 grams isoleucine per megacalorie food;
b. up to about 1.70 grams leucine per megacalorie food;
c. up to about 1.80 grams lysine per megacalorie food;
d. up to about 0.815 grams methionine per megacalorie food; and
e. up to about 2.17 grams phenylalanine per megacalorie food.

5. A method of supplementing a diet of a canine, the canine diet comprising foods selected from the group consisting of 2% fat cottage cheese, beef, chicken, chicken egg, lamb, pork, salmon, soy, barley, brown rice, couscous, oats, potato, spaghetti, sweet potato, tapioca, white rice, and combinations thereof, the method comprising the step of combining a supplement with said diet of a canine wherein said supplement comprises calcium, chloride, folate, choline, iodine, iron, magnesium, manganese, niacin, pantothenic acid, phosphorus, potassium, riboflavin, selenium, sodium, thiamine, vitamin A, vitamin B-12, vitamin B-6, vitamin D, vitamin E, zinc and:
a. between about 0.0 and 8.90 mcg Vitamin B-12 per megacalorie food;
b. between about 920.2 and 1665 milligrams calcium per megacalorie food;
c. between about 8.52 and 21.67 milligrams iron per megacalorie food;
d. approximately 3.07 to 3.90 percent by weight tryptophan;
d. approximately 0.0000570 to 0.0000723 percent by weight vitamin D;
e. approximately 0.000247 to 0.00143 percent by weight selenium;
f. approximately 0.00684 to 0.00867 percent by weight vitamin A;
g. approximately 27.9 to 44.5 percent by weight calcium;
h. approximately 0.0352 to 0.0401 percent by weight copper;
i. approximately 0.00795 to 0.00903 percent by weight iodine;
j. approximately 0.385 to 0.512 percent by weight iron;
k. approximately 1.38 to 2.40 percent by weight magnesium;
l. approximately 17.1 to 21.7 percent by weight phosphorus;
m. approximately 0.677 to 1.51 percent by weight vitamin E; and
n. approximately 0.611 to 0.643 percent by weight zinc.

6. The method according to claim 5 wherein said supplement further comprises:
a. approximately 3.55 to 4.50 percent by weight chloride;
b. approximately 3.07 to 3.90 percent by weight tryptophan;
c. approximately 0.0000570 to 0.0000723 percent by weight vitamin D;
d. approximately 0.000247 to 0.00143 percent by weight selenium;
e. approximately 0.0000946 to 0.000169 percent by weight vitamin B-12;
f. approximately 0.00384 to 0.00777 percent by weight vitamin K;
g. approximately 0.000721 to 0.00119 percent by weight folate;
h. approximately 0.00684 to 0.00867 percent by weight vitamin A;
i. approximately 27.9 to 44.5 percent by weight calcium;
j. approximately 0.0352 to 0.0401 percent by weight copper;

k. approximately 0.00795 to 0.00903 percent by weight iodine;
l. approximately 0.385 to 0.512 percent by weight iron;
m. approximately 1.38 to 2.40 percent by weight magnesium;
n. approximately 0.0223 to 0.0283 percent by weight manganese;
o. approximately 0.0485 to 0.0677 percent by weight niacin;
p. approximately 0.0305 to 0.0522 percent by weight pantothenic acid;
q. approximately 17.1 to 21.7 percent by weight phosphorus;
r. approximately 21.6 to 27.4 percent by weight potassium;
s. approximately 0.00706 to 0.0210 percent by weight riboflavin;
t. approximately 2.20 to 2.79 percent by weight sodium;
u. approximately 0.00326 to 0.00897 percent by weight thiamine;
v. approximately 4.54 to 6.99 percent by weight choline;
w. approximately 0.00135 to 0.00171 percent by weight vitamin B-6;
x. approximately 0.677 to 1.51 percent by weight vitamin E; and
y. approximately 0.611 to 0.643 percent by weight zinc.

7. The method according to claim 5 wherein said supplement further comprises:
a. approximately 3.66 to 4.68 percent by weight chloride;
b. approximately 0.0000588 to 0.0000752 percent by weight vitamin D;
c. approximately 0.000255 to 0.00148 percent by weight selenium;
d. approximately 0.0000976 to 0.000175 percent by weight vitamin B-12;
e. approximately 0.00399 to 0.00802 percent by weight vitamin K;
f. approximately 0.000744 to 0.00123 percent by weight folate;
g. approximately 0.00705 to 0.00902 percent by weight vitamin A;
h. approximately 29.0 to 45.9 percent by weight calcium;
i. approximately 0.0363 to 0.0417 percent by weight copper;
j. approximately 0.00827 to 0.00932 percent by weight iodine;
k. approximately 0.400 to 0.528 percent by weight iron;
l. approximately 1.43 to 2.49 percent by weight magnesium;
m. approximately 0.0230 to 0.0294 percent by weight manganese;
n. approximately 0.0500 to 0.0705 percent by weight niacin;
o. approximately 0.0315 to 0.0542 percent by weight pantothenic acid;
p. approximately 17.6 to 22.6 percent by weight phosphorus;
q. approximately 22.3 to 28.5 percent by weight potassium;
r. approximately 0.00728 to 0.0218 percent by weight riboflavin;
s. approximately 2.27 to 2.91 percent by weight sodium;
t. approximately 0.00337 to 0.00931 percent by weight thiamine;
u. approximately 4.69 to 7.25 percent by weight choline;
v. approximately 0.00139 to 0.00178 percent by weight vitamin B-6;
w. approximately 0.698 to 1.56 percent by weight vitamin E; and
x. approximately 0.634 to 0.664 percent by weight zinc.

8. The method according to claim 5 wherein said supplement further comprises:
a. arginine;
b. cystine;
c. lysine;
d. methionine; and
e. threonine.

9. The method according to claim 5 wherein said supplement further comprises:
a. approximately 7.03 to 7.88 percent by weight arginine;
b. approximately 2.62 to 2.94 percent by weight chloride;
c. approximately 1.36 to 4.92 percent by weight cystine;
d. approximately 21.8 to 24.4 percent by weight lysine;
e. approximately 1.36 to 4.92 percent by weight methionine;
f. approximately 10.8 to 12.1 percent by weight threonine;
g. approximately 5.20 to 5.80 percent by weight tryptophan;
h. approximately 0.0000628 to 0.0000701 percent by weight vitamin D;
i. approximately 0.000296 to 0.00136 percent by weight selenium;
j. approximately 0.000120 to 0.000708 percent by weight vitamin B-12;
k. approximately 0.000780 to 0.00875 percent by weight folate;
l. approximately 0.00753 to 0.00841 percent by weight vitamin A;
m. approximately 10.3 to 24.8 percent by weight calcium;
n. approximately 5.47 to 6.96 percent by weight choline;
o. approximately 0.0325 to 0.0587 percent by weight copper;
p. approximately 0.00671 to 0.0128 percent by weight iodine;
q. approximately 0.332 to 0.607 percent by weight iron;
r. approximately 1.52 to 2.24 percent by weight magnesium;
s. approximately 0.0225 to 0.0252 percent by weight manganese;
t. approximately 0.0554 to 0.387 percent by weight niacin;
u. approximately 0.0380 to 0.288 percent by weight pantothenic acid;
v. approximately 1.37 to 3.51 percent by weight phosphorus;
w. approximately 11.0 to 12.3 percent by weight potassium;
x. approximately 0.00905 to 0.117 percent by weight riboflavin;
y. approximately 2.86 to 3.20 percent by weight sodium;
z. approximately 0.00414 to 0.158 percent by weight thiamine;
aa. approximately 0.00103 to 0.0242 percent by weight vitamin B-6;
bb. approximately 0.838 to 1.40 percent by weight vitamin E; and
cc. approximately 0.487 to 1.07 percent by weight zinc.

10. The method according to claim 5 wherein said supplement further comprises:
a. approximately 5.00 to 6.49 percent by weight chloride;
b. approximately 0.000120 to 0.000155 percent by weight vitamin D;
c. approximately 0.000565 to 0.00303 percent by weight selenium;
d. approximately 0.000251 to 0.00157 percent by weight vitamin B-12;

e. approximately 0.00149 to 0.0195 percent by weight folate;
f. approximately 0.0144 to 0.0186 percent by weight vitamin A;
g. approximately 23.6 to 47.3 percent by weight calcium;
h. approximately 10.4 to 16.0 percent by weight choline;
i. approximately 0.0746 to 0.112 percent by weight copper;
j. approximately 0.0154 to 0.0244 percent by weight iodine;
k. approximately 0.763 to 0.116 percent by weight iron;
l. approximately 2.89 to 4.97 percent by weight magnesium;
m. approximately 0.430 to 0.0557 percent by weight manganese;
n. approximately 0.106 to 0.861 percent by weight niacin;
o. approximately 0.072 to 0.640 percent by weight pantothenic acid;
p. approximately 2.61 to 8.05 percent by weight phosphorus;
q. approximately 21.0 to 27.1 percent by weight potassium;
r. approximately 0.0173 to 0.261 percent by weight riboflavin;
s. approximately 5.46 to 7.22 percent by weight sodium;
t. approximately 0.00790 to 0.352 percent by weight thiamine;
u. approximately 0.00197 to 0.0539 percent by weight vitamin B-6;
v. approximately 0.178 to 3.12 percent by weight vitamin E; and
w. approximately 1.12 to 2.05 percent by weight zinc.

11. The method according to claim 5 wherein said supplement further comprises arginine, cystine, lysine, methionine, threonine, and Vitamin K.

12. The method according to claim 5 wherein said supplement further comprises:
a. approximately 2.37 to 2.68 percent by weight chloride;
b. approximately 5.71 to 6.45 percent by weight cystine;
c. approximately 14.3 to 16.3 percent by weight lysine;
d. approximately 5.71 to 6.45 percent by weight methionine;
e. approximately 9.71 to 11.0 percent by weight threonine;
f. approximately 3.30 to 3.73 percent by weight tryptophan;
g. approximately 0.0000345 to 0.0000390 percent by weight vitamin D;
h. approximately 0.000154 to 0.000792 percent by weight selenium;
i. approximately 0.0000580 to 0.000104 percent by weight vitamin B-12;
j. approximately 0.000308 to 0.000348 percent by weight vitamin K;
k. approximately 0.000424 to 0.000641 percent by weight folate;
l. approximately 0.00414 to 0.00468 percent by weight vitamin A;
m. approximately 15.1 to 26.6 percent by weight calcium;
n. approximately 2.92 to 3.89 percent by weight choline;
o. approximately 0.00420 to 0.00587 percent by weight iodine;
p. approximately 0.234 to 0.350 percent by weight iron;
q. approximately 0.890 to 1.23 percent by weight magnesium;
r. approximately 0.0124 to 0.0141 percent by weight manganese;
s. approximately 0.0300 to 0.0373 percent by weight niacin;
t. approximately 0.0209 to 0.0315 percent by weight pantothenic acid;
u. approximately 11.3 to 12.7 percent by weight phosphorus;
v. approximately 13.8 to 16.8 percent by weight potassium;
w. approximately 0.00462 to 0.0120 percent by weight riboflavin;
x. approximately 1.48 to 1.91 percent by weight sodium;
y. approximately 0.00213 to 0.00511 percent by weight thiamine;
z. approximately 0.000661 to 0.00109 percent by weight vitamin B-6;
aa. approximately 0.404 to 1.30 percent by weight vitamin E; and
bb. approximately 0.459 to 0.992 percent by weight zinc.

13. The method according to claim 5 wherein said supplement further comprises:
a. approximately 2.37 to 2.68 percent by weight chloride;
b. approximately 5.71 to 6.44 percent by weight cystine;
c. approximately 14.3 to 16.3 percent by weight lysine;
d. approximately 5.71 to 6.45 percent by weight methionine;
e. approximately 9.71 to 11.0 percent by weight threonine;
f. approximately 3.30 to 3.73 percent by weight tryptophan;
g. approximately 0.0000345 to 0.0000390 percent by weight vitamin D;
h. approximately 0.000154 to 0.000792 percent by weight selenium;
i. approximately 0.0000580 to 0.000104 percent by weight vitamin B-12;
j. approximately 0.000308 to 0.000348 percent by weight vitamin K;
k. approximately 0.000424 to 0.000641 percent by weight folate;
l. approximately 0.00414 to 0.00468 percent by weight vitamin A;
m. approximately 15.1 to 26.6 percent by weight calcium;
n. approximately 2.92 to 3.89 percent by weight choline;
o. approximately 0.0 to 0.00579 percent by weight copper;
p. approximately 0.00420 to 0.00587 percent by weight iodine;
q. approximately 0.204 to 0.350 percent by weight iron;
r. approximately 0.890 to 1.23 percent by weight magnesium;
s. approximately 0.0124 to 0.0141 percent by weight manganese;
t. approximately 0.0300 to 0.0373 percent by weight niacin;
u. approximately 0.0209 to 0.0315 percent by weight pantothenic acid;
v. approximately 11.3 to 12.7 percent by weight phosphorus;
w. approximately 13.8 to 16.8 percent by weight potassium;
x. approximately 0.00462 to 0.0120 percent by weight riboflavin;
y. approximately 1.48 to 1.91 percent by weight sodium;
z. approximately 0.00213 to 0.00511 percent by weight thiamine;
aa. approximately 0.000661 to 0.00109 percent by weight vitamin B-6;
bb. approximately 0.404 to 1.30 percent by weight vitamin E; and
cc. approximately 0.459 to 0.992 percent by weight zinc.

14. The method according to claim 5 wherein said supplement further comprises:

a. approximately 3.87 to 4.77 percent by weight chloride;
b. approximately 0.0000564 to 0.0000695 percent by weight vitamin D;
c. approximately 0.000251 to 0.00136 percent by weight selenium;
d. approximately 0.0000946 to 0.000180 percent by weight vitamin B-12;
e. approximately 0.000504 to 0.000620 percent by weight vitamin K;
f. approximately 0.000692 to 0.00110 percent by weight folate;
g. approximately 0.00676 to 0.00833 percent by weight vitamin A;
h. approximately 27.0 to 43.5 percent by weight calcium;
i. approximately 4.76 to 6.82 percent by weight choline;
j. approximately 0.00749 to 0.00959 percent by weight iodine;
k. approximately 0.363 to 0.571 percent by weight iron;
l. approximately 1.45 to 2.14 percent by weight magnesium;
m. approximately 0.0203 to 0.0251 percent by weight manganese;
n. approximately 0.0490 to 0.0664 percent by weight niacin;
o. approximately 0.0342 to 0.0542 percent by weight pantothenic acid;
p. approximately 18.4 to 22.7 percent by weight phosphorus;
q. approximately 22.5 to 30.0 percent by weight potassium;
r. approximately 0.00755 to 0.0207 percent by weight riboflavin;
s. approximately 2.42 to 3.39 percent by weight sodium;
t. approximately 0.00348 to 0.00880 percent by weight thiamine;
u. approximately 0.00108 to 0.00188 percent by weight vitamin B-6;
v. approximately 0.711 to 2.24 percent by weight vitamin E; and
w. approximately 0.818 to 1.62 percent by weight zinc.

15. The method according to claim 5 wherein said supplement further comprises:
a. approximately 3.87 to 4.77 percent by weight chloride;
b. approximately 0.0000564 to 0.0000695 percent by weight vitamin D;
c. approximately 0.000251 to 0.00136 percent by weight selenium;
d. approximately 0.0000947 to 0.000180 percent by weight vitamin B-12;
e. approximately 0.000504 to 0.000620 percent by weight vitamin K;
f. approximately 0.000692 to 0.00110 percent by weight folate;
g. approximately 0.00676 to 0.00833 percent by weight vitamin A;
h. approximately 27.0 to 43.5 percent by weight calcium;
i. approximately 4.76 to 6.82 percent by weight choline;
j. approximately 0.0 to 0.0103 percent by weight copper;
k. approximately 0.00749 to 0.00959 percent by weight iodine;
l. approximately 0.363 to 0.571 percent by weight iron;
m. approximately 1.45 to 2.14 percent by weight magnesium;
n. approximately 0.0203 to 0.0251 percent by weight manganese;
o. approximately 0.0490 to 0.0664 percent by weight niacin;
p. approximately 0.0342 to 0.0542 percent by weight pantothenic acid;
q. approximately 18.4 to 22.7 percent by weight phosphorus;
r. approximately 22.5 to 30.0 percent by weight potassium;
s. approximately 0.00755 to 0.0207 percent by weight riboflavin;
t. approximately 2.42 to 3.39 percent by weight sodium;
u. approximately 0.00348 to 0.00880 percent by weight thiamine;
v. approximately 0.000108 to 0.00188 percent by weight vitamin B-6;
w. approximately 0.711 to 2.24 percent by weight vitamin E; and
x. approximately 0.817 to 1.62 percent by weight zinc.

16. A method of supplementing a diet of a feline, the feline diet comprising foods selected from the group consisting of beef, chicken, egg, lamb, pork, salmon, barley, brown rice, couscous, oats, potato, spaghetti, sweet potato, tapioca, white rice, and combinations thereof, the method comprising the step of combining a supplement with said diet of a feline wherein said supplement comprises calcium, chloride, choline, copper, folate, iodine, iron, magnesium, manganese, niacin, potassium, retinol, riboflavin, selenium, sodium, taurine, thiamine, Vitamin B-12, Vitamin B-6, Vitamin D, Vitamin E Vitamin K; and
a. between about 0.0 and 8.90 mcg Vitamin B-12 per megacalorie food;
b. between about 920.2 and 1665 milligrams calcium per megacalorie food;
c. between about 8.52 and 21.67 milligrams iron per megacalorie food
d. approximately 3.07 to 3.90 percent by weight tryptophan;
e. approximately 0.0000570 to 0.0000723 percent by weight vitamin D;
f. approximately 0.000247 to 0.00143 percent by weight selenium sodium selenite;
g. approximately 0.00684 to 0.00867 percent by weight vitamin A;
h. approximately 27.9 to 44.5 percent by weight calcium;
i. approximately 0.0352 to 0.0401 percent by weight copper;
j. approximately 0.00795 to 0.00903 percent by weight iodine;
k. approximately 0.385 to 0.512 percent by weight iron;
l. approximately 1.38 to 2.40 percent by weight magnesium;
m. approximately 17.1 to 21.7 percent by weight phosphorus;
n. approximately 0.677 to 1.51 percent by weight vitamin E; and
o. approximately 0.611 to 0.643 percent by weight zinc.

17. The method of supplementing a diet of a feline according to claim 16 wherein said supplement further comprises cystine, and methionine.

18. The method according to claim 16 wherein said supplement further comprises:
a. between about 0.317 and 0.517 grams taurine per megacalorie food;
b. between about 5.38 and 17.6 mg iron per megacalorie food; and
c. between about 1.69 and 84.3 mg Vitamin E per megacalorie food.

19. The method of supplementing a diet of a feline according to claim 16 wherein said supplement further comprises tryptophan and pantothenic acid.

20. The method according to claim 16 wherein said supplement further comprises:
   a. between about 0.387 and 0.507 grams taurine per megacalorie food;
   b. between about 802 and 1225 milligrams calcium per megacalorie food; and
   c. between about 7.36 and 18.2 milligrams iron per megacalorie food.

21. The method according to claim 16 wherein said supplement further comprises:
   a. approximately 9.63 to 12.0 percent by weight chloride;
   b. approximately 0.0 to 4.90 percent by weight cystine;
   c. approximately 0.0 to 2.91 percent by weight methionine;
   d. approximately 8.45 to 12.7 percent by weight taurine;
   e. approximately 0.0000409 to 0.0000508 percent by weight vitamin D;
   f. approximately 0.00565 to 0.00702 percent by weight retinol;
   g. approximately 0.000102 to 0.00136 percent by weight selenium;
   h. approximately 0.0000679 to 0.0000968 percent by weight vitamin B-12;
   i. approximately 0.000420 to 0.00433 percent by weight vitamin K;
   j. approximately 0.00284 to 0.00352 percent by weight folate;
   k. approximately 25.6 to 40.4 percent by weight calcium;
   l. approximately 7.13 to 9.32 percent by weight choline;
   m. approximately 0.0158 to 0.02 percent by weight copper;
   n. approximately 0.00122 to 0.00935 percent by weight iodine;
   o. approximately 0.288 to 0.332 percent by weight iron;
   p. approximately 0.537 to 0.750 percent by weight magnesium;
   q. approximately 0.0265 to 0.0330 percent by weight manganese;
   r. approximately 0.104 to 0.240 percent by weight niacin;
   s. approximately 11.5 to 14.3 percent by weight phosphorus;
   t. approximately 14.3 to 17.7 percent by weight potassium;
   u. approximately 0.0108 to 0.0141 percent by weight riboflavin;
   v. approximately 6.17 to 7.66 percent by weight sodium;
   w. approximately 0.0159 to 0.0216 percent by weight thiamine;
   x. approximately 0.00367 to 0.00641 percent by weight vitamin B-6;
   y. approximately 0.562 to 1.38 percent by weight vitamin E; and
   z. approximately 0.234 to 0.303 percent by weight zinc.

22. The method according to claim 16 wherein said supplement further comprises:
   a. approximately 9.30 to 13.0 percent by weight chloride;
   b. approximately 7.89 to 12.2 percent by weight taurine;
   c. approximately 0.0000395 to 0.0000551 percent by weight vitamin D;
   d. approximately 0.00546 to 0.00762 percent by weight retinol;
   e. approximately 0.000988 to 0.00143 percent by weight selenium;
   f. approximately 0.0000656 to 0.000105 percent by weight vitamin B-12;
   g. approximately 0.000405 to 0.00458 percent by weight vitamin K;
   h. approximately 0.00274 to 0.00382 percent by weight folate;
   i. approximately 22.9 to 39.0 percent by weight calcium;
   j. approximately 6.89 to 10.1 percent by weight choline;
   k. approximately 0.0152 to 0.0218 percent by weight copper;
   l. approximately 0.00117 to 0.00988 percent by weight iodine;
   m. approximately 0.298 to 0.321 percent by weight iron;
   n. approximately 0.518 to 0.813 percent by weight magnesium;
   o. approximately 0.0256 to 0.0358 percent by weight manganese;
   p. approximately 0.100 to 0.253 percent by weight niacin;
   q. approximately 11.1 to 15.5 percent by weight phosphorus;
   r. approximately 13.8 to 19.2 percent by weight potassium;
   s. approximately 0.0104 to 0.0153 percent by weight riboflavin;
   t. approximately 5.95 to 8.31 percent by weight sodium;
   u. approximately 0.0154 to 0.0234 percent by weight thiamine;
   v. approximately 0.00354 to 0.00678 percent by weight vitamin B-6;
   w. approximately 0.543 to 1.46 percent by weight vitamin E; and
   x. approximately 0.226 to 0.328 percent by weight zinc.

23. The method according to claim 16 wherein said supplement further comprises:
   a. approximately 3.09 to 4.13 percent by weight chloride;
   b. approximately 6.49 to 8.70 percent by weight cystine;
   c. approximately 6.49 to 8.70 percent by weight methionine;
   d. approximately 8.47 to 16.1 percent by weight taurine;
   e. approximately 1.70 to 2.28 percent by weight tryptophan;
   f. approximately 0.0000473 to 0.0000634 percent by weight vitamin D;
   g. approximately 0.00641 to 0.00858 percent by weight retinol;
   h. approximately 0.000165 to 0.00159 percent by weight selenium;
   i. approximately 0.0000786 to 0.00102 percent by weight vitamin B-12;
   j. approximately 0.00439 to 0.00851 percent by weight vitamin K;
   k. approximately 0.00324 to 0.0533 percent by weight folate;
   l. approximately 21.4 to 36.1 percent by weight calcium;
   m. approximately 8.70 to 12.2 percent by weight choline;
   n. approximately 0.0190 to 0.0258 percent by weight copper;
   o. approximately 0.00143 to 0.00113 percent by weight iodine;
   p. approximately 0.349 to 0.445 percent by weight iron;
   q. approximately 0.787 to 1.15 percent by weight magnesium;
   r. approximately 0.0305 to 0.0409 percent by weight manganese;
   s. approximately 0.241 to 1.47 percent by weight niacin;
   t. approximately 0.344 to 0.615 percent by weight pantothenic acid;
   u. approximately 0.0 to 1.95 percent by weight phosphorus;
   v. approximately 15.9 to 23.1 percent by weight potassium;
   w. approximately 0.0132 to 0.832 percent by weight riboflavin;
   x. approximately 2.34 to 3.13 percent by weight sodium;
   y. approximately 0.0189 to 0.149 percent by weight thiamine;

z. approximately 0.00832 to 0.0797 percent by weight vitamin B-6;
aa. approximately 0.949 to 1.64 percent by weight vitamin E; and
bb. approximately 0.279 to 0.390 percent by weight zinc.

24. The method according to claim 16 wherein said supplement further comprises:
   a. approximately 3.62 to 5.14 percent by weight chloride;
   b. approximately 10.6 to 18.8 percent by weight taurine;
   c. approximately 0.0000555 to 0.0000789 percent by weight vitamin D;
   d. approximately 0.00751 to 0.0107 percent by weight retinol;
   e. approximately 0.000194 to 0.00194 percent by weight selenium;
   f. approximately 0.0000921 to 0.00124 percent by weight vitamin B-12;
   g. approximately 0.00547 to 0.00998 percent by weight vitamin K;
   h. approximately 0.00380 to 0.0649 percent by weight folate;
   i. approximately 26.6 to 42.3 percent by weight calcium;
   j. approximately 10.2 to 15.2 percent by weight choline;
   k. approximately 0.0222 to 0.0321 percent by weight copper;
   l. approximately 0.00168 to 0.0138 percent by weight iodine;
   m. approximately 0.434 to 0.521 percent by weight iron;
   n. approximately 0.923 to 1.43 percent by weight magnesium;
   o. approximately 0.0358 to 0.0509 percent by weight manganese;
   p. approximately 0.282 to 1.79 percent by weight niacin;
   q. approximately 0.429 to 0.721 percent by weight pantothenic acid;
   r. approximately 0.0 to 2.43 percent by weight phosphorus;
   s. approximately 18.6 to 28.8 percent by weight potassium;
   t. approximately 0.0155 to 1.01 percent by weight riboflavin;
   u. approximately 2.74 to 3.90 percent by weight sodium;
   v. approximately 0.0222 to 0.181 percent by weight thiamine;
   w. approximately 0.00975 to 0.0970 percent by weight vitamin B-6;
   x. approximately 1.11 to 1.99 percent by weight vitamin E; and
   y. approximately 0.327 to 0.486 percent by weight zinc.

* * * * *